United States Patent
Olsen et al.

(10) Patent No.: US 7,323,453 B2
(45) Date of Patent: Jan. 29, 2008

(54) METHODS OF INHIBITING ORTHOPOXVIRUS REPLICATION WITH NUCLEOSIDE COMPOUNDS

(75) Inventors: David B. Olsen, Lansdale, PA (US); Robert L. LaFemina, Schwenksville, PA (US); Anne B. Eldrup, Danbury, CT (US); Sanjib Bera, Blacksburg, VA (US)

(73) Assignees: Merck & Co., Inc., Rahway, NJ (US); Isis Pharmaceuticals, Inc., Carlsbad, CA (US)

( * ) Notice: Subject to any disclaimer, the term of this patent is extended or adjusted under 35 U.S.C. 154(b) by 484 days.

(21) Appl. No.: 10/504,445

(22) PCT Filed: Feb. 7, 2003

(86) PCT No.: PCT/US03/03703

§ 371 (c)(1),
(2), (4) Date: Apr. 1, 2005

(87) PCT Pub. No.: WO03/068244

PCT Pub. Date: Aug. 21, 2003

(65) Prior Publication Data

US 2005/0164960 A1     Jul. 28, 2005

Related U.S. Application Data

(60) Provisional application No. 60/356,805, filed on Feb. 13, 2002.

(51) Int. Cl.
*A01N 43/04* (2006.01)
*A61K 31/70* (2006.01)
*C07H 19/00* (2006.01)
*C07H 19/22* (2006.01)

(52) U.S. Cl. ............... 514/48; 514/43; 514/45; 514/46; 514/47

(58) Field of Classification Search .............. None
See application file for complete search history.

(56) References Cited

U.S. PATENT DOCUMENTS 6,777,395 B2   8/2004   Bhat et al.

2003/0050229 A1   3/2003   Sommadossi et al.
2003/0060400 A1   3/2003   LaColla et al.

FOREIGN PATENT DOCUMENTS

| WO | WO 01/90121 A2 | 11/2001 |
|---|---|---|
| WO | WO 01/92282 A2 | 12/2001 |
| WO | WO 02/18404 A2 | 3/2002 |
| WO | WO 02/32920 A2 | 4/2002 |
| WO | WO 02/057287 A2 | 7/2002 |
| WO | WO 02/057287 A3 | 7/2002 |
| WO | WO 02/057425 A2 | 7/2002 |
| WO | WO 2004/000858 A2 | 12/2003 |
| WO | WO 2004/046331 A2 | 6/2004 |

OTHER PUBLICATIONS

Neyts et al. Antimicrobial Agents and Chemotherapy (2001), vol. 45, pp. 84-87.*
De Clerq Clinical Microbiology Reviews (2001), vol. 14, pp. 382-397.*
Per Hoffmann, et al., "Recent patents on experimental therapy for hepatitis C virus infection (1999-2002)", Expert Opin. Ther. Patents [2003] pp. (1707-1723), vol. 13, No. 11.

* cited by examiner

*Primary Examiner*—Patrick Lewis
(74) *Attorney, Agent, or Firm*—Kenneth R. Walton; Philippe L. Durette; Sheldon O. Heber

(57) ABSTRACT

The present invention provides methods of inhibiting orthopoxvirus replication and/or treating orthopoxvirus infection with certain nucleoside compounds and derivatives thereof. These compounds are particularly useful as inhibitors of vaccinia virus and variola virus replication and/or for the treatment of vaccinia virus and variola virus infection. The nucleoside compounds may be administered alone or in combination with other agents active against orthopoxvirus infection, in particular against vaccinia virus or variola virus infection. Another aspect of the present invention provides for the use of such nucleoside compounds in the manufacture of a medicament for the inhibition of orthopoxvirus replication and/or for the treatment of orthopoxvirus infection. Yet a further aspect of the present invention provides such nucleoside compounds for use as a medicament for the inhibition of orthopoxvirus replication and/or for the treatment of orthopoxvirus infection.

27 Claims, No Drawings

METHODS OF INHIBITING ORTHOPOXVIRUS REPLICATION WITH NUCLEOSIDE COMPOUNDS

CROSS REFERENCE TO RELATED APPLICATIONS

This application is the National Stage of International Application No. PCT/US03/03703, filed 7 Feb. 2003, which claims the benefit under 35 U.S.C. 119(e) of U.S. Provisional Application No. 60/356,805, filed 13 Feb. 2002.

FIELD OF THE INVENTION

The present invention is concerned with methods of inhibiting orthopoxvirus replication and methods for treating orthopoxvirus infections with certain nucleoside compounds and derivatives thereof. The compounds are particularly useful for inhibiting the replication of vaccinia, variola, cowpox, and monkeypox virus and for the treatment of vaccinia, variola, cowpox, and monkeypox virus infections. Another aspect of the present invention provides for the use of the nucleoside compounds and derivatives thereof and their pharmaceutical compositions for the manufacture of a medicament for the inhibition of orthopoxvirus replication and/or for the treatment of orthopoxvirus infection. Yet a further aspect of the present invention provides for the nucleoside compounds and derivatives thereof and their pharmaceutical compositions for use as a medicament for the inhibition of orthopoxvirus replication and/or for the treatment of orthopoxvirus infection.

BACKGROUND OF THE INVENTION

Orthopoxvirus is a genus of the Poxviridae family of complex DNA viruses that replicate in the cytoplasm of vertebrate and invertebrate cells. The Poxviridae family is characterized by having a large complex virion containing enzymes that synthesize mRNA, a genome composed of a single linear double-stranded DNA molecule of 130-300 kilobase pairs with a hairpin loop at each end, and a cytoplasmic site of replication. Members of the orthopoxvirus genus include cowpox, monkeypox, vaccinia, and variola virus [for a description of the Poxviridae family, reference is made to B. Moss, "Poxviridae: The Viruses and Their Replication," in *Fields Virology*, B. N. Fields, et al., Eds., 3rd ed., Ch. 83, pages 2637-2671 (1996)]. Variola virus is the agent responsible for smallpox infections. Smallpox infections were effectively eradicated subsequent to the introduction of prophylactic vaccinations with cowpox and vaccinia virus. However, most of the human populations worldwide are no longer immune to smallpox as a result of the discontinuation of routine vacination in the early 1980's.

There are very few compounds available as therapeutics against orthopoxvirus infections. Two drugs under investigation are cidofovir and ribavirin. Cidofovir is the generic name for (S)-1-[3-hydroxy-2-(phosphonylmethoxy)-propyl]cytosine [(S)-HPMPC] which is currently the leading agent for the treatment of orthopoxvirus infections in humans. It is potent against vaccinia and cowpox virus infection in mice when administered subcutaneously or intraperitoneally. However, cidofovir's therapeutic utility is limited by safety concerns as well as lack of oral bioavailablity [see D. F. Smee et al., "Effects of cidofovir on the pathogenesis of a lethal vaccinia virus respiratory infection in mice," *Antiviral Res.*, 52: 55-62 (2001) and references cited therein]. Inhibition of vaccinia virus is considered in the art to be predictive of inhibitory activity against other orthopoxviruses, including variola; see E. De Clercq, "Vaccinia Virus Inhibitors as a Paradigm for the Chemotherapy of Poxvirus Infections," *Clin. Microbiol. Rev.*, 14: 382-397 (2001).

Ribavirin has also been found to inhibit vaccinia virus and other orthopoxvirus replication in cell culture (see J. H. Huffman et al., "In vitro effect of 1-β-D-ribofuranosyl-1,2,4-triazole-3-carboxamide on DNA and RNA viruses," *Antimicrobial Agents and Chemotherapy*, 3: 235-241 (1973) and D. F. Smee et al., "Potential of the IMP dehydrogenase inhibitors for antiviral therapies of poxvirus infections," *Antiviral Res.*, 37: A89 (1998)]. Ribavirin was also reported to suppress vaccinia virus-induced lesions in a mouse model and to effectively treat vaccinia keratitis in rabbits. However, ribavirin causes anemia during prolonged administration and at high doses has certain immunosuppressive properties limiting its clinical usefulness against orthopoxvirus.

Consequently, there exists a need for more effective anti-orthopoxvirus agents particularly as a result of the threat of either variola (smallpox) or monkeypox viruses in biowarfare or bioterrorism. Preferably such agents should be effective when administered orally and be safe and well-tolerated by the host.

It has now been found that nucleoside compounds of the present invention and certain derivatives thereof are potent inhibitors of orthopoxvirus replication and in particular of vaccinia, variola, cowpox, and monkeypox virus replication. The instant nucleoside compounds and derivatives thereof are useful to treat orthopoxvirus infection and in particular vaccinia, variola, cowpox, and monkeypox virus infection.

It is therefore an object of the present invention to provide nucleoside compounds and certain derivatives thereof which are useful as inhibitors of the replication of orthopoxvirus and in particular as inhibitors of the replication of vaccinia, variola, cowpox, and monkeypox virus.

It is another object of the present invention to provide nucleoside compounds and certain derivatives thereof which are useful in the treatment of orthopoxvirus infection and in particular in the treatment of vaccinia, variola, cowpox, and monkeypox virus infection.

It is another object of the present invention to provide pharmaceutical compositions comprising the nucleoside compounds of the present invention in association with a pharmaceutically acceptable carrier.

It is another object of the present invention to provide pharmaceutical compositions comprising the nucleoside compounds and derivatives of the present invention for use as inhibitors of orthopoxvirus replication and in particular as inhibitors of vaccinia, variola, cowpox, and monkeypox virus replication.

It is another object of the present invention to provide pharmaceutical compositions comprising the nucleoside compounds and derivatives of the present invention for use in the treatment of orthopoxvirus infection and in particular in the treatment of vaccinia, variola, cowpox, and monkeypox virus infection.

It is another object of the present invention to provide pharmaceutical compositions comprising the nucleoside compounds and derivatives of the present invention in combination with other agents active against orthopoxvirus and in particular against vaccinia, variola, cowpox, and monkeypox virus.

It is another object of the present invention to provide methods for the inhibition of orthopoxvirus replication and in particular for the inhibition of vaccinia, variola, cowpox, and monkeypox virus replication.

It is another object of the present invention to provide methods for the treatment of orthopoxvirus infection and in particular for the treatment of vaccinia, variola, cowpox, and monkeypox virus infection.

It is another object of the present invention to provide methods for the treatment of orthopoxvirus infection in combination with other agents active against orthopoxvirus and in particular for the treatment of vaccinia, variola, cowpox, and monkeypox virus infection in combination with other agents active against vaccinia, variola, cowpox, and monkeypox virus infection.

It is another object of the present invention to provide nucleoside compounds and certain derivatives thereof and their pharmaceutical compositions for use as a medicament for the inhibition of orthopoxvirus replication and/or the treatment of orthopoxvirus infection and in particular for the inhibition of vaccinia, variola, cowpox, and monkeypox virus replication and/or the treatment of vaccinia, variola, cowpox, and monkeypox virus infection.

It is another object of the present invention to provide for the use of the nucleoside compounds and certain derivatives thereof of the present invention and their pharmaceutical compositions for the manufacture of a medicament for the inhibition of orthopoxvirus replication and/or the treatment of orthopoxvirus infection and in particular for the inhibition of vaccinia, variola, cowpox, and monkeypox virus replication and/or the treatment of vaccinia, variola, cowpox, and monkeypox virus infection.

These and other objects will become readily apparent from the detailed description which follows.

SUMMARY OF THE INVENTION

The present invention provides a method for inhibiting orthopoxvirus replication and/or a method for treating orthopoxvirus infection in a mammal in need thereof, comprising administering to the mammal a therapeutically effective amount of a compound of structural formula I:

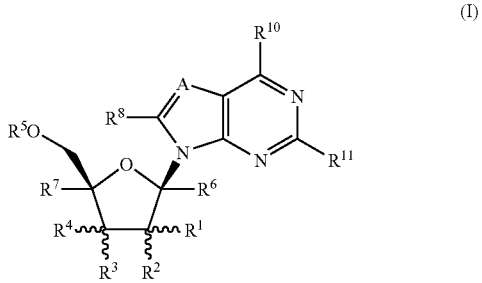

(I)

or a pharmaceutically acceptable salt thereof; wherein
A is N or C—$R^9$;
$R^1$ is $C_{2-4}$ alkenyl, $C_{2-4}$ alkynyl, or $C_{1-4}$ alkyl, wherein alkyl is unsubstituted or substituted with hydroxy, amino, $C_{1-4}$ alkoxy, $C_{1-4}$ alkylthio, or one to three fluorine atoms;
$R^2$ is amino, fluorine, hydroxy, $C_{1-10}$ alkylcarbonyloxy, mercapto, or $C_{1-4}$ alkoxy;
$R^3$ and $R^4$ are each independently selected from the group consisting of hydrogen, cyano, azido, halogen, hydroxy, $C_{1-16}$ alkylcarbonyloxy, $C_{2-18}$ alkenylcarbonyloxy, $C_{1-10}$ alkyloxycarbonyloxy, $C_{3-6}$ cycloalkylcarbonyloxy, $C_{3-6}$ cycloalkyloxycarbonyloxy, mercapto, amino, $C_{1-4}$ alkoxy, $C_{2-4}$ alkenyl, $C_{2-4}$ alkynyl, and $C_{1-4}$ alkyl, wherein alkyl is unsubstituted or substituted with hydroxy, amino, $C_{1-4}$ alkoxy, $C_{1-4}$ alkylthio, or one to three fluorine atoms;
$R^5$ is hydrogen, $C_{1-6}$ alkylcarbonyl, $C_{2-18}$ alkenylcarbonyl, $C_{1-10}$ alkyloxycarbonyl, $C_{3-6}$ cycloalkylcarbonyl, $C_{3-6}$ cycloalkyloxycarbonyl, $P_3O_9H_4$, $P_2O_6H_3$, or $P(O)R^{13}R^{14}$;
$R^6$ and $R^7$ are each independently hydrogen, methyl, hydroxymethyl, or fluoromethyl;
$R^8$ is hydrogen, $C_{1-4}$ alkyl, $C_{2-4}$ alkynyl, halogen, cyano, carboxy, $C_{1-4}$ alkyloxycarbonyl, azido, amino, $C_{1-4}$ alkylamino, di($C_{1-4}$ alkyl)amino, hydroxy, $C_{1-6}$ alkoxy, $C_{1-6}$ alkylthio, $C_{1-6}$ alkylsulfonyl, or ($C_{1-4}$ alkyl)$_{0-2}$ aminomethyl;
$R^9$ is hydrogen, cyano, nitro, $NHCONH_2$, $CONR^{12}R^{12}$, $CSNR^{12}R^{12}$, $COOR^{12}$, $C(=NH)NH_2$, hydroxy, $C_{1-3}$ alkoxy, amino, $C_{1-4}$ alkylamino, di($C_{1-4}$ alkyl)amino, halogen, or $C_{1-3}$ alkyl, wherein alkyl is unsubstituted or substituted with one to three groups independently selected from halogen, amino, hydroxy, carboxy, and $C_{1-3}$ alkoxy;
$R^{10}$ and $R^{11}$ are each independently hydrogen, hydroxy, mercapto, halogen, $C_{1-4}$ alkoxy, $C_{1-4}$ alkylthio, amino, $C_{1-4}$ alkylamino, di($C_{1-4}$ alkyl)amino, $C_{3-6}$ cycloalkylamino, di($C_{3-6}$ cycloalkyl)amino, phenyl-$C_{1-2}$ alkylamino, $C_{1-4}$ acylamino, $C_{1-8}$ alkylcarbonyloxy, or OCH($C_{1-4}$ alkyl)O(C=O)$C_{1-4}$ alkyl;
each $R^{12}$ is independently hydrogen or $C_{1-6}$ alkyl; and
$R^{13}$ and $R^{14}$ are each independently hydroxy, $OCH_2CH_2SC(=O)C_{1-4}$ alkyl, $OCH_2O(C=O)OC_{1-4}$ alkyl, $NHCHMeCO_2Me$, $OCH(C_{1-4}$ alkyl)O(C=O)$C_{1-4}$ alkyl,

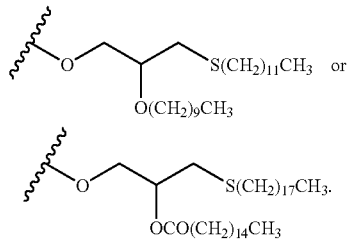

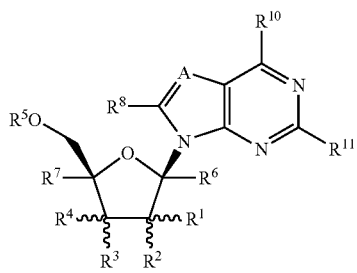

Also encompassed within the present invention are pharmaceutical compositions containing the compounds alone or in combination with other agents active against orthopoxvirus and in particular against vaccinia, variola, cowpox, and monkeypox virus as well as methods for the inhibition of orthopoxvirus replication and for the treatment of orthopoxvirus infection with such compositions.

DETAILED DESCRIPTION OF THE INVENTION

The present invention provides a method for inhibiting orthopoxvirus replication and/or a method for treating orthopoxvirus infection in a mammal in need thereof comprising administering to the mammal a therapeutically effective amount of a compound of structural formula I:

(I)

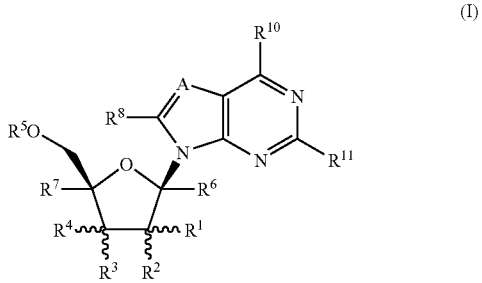

or a pharmaceutically acceptable salt thereof; wherein
A is N or C—$R^9$;
$R^1$ is $C_{2-4}$ alkenyl, $C_{2-4}$ alkynyl, or $C_{1-4}$ alkyl, wherein alkyl is unsubstituted or substituted with hydroxy, amino, $C_{1-4}$ alkoxy, $C_{1-4}$ alkylthio, or one to three fluorine atoms;

$R^2$ is amino, fluorine, hydroxy, $C_{1-10}$ alkylcarbonyloxy, mercapto, or $C_{1-4}$ alkoxy;

$R^3$ and $R^4$ are each independently selected from the group consisting of hydrogen, cyano, azido, halogen, hydroxy, $C_{1-16}$ alkylcarbonyloxy, $C_{2-18}$ alkenylcarbonyloxy, $C_{1-10}$ alkyloxycarbonyloxy, $C_{3-6}$ cycloalkylcarbonyloxy, $C_{3-6}$ cycloalkyloxycarbonyloxy, mercapto, amino, $C_{1-4}$ alkoxy, $C_{2-4}$ alkenyl, $C_{2-4}$ alkynyl, and $C_{1-4}$ alkyl, wherein alkyl is unsubstituted or substituted with hydroxy, amino, $C_{1-4}$ alkoxy, $C_{1-4}$ alkylthio, or one to three fluorine atoms;

$R^5$ is hydrogen, $C_{1-6}$ alkylcarbonyl, $C_{2-18}$ alkenylcarbonyl, $C_{1-10}$ alkyloxycarbonyl, $C_{3-6}$ cycloalkylcarbonyl, $C_{3-6}$ cycloalkyloxycarbonyl, $P_3O_9H_4$, $P_2O_6H_3$, or $P(O)R^{13}R^{14}$;

$R^6$ and $R^7$ are each independently hydrogen, methyl, hydroxymethyl, or fluoromethyl;

$R^8$ is hydrogen, $C_{1-4}$ alkyl, $C_{2-4}$ alkynyl, halogen, cyano, carboxy, $C_{1-4}$ alkyloxycarbonyl, azido, amino, $C_{1-4}$ alkylamino, di($C_{1-4}$ alkyl)amino, hydroxy, $C_{1-6}$ alkoxy, $C_{1-6}$ alkylthio, $C_{1-6}$ alkylsulfonyl, or ($C_{1-4}$ alkyl)$_{0-2}$ aminomethyl;

$R^9$ is hydrogen, cyano, nitro, $NHCONH_2$, $CONR^{12}R^{12}$, $CSNR^{12}R^{12}$, $COOR^{12}$, $C(=NH)NH_2$, hydroxy, $C_{1-3}$ alkoxy, amino, $C_{1-4}$ alkylamino, di($C_{1-4}$ alkyl)amino, halogen, or $C_{1-3}$ alkyl, wherein alkyl is unsubstituted or substituted with one to three groups independently selected from halogen, amino, hydroxy, carboxy, and $C_{1-3}$ alkoxy;

$R^{10}$ and $R^{11}$ are each independently hydrogen, hydroxy, mercapto, halogen, $C_{1-4}$ alkoxy, $C_{1-4}$ alkylthio, amino, $C_{1-4}$ alkylamino, di($C_{1-4}$ alkyl)amino, $C_{3-6}$ cycloalkylamino, di($C_{3-6}$ cycloalkyl)amino, phenyl-$C_{1-2}$ alkylamino, $C_{1-4}$ acylamino, $C_{1-8}$ alkylcarbonyloxy, or $OCH(C_{1-4}$ alkyl)$O(C=O)C_{1-4}$ alkyl;

each $R^{12}$ is independently hydrogen or $C_{1-6}$ alkyl; and $R^{13}$ and $R^{14}$ are each independently hydroxy, $OCH_2CH_2SC(=O)C_{1-4}$ alkyl, $OCH_2O(C=O)OC_{1-4}$ alkyl, $NHCHMeCO_2Me$, $OCH(C_{1-4}$ alkyl)$O(C=O)C_{1-4}$ alkyl,

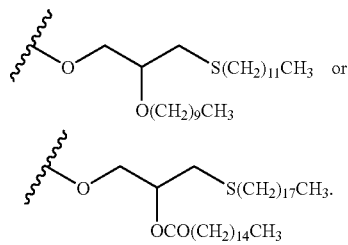

In one embodiment of the present invention is the method of inhibiting orthopoxvirus replication and/or treating orthopoxvirus infection with a compound of structural formula II which is of the stereochemical configuration:

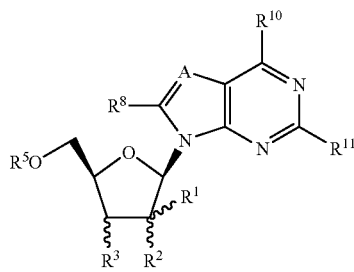

(II)

or a pharmaceutically acceptable salt thereof; wherein

A is N or C—$R^9$;

$R^1$ is $C_{1-3}$ alkyl, wherein alkyl is unsubstituted or substituted with hydroxy, amino, $C_{1-3}$ alkoxy, $C_{1-3}$ alkylthio, or one to three fluorine atoms;

$R^2$ is hydroxy, $C_{1-16}$ alkylcarbonyloxy, fluoro, or $C_{1-3}$ alkoxy;

$R^3$ is hydrogen, halogen, hydroxy, $C_{1-16}$ alkylcarbonyloxy, amino, or $C_{1-3}$ alkoxy;

$R^5$ is hydrogen, $C_{1-16}$ alkylcarbonyl, $P_3O_9H_4$, $P_2O_6H_3$, or $PO_3H_2$;

$R^8$ is hydrogen, amino, or $C_{1-4}$ alkylamino;

$R^9$ is hydrogen, cyano, methyl, halogen, or $CONH_2$; and $R^{10}$ and $R^{11}$ are each independently hydrogen, halogen, hydroxy, amino, $C_{1-4}$ alkylamino, di($C_{1-4}$ alkyl)amino, or $C_{3-6}$ cycloalkylamino.

In a second embodiment of the present invention is the method of inhibiting orthopoxvirus replication and/or treating orthopoxvirus infection with a compound of structural formula II wherein $R^1$ is methyl, fluoromethyl, hydroxymethyl, difluoromethyl, trifluoromethyl, or aminomethyl;

$R^2$ is hydroxy, $C_{1-16}$ alkylcarbonyloxy, fluoro, or methoxy;

$R^3$ is hydrogen, fluoro, hydroxy, $C_{1-16}$ alkylcarbonyloxy, amino, or methoxy;

$R^5$ is hydrogen, $C_{1-16}$ alkylcarbonyl, or $P_3O_9H_4$;

$R^8$ is hydrogen or amino;

$R^9$ is hydrogen, cyano, methyl, halogen, or $CONH_2$; and $R^{10}$ and $R^{11}$ are each independently hydrogen, halogen, hydroxy, amino, $C_{1-4}$ alkylamino, di($C_{1-4}$ alkyl)amino, or $C_{3-6}$ cycloalkylamino.

Illustrative of the invention is a method for inhibiting orthopoxvirus replication and/or treating orthopox infection wherein the compound is selected from:

4-amino-7-(2-C-methyl-β-D-ribofuranosyl)-7H-pyrrolo[2,3-d]pyrimidine, 4-methylamino-7-(2-C-methyl-β-D-ribofuranosyl)-7H-pyrrolo[2,3-d]pyrimidine, 4-dimethylamino-7-(2-C-methyl-β-D-ribofuranosyl)-7H-pyrrolo[2,3-d]pyrimidine, 4-cyclopropylamino-7-(2-C-methyl-β-D-ribofuranosyl)-7H-pyrrolo[2,3-d]pyrimidine, 4-amino-7-(2-C-hydroxymethyl-β-D-ribofuranosyl)-7H-pyrrolo[2,3-d]pyrimidine, 4-amino-7-(2-C-fluoromethyl-β-D-ribofuranosyl)-7H-pyrrolo[2,3-d]pyrimidine, 4-amino-5-methyl-7-(2-C-methyl-β-D-ribofuranosyl)-7H-pyrrolo[2,3-d]pyrimidine, 4-amino-7-(2-C-methyl-β-D-ribofuranosyl)-7H-pyrrolo[2,3-d]pyrimidine-5-carboxamide, 4-amino-7-(2-C-methyl-β-D-ribofuranosyl)-7H-pyrrolo[2,3-d]pyrimidine-5-carbonitrile, 4-amino-5-bromo-7-(2-C-methyl-β-D-ribofuranosyl)-7H-pyrrolo[2,3-d]pyrimidine, 4-amino-5-chloro-7-(2-C-methyl-β-D-ribofuranosyl)-7H-pyrrolo[2,3-d]pyrimidine, 4-amino-5-fluoro-7-(2-C-methyl-β-D-ribofuranosyl)-7H-pyrrolo[2,3-d]pyrimidine, 2,4-diamino-7-(2-C-methyl-β-D-ribofuranosyl)-7H-pyrrolo[2,3-d]pyrimidine, 2-amino-7-(2-C-methyl-β-D-ribofuranosyl)-7H-pyrrolo[2,3-d]pyrimidine, 2-amino-4-cyclopropylamino-7-(2-C-methyl-β-D-ribofuranosyl)-7H-pyrrolo[2,3-d]pyrimidine, 2-amino-7-(2-C-methyl-β-D-ribofuranosyl)-7H-pyrrolo[2,3-d]pyrimidine-4(3H)-one, 7-(2-C-methyl-β-D-ribofuranosyl)-7H-pyrrolo[2,3-d]pyrimidine-4(3H)-one,
4-amino-2-fluoro-7-(2-C-methyl-β-D-ribofuranosyl)-7H-pyrrolo[2,3-d]pyrimidine,
9-(2-C-methyl-β-D-ribofuranosyl)-2-amino-6-hydroxypurine,
9-(2-C-methyl-β-D-ribofuranosyl)-2-amino-6-cyclopropylaminopurine,
9-(2-C-methyl-β-D-ribofuranosyl)-2,6-diaminopurine,
9-(2-C-methyl-β-D-ribofuranosyl)-2-amino-6-methylaminopurine,
6-amino-2-fluoro-9-(2-C-methyl-β-D-ribofuranosyl)purine,
2'-C-methyl-adenosine,
4-amino-7-[2-C-methyl-3-O-(1-oxo-octyl)-β-D-ribofuranosyl]-7H-pyrrolo[2,3-d]pyrimidine, and
4-amino-7-[2-C-methyl-3,5-di-O-(1-oxo-octyl)-β-D-ribofuranosyl]-7H-pyrrolo[2,3-d]pyrimidine;
and the corresponding 5'-triphosphates;

or a pharmaceutically acceptable salt thereof.

Further illustrative of the invention is a method for inhibiting orthopoxvirus replication and/or treating orthopox infection wherein the compound is selected from:
4-amino-7-(2-C-methyl-β-D-ribofuranosyl)-7H-pyrrolo[2,3-d]pyrimidine,
4-amino-7-(2-C-fluoromethyl-β-D-ribofuranosyl)-7H-pyrrolo[2,3-d]pyrimidine,
4-amino-5-methyl-7-(2-C-methyl-β-D-ribofuranosyl)-7H-pyrrolo[2,3-d]pyrimidine,
4-amino-5-bromo-7-(2-C-methyl-β-D-ribofuranosyl)-7H-pyrrolo[2,3-d]pyrimidine,
4-amino-5-chloro-7-(2-C-methyl-β-D-ribofuranosyl)-7H-pyrrolo[2,3-d]pyrimidine,
4-amino-5-fluoro-7-(2-C-methyl-β-D-ribofuranosyl)-7H-pyrrolo[2,3-d]pyrimidine,
4-amino-2-fluoro-7-(2-C-methyl-β-D-ribofuranosyl)-7H-pyrrolo[2,3-d]pyrimidine,
6-amino-2-fluoro-9-(2-C-methyl-β-D-ribofuranosyl)purine,
2'-C-methyl-adenosine,
4-amino-7-[2-C-methyl-3-O-(1-oxo-octyl)-β-D-ribofuranosyl]-7H-pyrrolo[2,3-d]pyrimidine, and
4-amino-7-[2-C-methyl-3,5-di-O-(1-oxo-octyl)-β-D-ribofuranosyl]-7H-pyrrolo[2,3-d]pyrimidine;
and the corresponding 5'-triphosphates;

or a pharmaceutically acceptable salt thereof.

In a third embodiment of the methods of the present invention, the orthopoxvirus replication is selected from the group consisting of vaccinia virus replication, variola virus replication, cowpox virus replication, and monkeypox virus replication. In a class of this embodiment, the orthopoxvirus replication is vaccinia virus replication or variola virus replication.

In a fourth embodiment of the methods of the present invention, the orthopoxvirus infection is selected from the group consisting of vaccinia virus infection, variola virus infection, cowpox virus infection, and monkeypox virus infection. In a class of this embodiment, the orthopoxvirus infection is vaccinia virus infection or variola virus infection.

Another aspect of the present invention provides the novel nucleoside derivative, 6-amino-2-fluoro-9-(2-C-methyl-β-D-ribofuranosyl)purine or a pharmaceutically acceptable salt thereof.

Throughout the instant application, the following terms have the indicated meanings:

The alkyl groups specified above are intended to include those alkyl groups of the designated length in either a straight or branched configuration. Exemplary of such alkyl groups are methyl, ethyl, propyl, isopropyl, butyl, sec-butyl, tertiary butyl, pentyl, isopentyl, hexyl, isohexyl, and the like.

The term "alkenyl" shall mean straight or branched chain alkenes of two to six total carbon atoms, or any number within this range (e.g., ethenyl, propenyl, butenyl, pentenyl, etc.).

The term "alkynyl" shall mean straight or branched chain alkynes of two to six total carbon atoms, or any number within this range (e.g., ethynyl, propynyl, butynyl, pentynyl, etc.).

The term "cycloalkyl" shall mean cyclic rings of alkanes of three to eight total carbon atoms, or any number within this range (i.e., cyclopropyl, cyclobutyl, cyclopentyl, cyclohexyl, cycloheptyl, or cyclooctyl).

The term "alkoxy" refers to straight or branched chain alkoxides of the number of carbon atoms specified (e.g., $C_{1-4}$ alkoxy), or any number within this range [i.e., methoxy (MeO—), ethoxy, isopropoxy, etc.].

The term "alkylthio" refers to straight or branched chain alkylsulfides of the number of carbon atoms specified (e.g., $C_{1-4}$ alkylthio), or any number within this range [i.e., methylthio (MeS—), ethylthio, isopropylthio, etc.].

The term "alkylamino" refers to straight or branched alkylamines of the number of carbon atoms specified (e.g., $C_{1-4}$ alkylamino), or any number within this range [i.e., methylamino, ethylamino, isopropylamino, t-butylamino, etc.].

The term "alkylsulfonyl" refers to straight or branched chain alkylsulfones of the number of carbon atoms specified (e.g., $C_{1-6}$ alkylsulfonyl), or any number within this range [i.e., methylsulfonyl (MeSO$_2$—), ethylsulfonyl, isopropylsulfonyl, etc.].

The term "alkyloxycarbonyl" refers to straight or branched chain esters of a carboxylic acid derivative of the present invention of the number of carbon atoms specified (e.g., $C_{1-4}$ alkyloxycarbonyl), or any number within this range [i.e., methyloxycarbonyl (MeOCO—), ethyloxycarbonyl, or butyloxycarbonyl].

The term "alkyloxycarbonyloxy" refers to straight or branched chain alkyl carbonates of the present invention of the number of carbon atoms specified (e.g., $C_{1-10}$ alkyloxycarbonyloxy), or any number within this range [i.e., methyloxycarbonyloxy (MeOCOO—), ethyloxycarbonyloxy, or butyloxycarbonyloxy].

The term "alkylcarbonyloxy" refers to straight or branched chain alkanoic acid derivatives of alcohols of the present invention of the number of carbon atoms specified (e.g., $C_{1-16}$ alkylcarbonyloxy), or any number within this range [i.e., methylcarbonyloxy (MeCOO—), ethylcarbonyloxy, or n-octylcarbonyloxy].

The term "cycloalkylcarbonyloxy" refers to cyclic alkanoic acid derivatives of alcohols of the present invention of the number of carbon atoms specified (e.g., $C_{3-6}$ cycloalkylcarbonyloxy), or any number within this range [i.e., cyclopropylcarbonyloxy, cyclopentylcarbonyloxy, or cyclohexylcarbonyloxy].

The term "alkenylcarbonyloxy" refers to a straight or branched chain alkenoic acid derivatives of alcohols of the present invention having two to eighteen total carbon atoms and containing one to three double bonds in the alkene chain.

The term "aryl" includes both phenyl, naphthyl, and pyridyl. The aryl group is optionally substituted with one to three groups independently selected from $C_{1-4}$ alkyl, halogen, cyano, nitro, trifluoromethyl, $C_{1-4}$ alkoxy, and $C_{1-4}$ alkylthio.

The term "halogen" is intended to include the halogen atoms fluorine, chlorine, bromine and iodine.

The term "substituted" shall be deemed to include multiple degrees of substitution by a named substituent. Where multiple substituent moieties are disclosed or claimed, the substituted compound can be independently substituted by one or more of the disclosed or claimed substituent moieties, singly or plurally.

The term "5'-triphosphate" refers to a triphosphoric acid ester derivative of the 5'-hydroxyl group of a nucleoside compound of the present invention having the following general structural formula III:

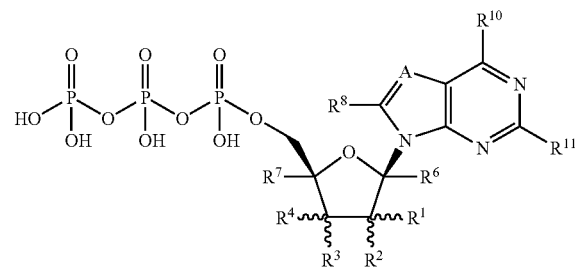

(III)

wherein $R^1$-$R^{11}$ are as defined above. The compounds of the present invention are also intended to include pharmaceutically acceptable salts of the triphosphate ester as well as pharmaceutically acceptable salts of 5'-monophosphate and 5'-diphosphate ester derivatives of the structural formulae IV and V, respectively,

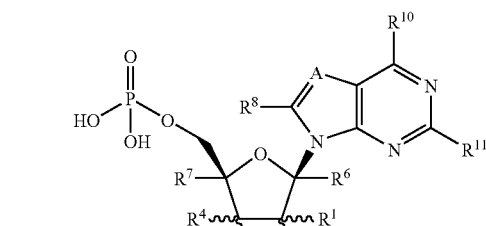

(IV)

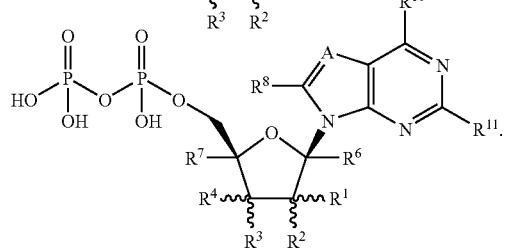

(V)

The term "5'-(S-acyl-2-thioethyl)phosphate" or "SATE" refers to a mono- or di-ester derivative of a 5'-monophosphate nucleoside derivative of the present invention of structural formulae VI and VII, respectively, as well as pharmaceutically acceptable salts of the mono-ester,

VI

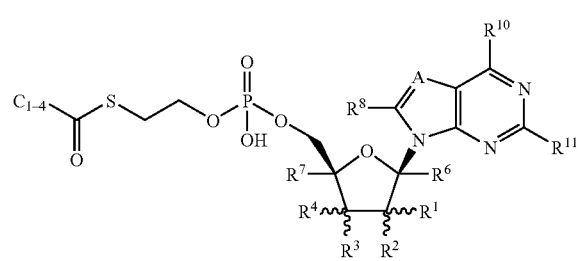

-continued

VII

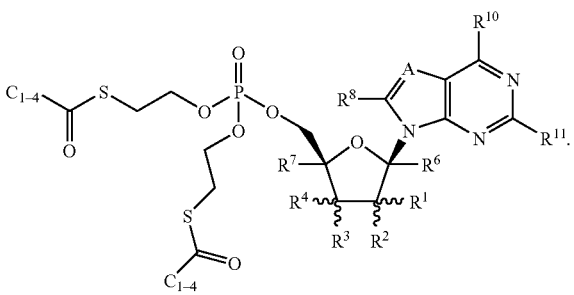

The term "composition", as in "pharmaceutical composition," is intended to encompass a product comprising the active ingredient(s) and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier.

The terms "administration of" and "administering a" compound should be understood to mean providing a compound of the invention or a prodrug of a compound of the invention to the individual in need.

Another aspect of the present invention is concerned with a method of treating orthopoxvirus infections with a compound of the present invention in combination with one or more agents useful for treating orthopoxvirus infections. Such agents active against orthopoxviruses include, but are not limited to, cidofovir, ribavirin, levovirin, and viramidine. Levovirin is the L-enantiomer of ribavirin which has shown immunomodulatory activity similar to ribavirin. Viramidine represents an analog of ribavirin disclosed in WO 01/60379 (assigned to ICN Pharmaceuticals). In accordance with this method of the present invention, the individual components of the combination can be administered separately at different times during the course of therapy or concurrently in divided or single combination forms. The instant invention is therefore to be understood as embracing all such regimes of simultaneous or alternating treatment, and the term "administering" is to be interpreted accordingly. It will be understood that the scope of combinations of the compounds of this invention with other agents useful for treating orthopoxvirus infection includes in principle any combination with any pharmaceutical composition for treating orthopoxvirus infection. When a compound of the present invention or a pharmaceutically acceptable salt thereof is used in combination with a second therapeutic agent active against orthopoxvirus, the dose of each compound may be either the same as or different from the dose when the compound is used alone.

Ribavirin, levovirin, and viramidine may exert their antiorthopoxvirus effects by modulating intracellular pools of guanine nucleotides via inhibition of the intracellular enzyme inosine monophosphate dehydrogenase (IMPDH). IMPDH is the rate-limiting enzyme on the biosynthetic route in de novo guanine nucleotide biosynthesis. Ribavirin is readily phosphorylated intracellularly and the monophosphate derivative is an inhibitor of IMPDH. Thus, inhibition of IMPDH represents another useful target for the discovery of inhibitors of orthopoxvirus replication. Therefore, the compounds of the present invention may also be administered in combination with an inhibitor of IMPDH, such as VX-497, which is disclosed in WO 97/41211 and WO 01/00622 (assigned to Vertex); another IMPDH inhibitor, such as that disclosed in WO 00/25780 (assigned to Bristol-Myers Squibb); or mycophenolate mofetil [see A. C. Allison and E. M. Eugui, *Agents Action,* 44 (Suppl.): 165 (1993)].

By "pharmaceutically acceptable" is meant that the carrier, diluent, or excipient must be compatible with the other ingredients of the formulation and not deleterious to the recipient thereof.

Also included within the present invention are pharmaceutical compositions comprising the nucleoside compounds and derivatives thereof of the present invention in association with a pharmaceutically acceptable carrier. Another example of the invention is a pharmaceutical composition made by combining any of the compounds described above and a pharmaceutically acceptable carrier. Another illustration of the invention is a process for making a pharmaceutical composition comprising combining any of the compounds described above and a pharmaceutically acceptable carrier.

Also included within the present invention are pharmaceutical compositions useful for inhibiting orthopoxvirus replication comprising an effective amount of a compound of the present invention and a pharmaceutically acceptable carrier. Pharmaceutical compositions useful for treating orthopoxvirus infection are also encompassed by the present invention. Additionally, the present invention is directed to a pharmaceutical composition comprising a therapeutically effective amount of a compound of the present invention in combination with a therapeutically effective amount of another agent active against orthopoxvirus. Agents active against orthopoxvirus include, but are not limited to, cidofovir, ribavirin, levovirin, and viramidine.

Another aspect of the present invention provides for the use of the nucleoside compounds and derivatives thereof and their pharmaceutical compositions for the manufacture of a medicament for the inhibition of orthopoxvirus replication, in particular vaccinia virus, variola virus replication, cowpox virus replication, and monkeypox virus replication and/or the treatment of orthopoxvirus infection, in particular vaccinia virus, variola virus infection, cowpox virus infection, and monkeypox virus infection. Yet a further aspect of the present invention provides for the nucleoside compounds and derivatives thereof and their pharmaceutical compositions for use as a medicament for the inhibition of orthopoxvirus replication, in particular vaccinia, variola, cowpox, and monkeypox virus replication, and/or for the treatment of orthopoxvirus infection, in particular vaccinia, variola, cowpox, and monkeypox virus infection.

The pharmaceutical compositions of the present invention comprise a compound of structural formula I as an active ingredient or a pharmaceutically acceptable salt thereof, and may also contain a pharmaceutically acceptable carrier and optionally other therapeutic ingredients.

The compositions include compositions suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

In practical use, the compounds of structural formula I can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets, with the solid oral preparations being preferred over the liquid preparations.

Because of their ease of administration, tablets and capsules represent the most advantageous oral dosage unit form in which case solid pharmaceutical carriers are obviously employed. If desired, tablets may be coated by standard aqueous or nonaqueous techniques. Such compositions and preparations should contain at least 0.1 percent of active compound. The percentage of active compound in these compositions may, of course, be varied and may conveniently be between about 2 percent to about 60 percent of the weight of the unit. The amount of active compound in such therapeutically useful compositions is such that an effective dosage will be obtained. The active compounds can also be administered intranasally as, for example, liquid drops or spray.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

Compounds of structural formula I may also be administered parenterally. Solutions or suspensions of these active compounds can be prepared in water suitably mixed with a surfactant such as hydroxy-propylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), suitable mixtures thereof, and vegetable oils.

Any suitable route of administration may be employed for providing a mammal, especially a human with an effective dosage of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like. Preferably compounds of structural formula I are administered orally.

For oral administration to humans, the dosage range is 0.01 to 1000 mg/kg body weight in divided doses. In one embodiment the dosage range is 0.1 to 100 mg/kg body weight in divided doses. In another embodiment the dosage range is 0.5 to 20 mg/kg body weight in divided doses. For oral administration, the compositions are preferably provided in the form of tablets or capsules containing 1.0 to 1000 milligrams of the active ingredient, particularly, 1, 5, 10, 15, 20, 25, 50, 75, 100, 150, 200, 250, 300, 400, 500, 600, 750, 800, 900, and 1000 milligrams of the active ingredient for the symptomatic adjustment of the dosage to the patient to be treated.

The effective dosage of active ingredient employed may vary depending on the particular compound employed, the mode of administration, the condition being treated and the severity of the condition being treated. Such dosage may be ascertained readily by a person skilled in the art. This dosage regimen may be adjusted to provide the optimal therapeutic response.

The compounds of the present invention contain one or more asymmetric centers and can thus occur as racemates and racemic mixtures, single enantiomers, diastereomeric mixtures and individual diastereomers. The present invention is meant to comprehend nucleoside compounds having the β-D stereochemical configuration for the five-membered furanose ring as depicted in the structural formula below, that is, nucleoside compounds in which the substituents at C-1 and C-4 of the five-membered furanose ring have the β-stereochemical configuration ("up" orientation as denoted by a bold line).

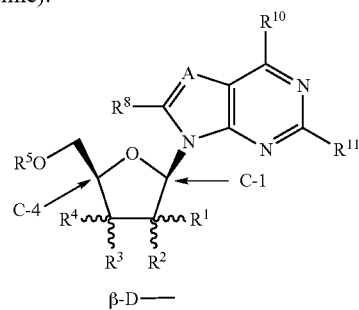

β-D——

Some of the compounds described herein contain olefinic double bonds, and unless specified otherwise, are meant to include both E and Z geometric isomers.

Some of the compounds described herein may exist as tautomers such as keto-enol tautomers. The individual tautomers as well as mixtures thereof are encompassed with compounds of structural formula I. An example of keto-enol tautomers which are intended to be encompassed within the compounds of the present invention is illustrated below:

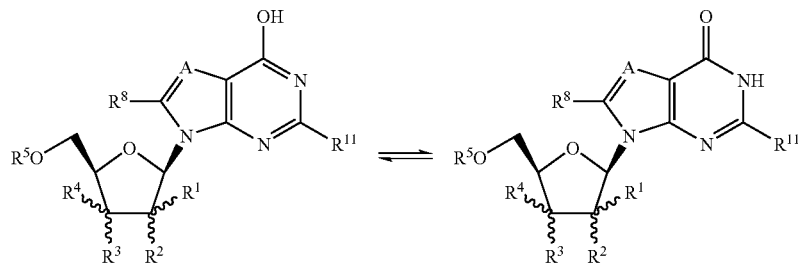

Compounds of structural formula I may be separated into their individual diastereoisomers by, for example, fractional crystallization from a suitable solvent, for example methanol or ethyl acetate or a mixture thereof, or via chiral chromatography using an optically active stationary phase.

Alternatively, any stereoisomer of a compound of the structural formula I may be obtained by stereospecific synthesis using optically pure starting materials or reagents of known configuration.

The stereochemistry of the substituents at the C-2 and C-3 positions of the furanose ring of the compounds of the present invention of structural formula I is denoted by squiggly lines which signifies that substituents $R^1$, $R^2$, $R^3$ and $R^4$ can have either the α (substituent "down") or β (substituent "up") configuration independently of one another. Notation of stereochemistry by a bold line as at C-1 and C-4 of the furanose ring signifies that the substituent has the β-configuration (substituent "up").

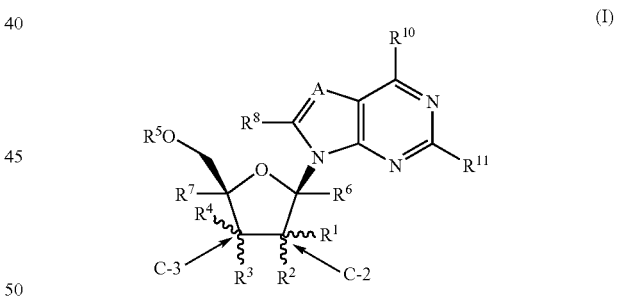

(I)

The compounds of the present invention may be administered in the form of a pharmaceutically acceptable salt. The term "pharmaceutically acceptable salt" refers to salts prepared from pharmaceutically acceptable non-toxic bases or acids including inorganic or organic bases and inorganic or organic acids. Salts of basic compounds encompassed within the term "pharmaceutically acceptable salt" refer to non-toxic salts of the compounds of this invention which are generally prepared by reacting the free base with a suitable organic or inorganic acid. Representative salts of basic compounds of the present invention include, but are not limited to, the following: acetate, benzenesulfonate, benzoate, bicarbonate, bisulfate, bitartrate, borate, bromide, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, oxalate, pamoate (embonate), palmitate, pantothenate, phosphate/diphosphate, polygalacturonate, salicylate, stearate, sulfate, subacetate, succinate, tannate, tartrate, teoclate; tosylate, triethiodide and valerate. Furthermore, where the compounds of the invention carry an acidic moiety, suitable pharmaceutically acceptable salts thereof include, but are not limited to, salts derived from inorganic bases including aluminum, ammonium, calcium, copper, ferric, ferrous, lithium, magnesium, manganic, mangamous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, cyclic amines, and basic ion-exchange resins, such as arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

Also, in the case of a carboxylic acid (—COOH) or alcohol group being present in the compounds of the present invention, pharmaceutically acceptable esters of carboxylic acid derivatives, such as methyl, ethyl, or pivaloyloxymethyl, or acyl derivatives of alcohols, such as acetate or maleate, can be employed. Included are those esters and acyl groups known in the art for modifying the solubility or hydrolysis characteristics for use as sustained-release or prodrug formulations.

Preparation of the Nucleoside Compounds and Derivatives of the Invention

The nucleoside compounds and derivatives thereof of the present invention can be prepared following synthetic methodologies well-established in the practice of nucleoside and nucleotide chemistry. Reference is made to the following text for a description of synthetic methods used in the preparation of the compounds of the present invention: "Chemistry of Nucleosides and Nucleotides," L. B. Townsend, ed., Vols. 1-3, Plenum Press, 1988, which is incorporated by reference herein in its entirety.

The synthesis of 9-(2'-C-methyl-β-D-ribofuranosyl)purines of structural formula VIII is described in U.S. Pat. No. 3,480,613, the contents of which are incorporated herein in their entirety.

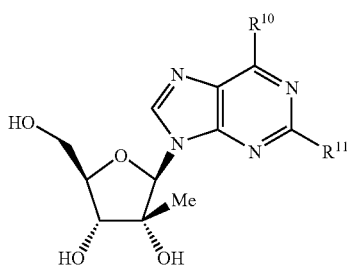

(VIII)

A representative general method for the preparation of compounds of the present invention is outlined in Scheme 1 below. This scheme illustrates the synthesis of compounds of the present invention of structural formula 1-7 wherein the furanose ring has the β-D-ribo configuration. The starting material is a 3,5-bis-O-protected alkyl furanoside, such as methyl furanoside, of structural formula 1-1. The C-2 hydroxyl group is then oxidized with a suitable oxidizing agent, such as a chromium trioxide or chromate reagent, Dess-Martin periodinane, or by Swern oxidation, to afford a C-2 ketone of structural formula 1-2. Addition of a Grignard reagent, such as an alkyl, alkenyl, or alkynyl magnesium halide (for example, MeMgBr, EtMgBr, vinylMgBr, allylMgBr, and ethynylMgBr) or an alkyl, alkenyl, or alkynyl lithium, such as MeLi, across the carbonyl double bond of 1-2 in a suitable organic solvent, such as tetrahydrofuran, diethyl ether, and the like, affords the C-2 tertiary alcohol of structural formula 1-3. A good leaving group (such as Cl, Br, and I) is next introduced at the C-1 (anomeric) position of the furanose sugar derivative by treatment of the furanoside of formula 1-3 with a hydrogen halide in a suitable organic solvent, such as hydrogen bromide in acetic acid, to afford the intermediate furanosyl halide 1-4. A C-1 sulfonate, such methanesulfonate (MeSO$_2$O—), trifluoromethane-sulfonate (CF$_3$SO$_2$O—), or p-toluenesulfonate (—OTs), may also serve as a useful leaving group in the subsequent reaction to generate the glycosidic (nucleosidic) linkage. The nucleosidic linkage is constructed by treatment of the intermediate of structural formula 1-4 with the metal salt (such as lithium, sodium, or potassium) of an appropriately substituted 1H-pyrrolo[2,3-d]pyrimidine 1-5, such as an appropriately substituted 4-halo-1H-pyrrolo[2,3-d]pyrimidine, which can be generated in situ by treatment with an alkali hydride (such as sodium hydride), an alkali hydroxide (such as potassium hydroxide), an alkali carbonate (such as potassium carbonate), or an alkali hexamethyldisilazide (such as NaHMDS) in a suitable anhydrous organic solvent, such as acetonitrile, tetrahydrofuran, 1-methyl-2-pyrrolidinone, or N,N-dimethylformamide DMF). The displacement reaction can be catalyzed by using a phase-transfer catalyst, such as TDA-1 or triethylbenzyl-ammonium chloride, in a two-phase system (solid-liquid or liquid-liquid). The optional protecting groups in the protected nucleoside of structural formula 1-6 are then cleaved following established deprotection methodologies, such as those described in T. W. Greene and P. G. M. Wuts, "Protective Groups in Organic Synthesis," 3$^{rd}$ ed., John Wiley & Sons, 1999. Optional introduction of an amino group at the 4-position of the pyrrolo[2,3-d]pyrimidine nucleus is effected by treatment of the 4-halo intermediate 1-6 with the appropriate amine, such as alcoholic ammonia or liquid ammonia, to generate a primary amine at the C-4 position (—NH$_2$), an alkylamine to generate a secondary amine (—NHR), or a dialkylamine to generate a tertiary amine (—NRR'). A 7H-pyrrolo[2,3-d]pyrimidin-4(3H)one compound may be derived by hydrolysis of 1-6 with aqueous base, such as aqueous sodium hydroxide. Alcoholysis (such as methanolysis) of 1-6 affords a C4 alkoxide (—OR), whereas treatment with an alkyl mercaptide affords a C4 alkylthio (—SR) derivative. Subsequent chemical manipulations well-known to practitioners of ordinary skill in the art of organic/medicinal chemistry may be required to attain the desired compounds of the present invention.

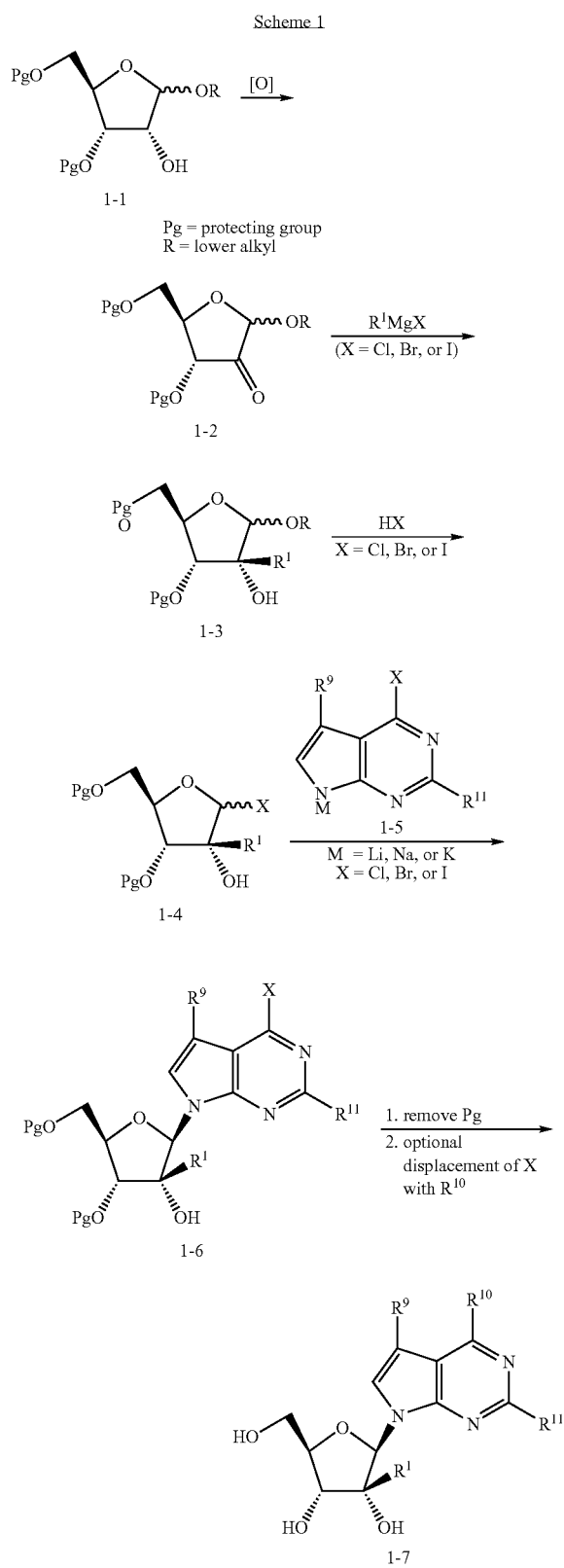

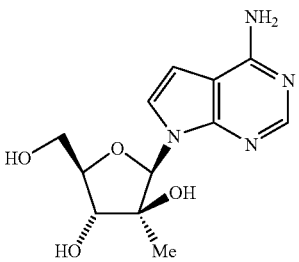

final compounds of the present invention. The nucleoside compounds of the present invention were prepared according to procedures detailed in the following examples. The examples are not intended to be limitations on the scope of the instant invention in any way, and they should not be so construed. Those skilled in the art of nucleoside and nucleotide synthesis will readily appreciate that known variations of the conditions and processes of the following preparative procedures can be used to prepare these and other compounds of the present invention. All temperatures are degrees Celsius unless otherwise noted.

EXAMPLE 1

4-Amino-7-(2-C-methyl-β-D-arabinofuranosyl)-7H-pyrrolo[2,3-d]pyrimidine

To chromium trioxide (1.57 g, 1.57 mmol) in dichloromethane (DCM) (10 mL) at 0° C. was added acetic anhydride (145 mg, 1.41 mmol) and then pyridine (245 mg, 3.10 mmol). The mixture was stirred for 15 min, then a solution of 7-[3,5-O-[1,1,3,3-tetrakis(1-methylethyl)-1,3-disiloxanediyl]-β-D-ribofuranosyl]-7H-pyrrolo[2,3-d]pyrimidin-4-amine [for preparation, see J. Am. Chem. Soc. 105: 4059 (1983)] (508 mg, 1.00 mmol) in DCM (3 mL) was added. The resulting solution was stirred for 2 h and then poured into ethyl acetate (10 mL), and subsequently filtered through silica gel using ethyl acetate as the eluent. The combined filtrates were evaporated in vacuo, taken up in diethyl ether/THF (1:1) (20 mL), cooled to −78° C. and methylmagnesium bromide (3M, in THF) (3.30 mL, 10 mmol) was added dropwise. The mixture was stirred at −78° C. for 10 min, then allowed to come to room temperature (rt) and quenched by addition of saturated aqueous ammonium chloride (10 mL) and extracted with DCM (20 mL). The organic phase was evaporated in vacuo and the crude product purified on silica gel using 5% methanol in dichloromethane as eluent. Fractions containing the product were pooled and evaporated in vacuo. The resulting oil was taken up in THF (5 mL) and tetrabutylammonium fluoride (TBAF) on silica (1.1 mmol/g on silica) (156 mg) was added. The mixture was stirred at room temperature for 30 min, filtered, and evaporated in vacuo. The crude product was purified on silica gel using 10% methanol in dichloromethane as eluent. Fractions containing the product were pooled and evaporated in vacuo to give the desired compound (49 mg) as a colorless solid.

$^1$H NMR (DMSO-$_6$): δ 1.08 (s, 3H), 3.67 (m, 2H), 3.74 (m, 1H), 3.83 (m, 1H), 5.19 (m, 1H), 5.23 (m, 1H), 5.48 (m, 1H), 6.08 (1H, s), 6.50 (m, 1H), 6.93 (bs, 2H), 7.33 (m, 1H), 8.02 (s, 1H).

The examples below provide citations to literature publications, which contain details for the preparation of final compounds or intermediates employed in the preparation of

EXAMPLE 2

4-Amino-7-(2-C-methyl-β-D-ribofuranosyl)-7H-pyrrolo[2,3-d]pyrimidine

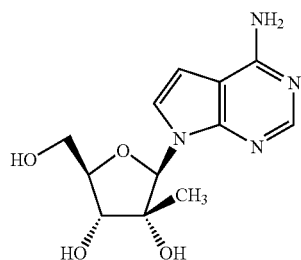

Step A: 3,5-Bis-O-(2,4-dichlorophenylmethyl)-1-O-methyl-α-D-ribofuranose

A mixture of 2-O-acetyl-3,5-bis-O-(2,4-dichlorophenylmethyl)-1-O-methyl-α-D-ribofuranose [for preparation, see: *Helv. Chim. Acta* 78: 486 (1995)] (52.4 g, 0.10 mol) in methanolic $K_2CO_3$ (500 mL, saturated at room temperature) was stirred at room temperature for 45 min and then concentrated under reduced pressure. The oily residue was suspended in $CH_2Cl_2$ (500 mL), washed with water (300 mL+5×200 mL) and brine (200 mL), dried ($Na_2SO_4$), filtered, and concentrated to give the title compound (49.0 g) as colorless oil, which was used without further purification in Step B below.

$^1$H NMR (DMSO-$d_6$): δ 3.28 (s, 3H, $OCH_3$), 3.53 (d, 2H, $J_{5,4}$=4.5 Hz, H-5a, H-5b), 3.72 (dd, 1H, $J_{3,4}$=3.6 Hz, $J_{3,2}$=6.6 Hz, H-3), 3.99 (ddd, 1H, $J_{2,1}$=4.5 Hz, $J_{2,OH-2}$=9.6 Hz, H-2), 4.07 (m, 1H, H-4), 4.50 (s, 2H, $CH_2Ph$), 4.52, 4.60 (2d, 2H, $J_{gem}$=13.6 Hz, $CH_2Ph$), 4.54 (d, 1H, OH-2), 4.75 (d, 1H, H-1), 7.32-7.45, 7.52-7.57 (2m, 10H, 2Ph). $^{13}$C NMR (DMSO-$d_6$): δ 55.40, 69.05, 69.74, 71.29, 72.02, 78.41, 81.45, 103.44, 127.83, 127.95, 129.05, 129.28, 131.27, 131.30, 133.22, 133.26, 133.55, 133.67, 135.45, 135.92.

Step B: 3,5-Bis-O-(2,4-dichlorophenylmethyl)-1-O-methyl-α-D-erythro-pentofuranos-2-ulose To an ice-cold suspension of Dess-Martin periodinane (50.0 g, 118 mmol) in anhydrous $CH_2Cl_2$ (350 mL) under argon (Ar) was added a solution of the compound from Step A (36.2 g, 75 mmol) in anhydrous $CH_2Cl_2$ (200 mL) dropwise over 0.5 h. The reaction mixture was stirred at 0° C. for 0.5 h and then at room temperature for 3 days. The mixture was diluted with anhydrous $Et_2O$ (600 mL) and poured into an ice-cold mixture of $Na_2S_2O_3.5H_2O$ (180 g) in saturated aqueous $NaHCO_3$ (1400 mL). The layers were separated, and the organic layer was washed with saturated aqueous $NaHCO_3$ (600 mL), water (800 mL) and brine (600 mL), dried ($MgSO_4$), filtered and evaporated to give the title compound (34.2 g) as a colorless oil, which was used without further purification in Step C below.

$^1$H NMR (CDCl$_3$): δ 3.50 (s, 3H, $OCH_3$), 3.79 (dd, 1H, $J_{5a,5b}$=11.3 Hz, $J_{5a,4}$=3.5 Hz, H-5a), 3.94 (dd, 1H, $J_{5b,4}$=2.3 Hz, H-5b), 4.20 (dd, 1H, $J_{3,1}$=1.3 Hz, $J_{3,4}$=8.4 Hz, H-3), 4.37 (ddd, 1H, H4), 4.58, 4.69 (2d, 2H, $J_{gem}$=13.0 Hz, $CH_2Ph$), 4.87 (d, 1H, H-1), 4.78, 5.03 (2d, 2H, $J_{gem}$=12.5 Hz, $CH_2Ph$), 7.19-7.26, 7.31-7.42 (2m, 10H, 2Ph). $^{13}$C NMR (DMSO-$d_6$): δ 55.72, 69.41, 69.81, 69.98, 77.49, 78.00, 98.54, 127.99, 128.06, 129.33, 129.38, 131.36, 131.72, 133.61, 133.63, 133.85, 133.97, 134.72, 135.32, 208.21.

Step C: 3,5-Bis-O-(2,4-dichlorophenylmethyl)-2-C-methyl-1-O-methyl-α-D-ribofuranose To a solution of MeMgBr in anhydrous $Et_2O$ (0.48 M, 300 mL) at −55° C. was added dropwise a solution of the compound from Step B (17.40 g, 36.2 mmol) in anhydrous $Et_2O$ (125 mL). The reaction mixture was allowed to warm to −30° C. and stirred for 7 h at −30° C. to −15° C., then poured into ice-cold water (500 mL) and the mixture vigorously stirred at room temperature for 0.5 h. The mixture was filtered through a Celite pad (10×5 cm) which was thoroughly washed with $Et_2O$. The organic layer was dried ($MgSO_4$), filtered and concentrated. The residue was dissolved in hexanes (~30 mL), applied onto a silica gel column (10×7 cm, prepacked in hexanes) and eluted with hexanes and hexanes/EtOAc (9/1) to give the title compound (16.7 g) as a colorless syrup.

$^1$H NMR (CDCl$_3$): δ 1.36 (d, 3H, $J_{Me,OH}$=0.9 Hz, 2C-Me), 3.33 (q, 1H, OH), 3.41 (d, 1H, $J_{3,4}$=3.3 Hz), 3.46 (s, 3H, $OCH_3$), 3.66 (d, 2H, $J_{5,4}$=3.7 Hz, H-5a, H-5b), 4.18 (apparent q, 1H, H-4), 4.52 (s, 1H, H-1), 4.60 (s, 2H, $CH_2Ph$), 4.63, 4.81 (2d, 2H, $J_{gem}$=13.2 Hz, $CH_2Ph$), 7.19-7.26, 7.34-7.43 (2m, 10H, 2Ph). $^{13}$C NMR (CDCl$_3$): δ 24.88, 55.45, 69.95, 70.24, 70.88, 77.06, 82.18, 83.01, 107.63, 127.32, 129.36, 130.01, 130.32, 133.68, 133.78, 134.13, 134.18, 134.45, 134.58.

Step D: 4-Chloro-7-[3,5-bis-O-(2,4-dichlorophenylmethyl)-2-C-methyl-β-D-ribofuranosyl]-7H-pyrrolo[2,3-d]pyrimidine To a solution of the compound from Step C (9.42 g, 19 mmol) in anhydrous dichloromethane (285 mL) at 0° C. was added HBr (5.7 M in acetic acid, 20 mL, 114 mmol) dropwise. The resulting solution was stirred at 0° C. for 1 h and then at room temperature for 3 h, evaporated in vacuo and co-evaporated with anhydrous toluene (3×40 mL). The oily residue was dissolved in anhydrous acetonitrile (50 mL) and added to a solution of the sodium salt of 4-chloro-1H-pyrrolo[2,3-d]pyrimidine in acetonitrile [generated in situ from 4-chloro-1H-pyrrolo[2,3-d]pyrimidine [for preparation, see *J. Chem. Soc.*, 131 (1960)] (8.76 g, 57 mmol) in anhydrous acetonitrile (1000 mL), and NaH (60% in mineral oil, 2.28 g, 57 mmol), after 4 h of vigorous stirring at room temperature]. The combined mixture was stirred at room temperature for 24 h, and then evaporated to dryness. The residue was suspended in water (250 mL) and extracted with EtOAc (2×500 mL). The combined extracts were washed with brine (300 mL, dried over $Na_2SO_4$, filtered and evaporated. The crude product was purified on a silica gel column (10 cm×10 cm) using ethyl acetate/hexane (1:3 and 1:2) as the eluent. Fractions containing the product were combined and evaporated in vacuo to give the desired product (5.05 g) as a colorless foam.

$^1$H NMR (CDCl$_3$): δ 0.93 (s, 3H, $CH_3$), 3.09 (s, 1H, OH), 3.78 (dd, 1H, $J_{5',5''}$=10.9 Hz, $J_{5',4}$=2.5 Hz, H-5'), 3.99 (dd, 1H, $J_{5'',4}$=2.2 Hz, H-5''), 4.23-4.34 (m, 2H, H-3', H-4'), 4.63, 4.70 (2d, 2H, $J_{gem}$=12.7 Hz, $CH_2Ph$), 4.71, 4.80 (2d, 2H, $J_{gem}$=12.1 Hz, $CH_2Ph$), 6.54 (d, 1H, $J_{5,6}$=3.8 Hz, H-5), 7.23-7.44 (m, 10H, 2Ph). $^{13}$C NMR (CDCl$_3$): δ 21.31, 69.10, 70.41, 70.77, 79.56, 80.41, 81.05, 91.11, 100.57, 118.21, 127.04, 127.46, 127.57, 129.73, 129.77, 130.57, 130.99, 133.51, 133.99, 134.33, 134.38, 134.74, 135.21, 151.07, 151.15, 152.47.

Step E: 4-Chloro-7-(2-C-methyl-β-D-ribofuranosyl)-7H-pyrrolo[2,3-d]pyrimidine

To a solution of the compound from Step D (5.42 g, 8.8 mmol) in dichloromethane (175 mL) at −78° C. was added boron trichloride (1M in dichloromethane, 88 mL, 88 mmol)

dropwise. The mixture was stirred at −78° C. for 2.5 h, then at −30° C. to −20° C. for 3 h. The reaction was quenched by addition of methanol/dichloromethane (1:1) (90 mL) and the resulting mixture stirred at −15° C. for 30 min, then neutralized with aqueous ammonia at 0° C. and stirred at room temperature for 15 min. The solid was filtered and washed with $CH_2Cl_2$/MeOH (1/1, 250 mL). The combined filtrate was evaporated, and the residue was purified by flash chromatography over silica gel using $CH_2Cl_2$ and $CH_2Cl_2$:MeOH (99:1, 98:2, 95:5 and 90:10) gradient as the eluent to furnish desired compound (1.73 g) as a colorless foam, which turned into an amorphous solid after treatment with MeCN.

$^1$H NMR (DMSO-$d_6$): δ 0.64 (s, 3H, $CH_3$), 3.61-3.71 (m, 1H, H-5'), 3.79-3.88 (m, 1H, H-5"), 3.89-4.01 (m, 2H, H-3', H-4'), 5.15-5.23 (m, 3H, 2'-OH, 3'-OH, 5'-OH), 6.24 (s, 1H, H-1'), 6.72 (d, 1H, $J_{5,6}$=3.8 Hz, H-5), 8.13 (d, 1H, H-6), 8.65 (s, 1H, H-2). $^{13}$C NMR (DMSO-$d_6$): δ 20.20, 59.95, 72.29, 79.37, 83.16, 91.53, 100.17, 117.63, 128.86, 151.13, 151.19, 151.45.

Step F: 4-Amino-7-(2-C-methyl-β-D-ribofuranosyl)-7H-pyrrolo[2,3-d]pyrimidine

To the compound from Step E (1.54 g, 5.1 mmol) was added methanolic ammonia (saturated at 0° C.; 150 mL). The mixture was heated in a stainless steel autoclave at 85° C. for 14 h, then cooled and evaporated in vacuo. The crude mixture was purified on a silica gel column with $CH_2Cl_2$/MeOH (9/1) as eluent to give the title compound as a colorless foam (0.8 g), which separated as an amorphous solid after treatment with MeCN. The amorphous solid was recrystallized from methanol/acetonitrile; m.p. 222° C.

$^1$H NMR (DMSO-$d_6$): δ 0.62 (s, 3H, $CH_3$), 3.57-3.67 (m, 1H, H-5'), 3.75-3.97 (m, 3H, H-5", H-4', H-3'), 5.00 (s, 1H, 2'-OH), 5.04 (d, 1H, $J_{3'OH,3'}$=6.8 Hz, 3'-OH), 5.06 (t, 1H, $J_{5'OH,5',5''}$=5.1 Hz, 5'-OH), 6.11 (s, 1H, H-1'), 6.54 (d, 1H, $J_{5,6}$=3.6 Hz, H-5), 6.97 (br s, 2H, $NH_2$), 7.44 (d, 1H, H-6), 8.02 (s, 1H, H-2). $^{13}$C NMR (DMSO-$d_6$): δ 20.26, 60.42, 72.72, 79.30, 82.75, 91.20, 100.13, 103.08, 121.96, 150.37, 152.33, 158.15. LC-MS: Found: 279.10 (M−H$^+$); calc. for $C_{12}H_{16}N_4O_4$+H$^+$: 279.11.

EXAMPLE 3

4-Amino-7-(2-C-ethyl-β-D-ribofuranosyl-7H-pyrrolo[2,3-d]pyrimidine

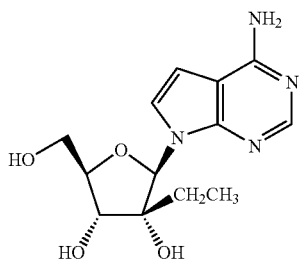

Step A: 3,5-Bis-O-(2,4-dichlorophenylmethyl)-2-C-ethyl-1-O-methyl-α-D-ribofuranose To diethyl ether (300 mL) at −78° C. was slowly added EtMgBr (3.0 M, 16.6 mL) and then dropwise the compound from Step B of Example 2 (4.80 g, 10.0 mmol) in anhydrous $Et_2O$ (100 mL). The reaction mixture was stirred at −78° C. for 15 min, allowed to warm to −15° C. and stirred for another 2 h, and then poured into a stirred mixture of water (300 mL) and $Et_2O$ (600 mL). The organic phase was separated, dried ($MgSO_4$), and evaporated in vacuo. The crude product was purified on silica gel using ethyl acetate/hexane (1:2) as eluent. Fractions containing the product were pooled and evaporated in vacuo to give the desired product (3.87 g) as a colorless oil.

Step B: 4-Chloro-7-[3,5-bis-O-(2,4-dichlorophenylmethyl)-2-C-ethyl-β-D-ribofuranosyl]-7H-pyrrolo[2,3-d]pyrimidine To a solution of the compound from Step A (1.02 mg, 2.0 mmol) in dichloromethane (40 mL) was added HBr (5.7 M in acetic acid) (1.75 mL, 10.0 mmol) dropwise at 0° C. The resulting solution was stirred at room temperature for 2 h, evaporated in vacuo and co-evaporated twice from toluene (10 mL). The oily residue was dissolved in acetonitrile (10 mL) and added to a vigorously stirred mixture of 4-chloro-1H-pyrrolo[2,3-d]pyrimidine (307 mg, 2.0 mmol), potassium hydroxide (337 mg, 6.0 mmol) and tris[2-(2-methoxyethoxy)ethyl]amine (130 mg, 0.4 mmol) in acetonitrile (10 mL). The resulting mixture was stirred at room temperature overnight, and then poured into a stirred mixture of saturated ammonium chloride (100 mL) and ethyl acetate (100 mL). The organic layer was separated, washed with brine (100 mL), dried over $MgSO_4$, filtered and evaporated in vacuo. The crude product was purified on silica gel using ethyl acetate/hexane (1:2) as eluent to give the desired product (307 mg) as a colorless foam.

Step C: 4-Chloro-7-(2-C-ethyl-β-D-ribofuranosyl-7H-pyrrolo[2,3-d]pyrimidine

To a solution of the compound from Step B (307 mg, 0.45 mmol) in dichloromethane (8 mL) was added boron trichloride (1M in dichloromethane) (4.50 mL, 4.50 mmol) at −78° C. The mixture was stirred at −78° C. for 1 h, then at −10° C. for 3 h. The reaction was quenched by addition of methanol/dichloromethane (1:1) (10 mL), stirred at −15° C. for 30 min, and neutralized by addition of aqueous ammonium hydroxide. The mixture was evaporated under diminished pressure and the resulting oil purified on silica gel using methanol/dichloromethane (1:9) as eluent. Fractions containing the product were pooled and evaporated in vacuo to give the desired product (112 mg) as a colorless foam.

Step D: 4-Amino-7-(2-C-ethyl-β-D-ribofuranosyl)-7H-pyrrolo[2,3-d]pyrimidine

To the compound from Step C (50 mg, 0.16 mmol) was added saturated ammonia in methanol (4 mL). The mixture was stirred at 75° C. for 72 h in a closed container, cooled and evaporated in vacuo. The crude mixture was purified on silica gel using methanol/dichloromethane (1:9) as eluent. Fractions containing the product were pooled and evaporated in vacuo to give the desired product (29 mg) as a colorless powder.

$^1$HNMR (200 MHz, DMSO-$d_6$): δ 0.52 (t, 3H), 1.02 (m, 2H), 4.01-3.24 (m, 6H), 5.06 (m, 1H), 6.01 (s, 1H), 6.51 (d, 1H), 6.95 (s br, 2H), 6.70 (d, 1H), 7.99 (s, 1H). LC-MS: Found: 295.2 (M+H$^+$); calc. for $C_{13}H_{18}N_4O_4$+H$^+$: 295.14.

EXAMPLE 4

2-Amino-7-(2-C-methyl-β-D-ribofuranosyl)-7H-pyrrolo[2,3-d]pyrimidin-4(3H)-one

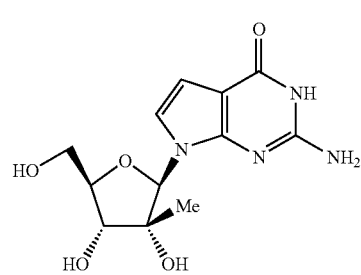

Step A: 2-Amino-4-chloro-7-[3,5-bis-O-(2,4-dichlorophenylmethyl)-2-C-methyl-β-D-ribofuranosyl)-7H-pyrrolo[2,3-d]pyrimidine To an ice-cold solution of the product from Step C of Example 2 (1.27 g, 2.57 mmol) in $CH_2Cl_2$ (30 mL) was added HBr (5.7 M in acetic acid; 3 mL) dropwise. The reaction mixture was stirred at room temperature for 2 h, concentrated under diminished pressure and coevaporated with toluene (2×15 mL). The resulting oil was dissolved in acetonitrile (MeCN) (15 mL) and added dropwise into a well-stirred mixture of 2-amino-4-chloro-7H-pyrrolo[2,3-d]pyrimidine [for preparation, see *Heterocycles* 35: 825 (1993)] (433 mg, 2.57 mmol), KOH (85%, powdered) (0.51 g, 7.7 mmol), tris-[2-(2-methoxyethoxy)ethyl]amine (165 μL, 0.51 mmol) in acetonitrile (30 mL). The resulting mixture was stirred at room temperature for 1 h, filtered and evaporated. The residue was purified on a silica gel column using hexanes/EtOAc, 5/1, 3/1 and 2/1, as eluent to give the title compound as a colorless foam (0.65 g).

Step B: 2-Amino-4-chloro-7-(2-C-methyl-β-D-ribofuranosyl)-7H-pyrrolo[2,3-d]pyrimidine To a solution of the product from Step A (630 mg, 1.0 mmol) in $CH_2Cl_2$ (20 mL) at −78° C. was added boron trichloride (1M in $CH_2Cl_2$) (10 mL, 10 mmol). The mixture was stirred at −78° C. for 2 h, then at −20° C. for 2.5 h. The reaction was quenched with $CH_2Cl_2$/MeOH (1:1) (10 mL), stirred at −20° C. for 0.5 h, and neutralized at 0° C. with aqueous ammonia. The solid was filtered, washed with $CH_2Cl_2$/MeOH (1:1) and the combined filtrate evaporated in vacuo. The residue was purified on a silica gel column with $CH_2Cl_2$/MeOH, 50/1 and 20/1, as eluent to give the title compound as a colorless foam (250 mg).

Step C: 2-Amino-7-(2-C-methyl-β-D-ribofuranosyl)-7H-pyrrolo[2,3-d]pyrimidin-4(3H)-one A mixture of the product from Step B (90 mg, 0.3 mmol) in aqueous NaOH (2N, 9 mL) was heated at reflux temperature for 5 h, then neutralized at 0° C. with 2 N aqueous HCl and evaporated to dryness. Purification on a silica gel column with $CH_2Cl_2$/MeOH, 5/1, as eluent afforded the title compound as a white solid (70 mg).

$^1$H NMR (200 MD, $CD_3OD$): δ 0.86 (s, 3H), 3.79 (m, 1H), 3.90-4.05 (m, 3H), 6.06 (s, 1H), 6.42 (d, J=3.7 Hz, 1H), 7.05 (d, J=3.7 Hz, 1H).

EXAMPLE 5

2-Amino-4-cyclopropylamino-7-(2-C-methyl-β-D-ribofuranosyl)-7H-pyrrolo-[2,3-d]pyrimidine

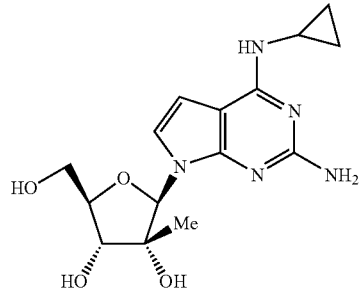

A solution of 2-amino-4-chloro-7-(2-C-methyl-β-D-ribofuranosyl)-7H-pyrrolo[2,3-d]pyrimidine (Example 4, Step B) (21 mg, 0.07 mmol) in cyclopropylamine (0.5 mL) was heated at 70° C. for two days, then evaporated to an oily residue and purified on a silica gel column with $CH_2Cl_2$/MeOH, 20/1, as eluent to give the title compound as a white solid (17 mg).

$^1$H NMR (200 MHz, $CD_3CN$): δ 0.61 (m, 2H), 0.81 (m, 2H), 0.85 (s, 3H), 2.83 (m, 1H), 3.74-3.86 (m, 1H), 3.93-4.03 (m, 2H), 4.11 (d, J=8.9 Hz, 1H), 6.02 (s, 1H), 6.49 (d, J=3.7 Hz, 1H), 7.00 (d, J=3.7 Hz, 1H).

EXAMPLE 6

4-Amino-7-(2-C-methyl-β-D-ribofuranosyl)-7H-pyrrolo[2,3-d]pyrimidine-5-carbonitrile

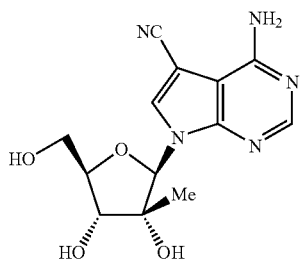

This compound was prepared following procedures described by Y. Murai et al. in *Heterocycles* 33: 391-404 (1992).

EXAMPLE 7

4-Amino-7-(2-C-methyl-β-D-ribofuranosyl)-7H-pyrrolo[2,3-d]pyrimidine-5-carboxamide

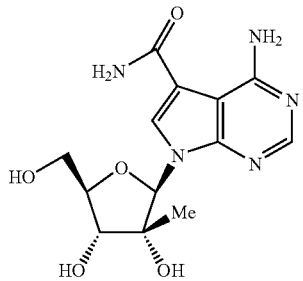

This compound was prepared following procedures described by Y. Murai et al. in *Heterocycles* 33: 391-404 (1992).

EXAMPLE 8

General Process to SATE Prodrug Moiety

S-Acyl-2-thioethyl (SATE) pronucleotides are discussed in C. R. Wagner, V. V. Iyer, and E. J. McIntee, "Pronucleotides: Toward the In Vivo Delivery of Antiviral and Anticancer Nucleotides," *Med. Res. Rev.*, 20: 1-35 (2000), which is incorporated by reference herein in its entirety. SATE derivatives of nucleosides are also disclosed U.S. Pat. Nos. 5,770,725; 5,849,905; and 6,020,482, the contents of each of which are incorporated by reference herein in their entirety.

Bis(S-acetyl-2-thioethyl)-N,N-diisopropylphosphoramidite

2-Mercaptoethanol (5 g, 64 mmol) was dissolved in $CH_2Cl_2$ (50 mL). To this solution was added triethylamine (7.67 mL, 57.6 mmol), and the reaction mixture was cooled in an ice bath to 0° C. Acetic anhydride (4.54 mL, 48 mmol) was added dropwise in 10 min, and the reaction mixture was stirred for 1 h at 0° C. The reaction mixture was then allowed to come to room temperature over a period of 2 h. The reaction mixture was diluted with $CH_2Cl_2$ (50 mL), washed with water (75 mL), 5% aqueous $NaHCO_3$ (75 mL) and brine (75 mL). The organic phase was dried over anhydrous $Na_2SO_4$ and concentrated in vacuo to give an oil. The oil was then dissolved in anhydrous THF (40 mL) and anhydrous triethylamine (7.76 mL) was added. To this mixture was added activated molecular sieves (4Å) and was kept at room temperature for 10 min. The reaction mixture was cooled in an ice bath to 0° C. and diisopropylphosphoramidous dichloride (6.47 g, 32.03 mmol) was added. The reaction mixture was stirred at 0° C. for 2 h under inert atmosphere. Hexane (40 mL) was added to the reaction mixture and the precipitate formed was filtered. The filtrate was concentrated to one fourth of the volume, purified by loaded silica gel column chromatography and eluted with hexane containing 3% triethylamine and incremental amount of ethyl acetate (0 to 7%) to give the title compound as an oil (2.36 g).

$^1$H NMR (CDCl$_3$): δ 1.17 (s, 6H), 1.21 (s, 6H), 2.36 (s, 6H), 3.14 (t, J=6.44 Hz), 3.51-3.84 (m, 6H); $^{13}$C NMR (CDCl$_3$): δ 24.47, 24.61, 30.48, 42.85, 43.1, 61.88, 62.23, 195.26; $^{13}$P NMR (CDCl$_3$): δ 146.96.

EXAMPLE 9

5'-Triphosphate Derivatives

The nucleoside 5'-triphosphates of the present invention were prepared following general procedures described in *Chem. Rev.* 100: 2047 (2000).

EXAMPLE 10

Purification and Purity Analysis of 5'-Triphosphate Derivatives

The triphosphate derivatives were purified by anion exchange (AX) chromatography using a 30×100 mm Mono Q column (Pharmacia) with a buffer system of 50 mM Tris, pH 8. Elution gradients were typically from 40 mM NaCl to 0.8 M NaCl in two column volumes at 6.5 mL/min. Appropriate fractions from anion exchange chromatography were collected and desalted by reverse-phase (RP) chromatography using a Luna C18 250×21 mm column (Phenomenex) with a flow rate of 10 mL/min. Elution gradients were generally from 1% to 95% methanol in 14 min at a constant concentration of 5 mM triethylammonium acetate (TEAA).

Mass spectra of the purified triphosphates were determined using on-line HPLC mass spectrometry on a Hewlett-Packard (Palo Alto, Calif.) MSD 1100. A Phenomenex Luna (C18(2)), 150×2 mm, plus 30×2 mm guard column, 3-µm particle size was used for RP HPLC. A 0 to 50% linear gradient (15 min) of acetonitrile in 20 mM TEAA (triethylammonium acetate) pH 7 was performed in series with mass spectral detection in the negative ionization mode. Nitrogen gas and a pneumatic nebulizer were used to generate the electrospray. The mass range of 150-900 was sampled. Molecular masses were determined using the HP Chemstation analysis package.

The purity of the purified triphosphates was determined by analytical RP and AX HPLC. RP HPLC with a Phenomenex Luna or Jupiter column (250×4.6 mm), 5-µm particle size was typically run with a 2-70% acetonitrile gradient in 15 min in 100 mM TEAA, pH 7. AX HPLC was performed on a 1.6×5 mm Mono Q column (Pharmacia). Triphosphates were eluted with a gradient of 0 to 0.4 M NaCl at constant concentration of 50 mM Tris, pH 8. The purity of the triphosphates was generally >80%.

EXAMPLE 11

5'-Monophosphate Derivatives

The nucleoside 5'-monophosphates of the present invention were prepared following the general procedures described in *Tetrahedron Lett.* 50: 5065 (1967).

EXAMPLE 12

Mass Spectral Characterization of 5'-Triphosphate Derivatives

Mass spectra of 5'-triphosphates of the compounds of the present invention were determined as described in Example 10. Listed in the following table are the calculated and experimental masses for representative 5'-triphosphates prepared according to the procedures of Example 9. The example numbers correspond to the parent compound of the 5'-triphosphate.

| Example | Calculated | Found |
| --- | --- | --- |
| 1 | 520.0 | 519.9 |
| 2 | 520.0 | 520.0 |
| 3 | 534.0 | 534.0 |
| 4 | 536.0 | 536.0 |

EXAMPLE 13

[4-Amino-7-(2-C-methyl-β-D-ribofuranosyl)-7H-pyrrolo[2,3-d]-pyrimidine]-5'-monophosphate

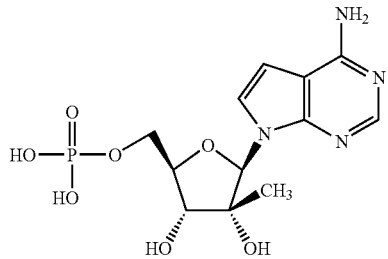

To the compound from Step F of Example 2 (14 mg, 0.05 mmol) (dried by coevaporation with pyridine and several times with toluene) was added trimethyl phosphate (0.5 mL). The mixture was stirred overnight in a sealed container. It was then cooled to 0° C. and phosphorous oxychloride (0.0070 mL, 0.075 mmol) was added via a syringe. The mixture was stirred for 3 h at 0° C., then the reaction was quenched by addition of tetraethylammonium bicarbonate (TEAB) (1M) (0.5 mL) and water (5 mL). The reaction mixture was purified and analyzed according to the procedure described in Example 10.

Electron spray mass spectrum (ES-MS): Found: 359.2 (M–H$^+$), calc. for $C_{12}H_{17}N_4O_7P$–H$^+$: 359.1.

EXAMPLE 14

[4-Amino-7-(2-C-methyl-β-D-ribofuranosyl)-7H-pyrrolo[2,3-d]-pyrimidine]-5'-diphosphate

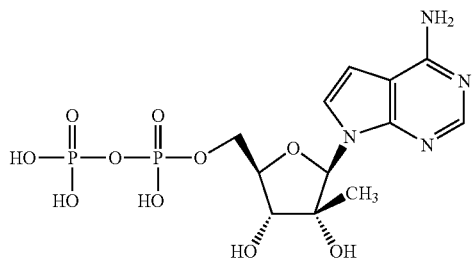

To the compound from Step F of Example 2 (56 mg, 0.20 mmol) (dried by coevaporation with pyridine and several times with toluene) was added trimethyl phosphate (stored over sieves) (1.0 mL). The mixture was stirred overnight in a sealed container. It was then cooled to 0° C. and phosphorous oxychloride (0.023 mL, 0.25 mmol) was added via a syringe. The mixture was stirred for 2 h at 0° C., then tributylamine (0.238 mL, 1.00 mmol) and tributylammonium phosphate (generated from phosphoric acid and tributylamine in pyridine, followed by repeated azeotropic evaporation with pyridine and acetonitrile) (1.0 mmol in 3.30 mL acetonitrile) was added. The mixture was stirred for an additional 30 min at 0° C., the sealed vial was then opened and the reaction quenched by addition of TEAB (1M) (1.0 mL) and water (5 mL). The reaction mixture was purified and analyzed according to the procedure described in Example 10.

ES-MS: Found: 439.0 (M–H$^+$), calc. for $C_{12}H_{18}N_4O_{10}P_2$–H$^+$: 439.04.

EXAMPLE 15

[4-Amino-7-(2-C-methyl-β-D-ribofuranosyl)-7H-pyrrolo[2,3-d]-pyrimidine]-5'-triphosphate

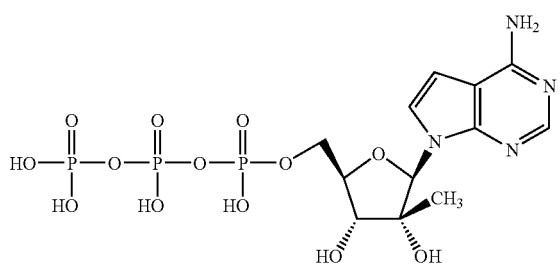

To the compound from Step F of Example 2 (20 mg, 0.07 mmol) (dried by coevaporation with pyridine and several times with toluene) was added trimethyl phosphate (stored over sieves) (0.4 mL). The mixture was stirred overnight in a sealed container. It was then cooled to 0° C. and phosphorous oxychloride (0.0070 mL, 0.075 mmol) was added via syringe. The mixture was stirred for 3 h at 0° C., then tributylamine (0.083 mL, 0.35 mmol), tributylammonium pyrophosphate (127 mg, 0.35 mmol) and acetonitrile (stored over sieves) (0.25 mL) were added. The mixture was stirred for an additional 30 min at 0° C., the sealed vial was then opened and the reaction. quenched by addition of TEAB (1M) (0.5 mL) and water (5 mL). The reaction mixture was purified and analyzed according to the procedure described in Example 10.

ES-MS: Found: 519.0 (M–H$^+$), calc. for $C_{12}H_{19}N_4O_{13}P_3$–H$^+$: 519.01.

EXAMPLE 16

7-(2-C-methyl-β-D-ribofuranosyl)-7H-pyrrolo[2,3-d]pyrimidin-4(3H)-one

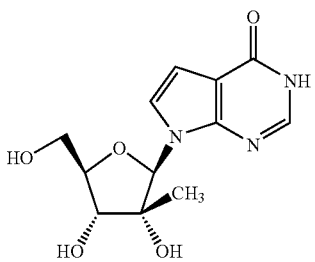

To the compound from Step E of Example 2 (59 mg, 0.18 mmol) was added aqueous sodium hydroxide (1M). The mixture was heated to reflux for 1 hr, cooled, neutralized with aqueous HCl (2M) and evaporated in vacuo. The residue was purified on silica gel using dichloromethane/methanol (4:1) as eluent. Fractions containing the product were pooled and evaporated in vacuo to give the desired product (53 mg) as a colorless oil.

$^1$H NMR (CD$_3$CN): δ 0.70 (s, 3H), 3.34-4.15 (overlapping m, 7H), 6.16 (s, 1H), 6.57 (d, 3.6 Hz, 1H), 7.37 (d, 3.6 Hz, 1H), 8.83 (s, 1H).

EXAMPLE 17

4-Amino-5-chloro-7-(2-C-methyl-β-D-ribofuranosyl)-7H-pyrrolo[2,3-d]pyrimidine

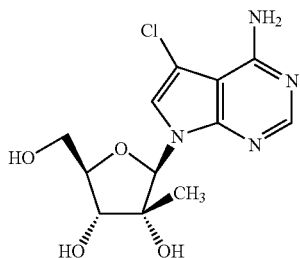

To a pre-cooled solution (0° C.) of the compound from Step F of Example 2 (140 mg, 0.50 mmol) in DMF (2.5 mL) was added N-chlorosuccinimide (0.075 g, 0.55 mmol) in DMF (0.5 mL) dropwise. The solution was stirred at room temperature for 1 h and the reaction quenched by addition of methanol (4 mL) and evaporated in vacuo. The crude product was purified on silica gel using methanol/dichloromethane (1:9) as eluent. Fractions containing the product were pooled and evaporated in vacuo to give the desired product (55 mg) as a colorless solid.

$^1$H NMR (CD$_3$CN): δ 0.80 (s, 3H), 3.65-4.14 (overlapping m, 7H), 5.97 (s br, 2H), 6.17 (s, 1H), 7.51 (s, 1H), 8.16 (s, 1H). ES-MS: Found: 315.0 (M+H$^+$), calc. for C$_{12}$H$_{15}$ClN$_4$O$_4$+H$^+$: 315.09.

EXAMPLE 18

4-Amino-5-bromo-7-(2-C-methyl-β-D-ribofuranosyl)-7H-pyrrolo[2,3-d]pyrimidine

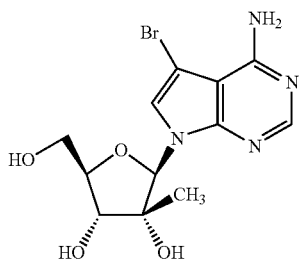

To a pre-cooled solution (0° C.) of the compound from Step F of Example 2 (28 mg, 0.10 mmol) in DMF (0.5 mL) was added N-bromosuccinimide (0.018 g, 0.10 mmol) in DMF (0.5 mL) dropwise. The solution was stirred at 0° C. for 20 min, then at room temperature for 10 min. The reaction was quenched by addition of methanol (4 mL) and evaporated in vacuo. The crude product was purified on silica gel using methanol/dichloromethane (1:9) as eluent. Fractions containing the product were pooled and evaporated in vacuo to give the desired product (13.0 mg) as a colorless solid.

$^1$H NMR (CD$_3$CN): δ 0.69 (s, 3H), 3.46-4.00 (overlapping m, 7H), 5.83 (s br, 2H), 6.06 (s, 1H), 7.45 (s, 1H), 8.05 (s, 1H). ES-MS: Found: 359.1 (M+H$^+$), calc. for C$_{12}$H$_{15}$BrN$_4$O$_4$+H$^+$: 359.04.

EXAMPLE 19

2-Amino-7-(2-C-methyl-β-D-ribofuranosyl)-7H-pyrrolo[2,3-d]pyrimidine

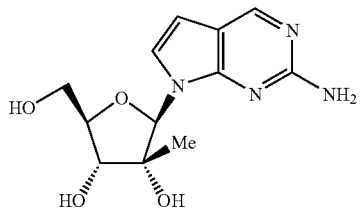

A mixture of 2-amino-4-chloro-7-(2-C-methyl-β-D-ribofuranosyl)-7H-pyrrolo[2,3-d]pyrimidine (Example 4, Step B) (20 mg, 0.07 mmol) in EtOH (1.0 mL), pyridine (0.1 mL) and 10% Pd/C (6 mg) under H$_2$ (atmospheric pressure) was stirred overnight at room temperature. The mixture was filtered through a Celite pad which was thorougly washed with EtOH. The combined filtrate was evaporated and purified on a silica gel column with CH$_2$Cl$_2$/MeOH, 20/1 and 10/1, as eluent to give the title compound as a white solid (16 mg).

$^1$H NMR (200 MHz, CD$_3$OD): δ 0.86 (s, 3H, 2'C-Me), 3.82 (dd, J$_{5',4'}$=3.6 Hz, J$_{5',5''}$=12.7 Hz, 1H, H-5'), 3.94-4.03 (m, 2H, H-5', H-4'), 4.10 (d, J$_{3',4'}$=8.8 Hz, 1H, H-3'), 6.02 (s, 1H, H-1'), 6.41 (d, J$_{5,6}$=3.8 Hz, 1H, H-5), 7.39 (d, 1H, H-6), 8.43 (s, 1H, H-4). ES MS: 281.4(MH$^+$).

EXAMPLE 20

2-Amino-5-methyl-7-(2-C,2-O-dimethyl-β-D-ribofuranosyl)-7H-pyrrolo[2,3-d]pyrimidin-4(3H)-one

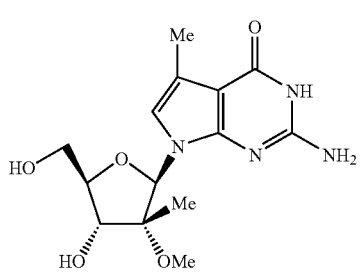

Step A: 2-Amino-4-chloro-7-[3,5-bis-O-(2,4-dichlorophenylmethyl)-2-C-methyl-β-D-ribofuranosyl]-5-methyl-7H-pyrrolo[2,3-d]pyrimidine To an ice-cold solution of the product from Step C of Example 2 (1.57 g, 3.16 mmol) in CH$_2$Cl$_2$ (50 mL) was added HBr (5.7 M in acetic acid; 3.3 mL) dropwise. The reaction mixture was stirred at 0° C. for 1 h and then at room temperature for 2 h, concentrated in vacuo and co-evaporated with toluene (2×20 mL). The resulting oil was dissolved in MeCN (20 mL) and added dropwise to a solution of the sodium salt of 2-amino-4-chloro-5-methyl-1H-pyrrolo[2,3-d]pyrimidine in acetonitrile [generated in situ from 2-amino-4-chloro-5-methyl-1H-pyrrolo[2,3-d]pyrimidine

[for preparation, see *Liebigs Ann. Chem.* 1984: 708-721] (1.13 g, 6.2 mmol) in anhydrous acetonitrile (150 mL), and NaH (60% in mineral oil, 248 mg, 6.2 mmol), after 2 h of vigorous stirring at room temperature]. The combined mixture was stirred at room temperature for 24 h and then evaporated to dryness. The residue was suspended in water (100 mL) and extracted with EtOAc (300+150 mL). The combined extracts were washed with brine (100 mL), dried over Na$_2$SO$_4$, filtered and evaporated. The crude product was purified on a silica gel column (5×7 cm) using ethyl acetate/hexane (0 to 30% EtOAc in 5% step gradient) as the eluent. Fractions containing the product were combined and evaporated in vacuo to give the desired product (0.96 g) as a colorless foam.

Step B: 2-Amino-4-chloro-7-[3,5-bis-O-(2,4-dichlorophenylmethyl)-2-C,2-O-dimethyl-β-D-ribofuranosyl]-5-methyl-7H-pyrrolo[2,3-d]pyrimidine To an ice-cold mixture of the product from Step A (475 mg, 0.7 mmol) in THF (7 mL) was added NaH (60% in mineral oil, 29 mg) and stirred at 0° C. for 0.5 h. Then MeI (48 µL) was added and reaction mixture stirred at room temperature for 24 h. The reaction was quenched with MeOH and the mixture evaporated. The crude product was purified on a silica gel column (5×3.5 cm) using hexane/ethyl acetate (9/1, 7/1, 5/1 and 3/1) as eluent. Fractions containing the product were combined and evaporated to give the desired compound (200 mg) as a colorless foam.

Step C: 2-Amino-7-[3,5-bis-O-(2,4-dichlorophenylmethyl)-2-C,2-O-dimethyl-β-D-ribofuranosyl]-5-methyl-7H-pyrrolo[2,3-d]pyrimidine-4(3H)-one A mixture of the product from Step B (200 mg, 0.3 mmol) in 1,4-dioxane (15 mL) and aqueous NaOH (2N, 15 mL) in a pressure bottle was heated overnight at 135° C. The mixture was then cooled to 0° C., neutralized with 2N aqueous HCl and evaporated to dryness. The crude product was suspended in MeOH, filtered, and the solid thoroughly washed with MeOH. The combined filtrate was concentrated, and the residue purified on a silica gel column (5×5 cm) using CH$_2$Cl$_2$/MeOH (40/1, 30/1 and 20/1) as eluent to give the desired compound (150 mg) as a colorless foam.

Step D: 2-Amino-5-methyl-7-(2-C,2-O-dimethyl-β-D-ribofuranosyl)-7H-pyrrolo[2,3-d]pyrimidin-4(3H)-one A mixture of the product from Step C (64 mg, 0.1 mmol) in MeOH (5 mL) and Et$_3$N (0.2 mL) and 10% Pd/C (24 mg) was hydrogenated on a Parr hydrogenator at 50 psi at r.t. for 1.5 days, then filtered through a Celite pad which was thoroughly washed with MeOH. The combined filtrate was evaporated and the residue purified on a silica gel column (3×4 cm) with CH$_2$Cl$_2$/MeOH (30/1, 20/1) as eluent to yield 2-amino-5-methyl-7-(5-O-benzyl-2-C,2-O-dimethyl-β-D-ribofuranosyl)-7H-pyrrolo[2,3-d]pyrimidin-4(3H)-one. The compound (37 mg) was further hydrogenated in EtOH (2 mL) with 10% Pd/C and under atmospheric pressure of hydrogen. After stirring 2 days at r.t., the reaction mixture was filtered through Celite, the filtrate evaporated and the crude product purified on a silica gel column (1×7 cm) with CH$_2$Cl$_2$/MeOH (30/1, 20/1 and 10/1) as eluent to yield the title compound (12 mg) after freeze-drying.

$^1$H NMR (200 MHz, CD$_3$OD): δ 0.81 (s, 3H, 2'C-Me), 2.16 (d, J$_{H-6,C5-Me}$=1.3 Hz, 3H, C5-Me), 3.41 (s, 3H, 2'-OMe), 3.67 (dd, J$_{5',4'}$=3.4 Hz, J$_{5',5''}$=12.6 Hz, 1H, H-5'), 3.81-3.91 (m, 3H, H-5", H-4', H-3'), 6.10 (s, 1H, H-1'), 6.66 (d, 1H, H-6). ES MS: 323.3 (M−H)$^+$.

EXAMPLE 21

4-Amino-5-methyl-7-(2-C-methyl-β-D-ribofuranosyl)-7H-pyrrolo[2,3-d]pyrimidine

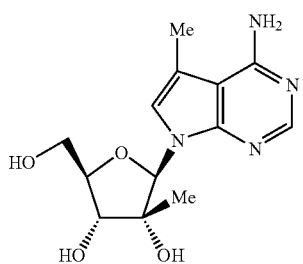

Step A: 4-Chloro-7-[3,5-bis-O-(2,4-dichlorophenylmethyl)-2-C-methyl-β-D-ribofuranosyl]-5-methyl-7H-pyrrolo[2,3-d]pyrimidine To an ice-cold solution of the product from Step C of Example 2 (1.06 g, 2.1 mmol) in CH$_2$Cl$_2$ (30 mL) was added HBr (5.7 M in acetic acid; 2.2 mL) dropwise. The reaction mixture was stirred at 0° C. for 1 h and then at room temperature for 2 h, concentrated in vacuo and co-evaporated with toluene (2×15 mL). The resulting oil was dissolved in MeCN (10 mL) and added dropwise into a solution of the sodium salt of 4-chloro-5-methyl-1H-pyrrolo[2,3-d]pyrimidine in acetonitrile [generated in situ from 4-chloro-5-methyl-1H-pyrrolo[2,3-d]pyrimidine [for preparation, see *J. Med. Chem.* 33: 1984 (1990)] (0.62 g, 3.7 mmol) in anhydrous acetonitrile (70 mL), and NaH (60% in mineral oil, 148 mg, 3.7 mmol), after 2 h of vigorous stirring at room temperature]. The combined mixture was stirred at room temperature for 24 h and then evaporated to dryness. The residue was suspended in water (100 mL) and extracted with EtOAc (250+100 mL). The combined extracts were washed with brine (50 mL), dried over Na$_2$SO$_4$, filtered and evaporated. The crude product was purified on a silica gel column (5×5 cm) using hexane/ethyl acetate (9/1, 5/1, 3/1) gradient as the eluent. Fractions containing the product were combined and evaporated in vacuo to give the desired product (0.87 g) as a colorless foam.

Step B: 4-Chloro-5-methyl-7-(2-C-methyl-β-D-ribofuranosyl)-7H-pyrrolo[2,3-d]pyrimidine To a solution of the compound from Step A (0.87 g, 0.9 mmol) in dichloromethane (30 mL) at −78° C. was added boron trichloride (1M in dichloromethane, 9.0 mL, 9.0 mmol) dropwise. The mixture was stirred at −78° C. for 2.5 h, then at −30° C. to −20° C. for 3 h. The reaction was quenched by addition of methanol/dichloromethane (1:1) (9 mL) and the resulting mixture stirred at −15° C. for 30 min, then neutralized with aqueous ammonia at 0° C. and stirred at room temperature for 15 min. The solid was filtered and washed with CH$_2$Cl$_2$/MeOH (1/1, 50 mL). The combined filtrate was evaporated, and the residue was purified on a silica gel column (5×5 cm) using CH$_2$Cl$_2$ and CH$_2$Cl$_2$/MeOH (40/1 and 30/1) gradient as the eluent to furnish the desired compound (0.22 g) as a colorless foam.

Step C: 4-Amino-5-methyl-7-(2-C-methyl-β-D-ribofuranosyl)-7H-pyrrolo[2,3-d]pyrimidine To the compound from Step B (0.2 g, 0.64 mmol) was added methanolic ammonia (saturated at 0° C.; 40 mL). The mixture was heated in a stainless steel autoclave at 100° C.

for 14 h, then cooled and evaporated in vacuo. The crude mixture was purified on a silica gel column (5×5 cm) with CH$_2$Cl$_2$/MeOH (50/1, 30/1, 20/1) gradient as eluent to give the title compound as a white solid (0.12 g).

$^1$H NMR (DMSO-d$_6$): δ 0.60 (s, 3H, 2'C-Me), 2.26 (s, 3H, 5C-Me), 3.52-3.61 (m, 1H, H-5'), 3.70-3.88 (m, 3H, H-5", H-4', H-3'), 5.00 (s, 1H, 2'-OH), 4.91-4.99 (m, 3H, 2'-OH, 3'-OH, 5'-OH), 6.04 (s, 1H, H-1'), 6.48 (br s, 2H, NH$_2$), 7.12 (s, 1H, H-6), 7.94 (s, 1H, H-2). ES MS: 295.2 (MH$^+$).

EXAMPLE 22

4-Amino-7-(2-C-methyl-β-D-ribofuranosyl)-7H-pyrrolo[2,3-d]pyrimidine-5-carboxylic Acid

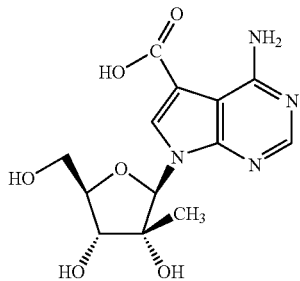

The compound of Example 6 (0.035 g, 0.11 mmol) was dissolved in a mixture of aqueous ammonia (4 mL, 30 wt %) and saturated methanolic ammonia (2 mL), and a solution of H$_2$O$_2$ in water (2 mL, 35 wt %) was added. The reaction mixture was stirred at room temperature for 18 h. Solvent was removed under reduced pressure, and the residue obtained was purified by HPLC on a reverse phase column (Altech Altima C-18, 10×299 mm, A=water, B=acetonitrile, 10 to 60% B in 50 min, flow 2 mL/min) to yield the title compound (0.015 g, 41%) as a white solid.

$^1$H NMR (CD$_3$OD): δ 0.85 (s, 3H, Me), 3.61 (m, 1H), 3.82 (m, 1H) 3.99-4.86 (m, 2H), 6.26 (s, 1H), 8.10 (s, 2H) 8.22(s, 1H); $^{13}$C NMR (CD$_3$OD): 20.13, 61.37, 73.79, 80.42, 84.01, 93.00, 102.66, 112.07, 130.07, 151.40, 152.74, 159.12, 169.30. HRMS (FAB) Calcd for C$_{13}$H$_{17}$N$_4$O$_6$$^+$ 325.1148, found 325.1143.

EXAMPLE 23

4-Amino-7-(2-C-vinyl-β-D-ribofuranosyl)-7H-pyrrolo[2,3-d]pyrimidine

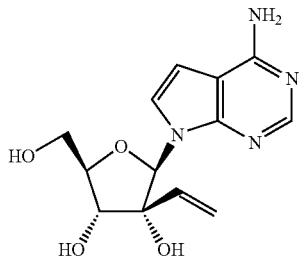

Step A: 3,5-Bis-O-(2,4-dichlorophenylmethyl)-2-C-vinyl-1-O-methyl-α-D-ribofuranose Cerium chloride heptahydrate (50 g, 134.2 mmol) was finely crushed in a pre-heated mortar and transferred to a round-bottom flask equipped with a mechanical stirrer. The flask was heated under high vacuum overnight at 160° C. The vacuum was released under argon and the flask was cooled to room temperature. Anhydrous THF (300 mL) was cannulated into the flask. The resulting suspension was stirred at room temperature for 4 h and then cooled to −78° C. Vinylmagnesium bromide (1M in THF, 120 mL, 120 mmol) was added and stirring continued at −78° C. for 2 h. To this suspension was added a solution of 3,5-bis-O-(2,4-dichlorophenylmethyl)-1-O-methyl-α-D-erythro-pentofuranose-2-ulose (14 g, 30 mmol) [from Example 2, Step B] in anhydrous THF (100 mL), dropwise with constant stirring. The reaction was stirred at −78° C. for 4 h. The reaction was quenched with saturated ammonium chloride solution and allowed to come to room temperature. The mixture was filtered through a celite pad and the residue washed with Et$_2$O (2×500 mL). The organic layer was separated and the aqueous layer extracted with Et$_2$O (2×200 mL). The combined organic layers were dried over anhydrous Na$_2$SO$_4$ and concentrated to a viscous yellow oil. The oil was purified by flash chromatography (SiO$_2$, 10% EtOAc in hexanes). The title compound (6.7 g, 13.2 mmol) was obtained as a pale yellow oil.

Step B: 4-Chloro-7-[3,5-bis-O-(2,4-dichlorophenylmethyl)-2-C-vinyl-β-D-ribofuranosyl]-7H-pyrrolo[2,3-d]pyrimidine To a solution of the compound from Step A (6.4 g, 12.6 mmol) in anhydrous dichloromethane (150 mL) at −20° C. was added HBr (30% solution in AcOH, 20 mL, 75.6 mmol) dropwise. The resulting solution was stirred between −10° C. and 0° C. for 4 h, evaporated in vacuo and co-evaporated with anhydrous toluene (3×40 mL). The oily residue was dissolved in anhydrous acetonitrile (100 mL) and added to a solution of the sodium salt of 4-chloro-1H-pyrrolo[2,3-d]pyrimidine (5.8 g, 37.8 mmol) in acetonitrile (generated in situ as described in Example 2) at −20° C. The resulting mixture was allowed to come to room temperature and stirred at room temperature for 24 h. The mixture was then evaporated to dryness, taken up in water and extracted with EtOAc (2×300 mL). The combined extracts were dried over Na$_2$SO$_4$, filtered and evaporated. The crude mixture was purified by flash chromatography (SiO$_2$, 10% EtOAc in hexanes) and the title compound (1.75 g) isolated as a white foam.

Step C: 4-Amino-7-[3,5-bis-O-(2,4dichlorophenylmethyl)-2-C-vinyl-β-D-ribofuranosyl]-7H-pyrrolo[2,3-d]pyrimidine The compound from Step B (80, mg) was dissolved in the minimum amount of 1,4dioxane and placed in a stainless steel bomb. The bomb was cooled to −78° C. and liquid ammonia was added. The bomb was sealed and heated at 90° C. for 24 h. The ammonia was allowed to evaporate and the residue concentrated to a white solid which was used in the next step without further purification.

Step D: 4-Amino-7-(2-C-vinyl-β-D-ribofuranosyl)-7H-pyrrolo[2,3-d]pyrimidine

To a solution of the compound from Step C (60 mg) in dichloromethane at −78° C. was added boron trichloride (1M in dichloromethane) dropwise. The mixture was stirred at −78° C. for 2.5 h, then at −30° C. to −20° C. for 3 h. The reaction was quenched by addition of methanol/dichloromethane (1:1) and the resulting mixture stirred at −15° C. for 0.5 h, then neutralized with aqueous ammonia at 0° C. and stirred at room temperature for 15 min. The solid was filtered and washed with methanol/dichloromethane (1:1). The combined filtrate was evaporated and the residue purified by flash chromatography (SiO$_2$, 10% methanol in EtOAc containing 0.1% triethylamine). The fractions containing the product were evaporated to give the title compound as a white solid (10 mg).

$^1$H NMR (DMSO-$d_6$): δ 3.6 (m, 1H, H-5'), 3.8 (m, 1H, H-5"), 3.9 (m, d, 1-H, H-4'), 4.3 (t, 1H, H-3'), 4.8-5.3(m, 6H, CH=CH$_2$, 2'-OH, 3'-OH, 5'-OH) 6.12 (s, 1H, H-1'), 6.59 (d, 1H, H-5), 7.1 (br s, 1H, NH2), 7.43 (d, 1H, H-6), 8.01 (s, 1H, H-2). ES-MS: Found: 291.1 (M−H$^-$); calc. for C$_{13}$H$_{16}$N$_4$O$_4$-H$^-$: 291.2.

EXAMPLE 24

4-Amino-7-(2-C-hydroxymethyl-β-D-ribofuranosyl)-7H-pyrrolo[2,3-d]pyrimidine

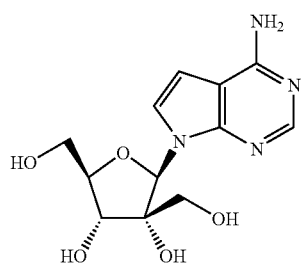

Step A: 4-Chloro-7-[3,5-bis-O-(2,4-dichlorophenylmethyl)-2-C-hydroxymethyl-β-D-ribofuranosyl]-7H-pyrrolo[2,3-d]pyrimidine To a solution of the compound from Example 23, Step B (300 mg, 0.48 mmol) in 1,4-dioxane (5 mL) were added N-methylmorpholine-N-oxide (300 mg, 2.56 mmol) and osmium tetroxide (4% solution in water, 0.3 mL). The mixture was stirred in the dark for 14 h. The precipitate was removed by filtration through a celite plug, diluted with water (3×), and extracted with EtOAc. The EtOAc layer was dried over Na$_2$SO$_4$ and concentrated in vacuo. The oily residue was taken up in dichloromethane (5 mL) and stirred over NaIO$_4$ on silica gel (3 g, 10% NaIO$_4$) for 12 h. The silica gel was removed by filtration and the residue was evaporated and taken up in absolute ethanol (5 mL). The solution was cooled in an ice bath and sodium borohydride (300 mg, 8 mmol) was added in small portions. The resulting mixture was stirred at room temperature for 4 h and then diluted with EtOAc. The organic layer was washed with water (2×20 mL), brine (20 mL) and dried over Na$_2$SO$_4$. The solvent was evaporated and the residue purified by flash chromatography (SiO$_2$, 2:1 hexanes/EtOAc) to give the title compound (160 mg, 0.25 mmol) as white flakes.

Step B: 4-Amino-7-[3,5-bis-O-(2,4-dichlorophenylmethyl)-2-C-hydroxymethyl-β-D-ribofuranosyl]-7H-pyrrolo[2.3-d]pyrimidine The compound from Step A (150 mg, 0.23 mmol) was dissolved in the minimum amount of 1,4-dioxane (10 mL) and placed in a stainless steel bomb. The bomb was cooled to −78° C. and liquid ammonia was added. The bomb was sealed and heated at 90° C. for 24 h. The ammonia was allowed to evaporate and the residue concentrated to a white solid which was used in the next step without further purification.

Step C: 4-Amino-7-(2-C-hydroxymethyl-β-D-ribofuranosyl)-7H-pyrrolo[2,3-d]pyrimidine The compound from Step B (120 mg, 0.2 mmol) dissolved in 1:1 methanol/dichloromethane, 10% Pd—C was added, and the suspension stirred under an H$_2$ atmosphere for 12 h. The catalyst was removed by filtration through a celite pad and washed with copious amounts of methanol. The combined filtrate was evaporated in vacuo and the residue was purified by flash chromatography (SiO$_2$, 10% methanol in EtOAc containing 0.1% triethylamine) to give the title compound (50 mg) as a white powder.

$^1$H NMR (CD$_3$OD): δ 3.12 (d, 1H, CH$_2$'), 3.33 (d, 1H, CH$_2$"), 3.82 (m, 1H, H-5'), 3.99-4.1(m, 2H, H-4', H-5"), 4.3 (d, 1H, H-3'), 6.2 (s, 1H, H-1'), 6.58 (d, 1H, H-5), 7.45 (d, 1H, H-6), 8.05 (s, 1H, H-2). LC-MS: Found: 297.2 (M+H$^+$); calc. for C$_{12}$H$_{16}$N$_4$O$_5$+H$^+$: 297.3.

EXAMPLE 25

4-Amino-7-(2-C-fluoromethyl-β-D-ribofuranosyl)-7H-pyrrolo[2,3-d]pyrimidine

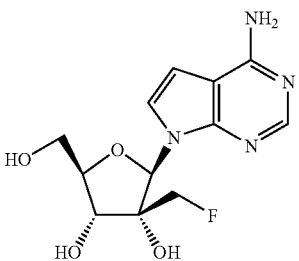

Step A: 4-Chloro-7-[3,5-bis-O-(2,4-dichlorophenylmethyl)-2-C-fluoromethyl-β-D-ribofuranosyl]-7H-pyrrolo[2,3-d]pyrimidine To a solution of the compound from Example 24, Step A (63 mg, 0.1 mmol) in anhydrous dichloromethane (5 mL) under argon, were added 4-dimethylaminopyridine (DMAP) (2 mg, 0.015 mmol) and triethylamine (62 μL, 0.45 mmol). The solution was cooled in an ice bath and p-toluenesulfonyl chloride (30 mg, 0.15 mmol) was added. The reaction was stirred at room temperature overnight, washed with NaHCO$_3$ (2×10 mL), water (10 mL), brine (10 mL), dried over Na$_2$SO$_4$ and concentrated to a pink solid in vacuo. The solid was dissolved in anhydrous THF (5 mL) and cooled in an icebath. Tetrabutylammonium fluoride (1M solution in THF, 1 mL, 1 mmol) was added and the mixture stirred at room temperature for 4 h. The solvent was removed in vacuo, the residue taken up in dichloromethane, and washed with NaHCO$_3$ (2×10 mL), water (10 mL) and brine (10 mL). The dichloromethane layer was dried over anhydrous Na$_2$SO$_4$, concentrated in vacuo, and purified by flash chromatography (SiO$_2$, 2:1 hexanes/EtOAc) to afford the title compound (20 mg) as a white solid.

Step B: 4-Amino-7-[3,5-bis-O-(2,4-dichlorophenylmethyl)-2-C-fluoromethyl-β-D-ribofuranosyl]-7H-pyrrolo[2,3-d]pyrimidine The compound from Step A (18 mg, 0.03 mmol) was dissolved in the minimum amount of 1,4-dioxane and placed in a stainless steel bomb. The bomb was cooled to −78° C. and liquid ammonia was added. The bomb was sealed and heated at 90° C. for 24 h. The ammonia was allowed to evaporate and the residue concentrated to a white solid which was used in the next step without further purification.

Step C: 4-Amino-7-(2-C-fluoromethyl-β-D-ribofuranosyl)-7H-pyrrolo[2,3-d]pyrimidine The compound from Step B (16 mg) was dissolved in 1:1 methanol/dichloromethane, 10% Pd—C was added, and the suspension stirred under an $H_2$ atmosphere for 12 h. The catalyst was removed by filtration through a celite pad and washed with copious amounts of methanol. The combined filtrate was evaporated in vacuo and the residue was purified by flash chromatography ($SiO_2$, 10% methanol in EtOAc containing 0.1% triethylamine) to give the title compound (8 mg) as a white powder.

$^1$H NMR (DMSO-$d_6$): δ 3.6-3.7 (m, 1H, H-5'), 3.8-4.3 (m, 5H, H-5", H-4', H-3', $CH_2$) 5.12 (t, 1H, 5'-OH), 5.35 (d, 1H, 3'-OH), 5.48 (s, 1H, 2'-OH), 6.21 (s, 1H, H-1'), 6.52 (d, 1H, H-5), 6.98 (br s, 2H, NH2), 7.44 (d, 1 H, H-6), 8.02 (s, 1H, H-2). $^{19}$F NMR (DMSO-$d_6$): δ-230.2 (t). ES-MS: Found: 299.1 (M+H$^+$), calc. for $C_{12}H_{15}FN_4O_4$+H$^+$: 299.27.

EXAMPLES 26 and 27

4-Amino-7-(3-deoxy-2-C-methyl-β-D-ribofuranosyl)-7H-pyrrolo[2,3-d]pyrimidine and 4-amino-7-(3-deoxy-2-C-methyl-β-D-arabinofuranosyl)-7H-pyrrolo[2,3-d]pyrimidine

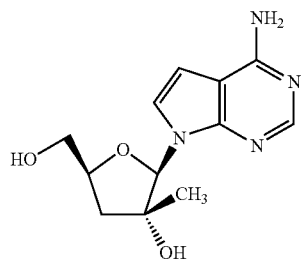

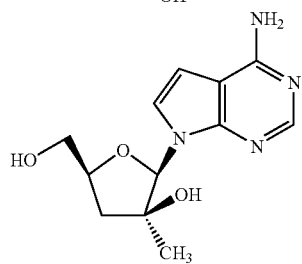

Step A: 7-[2,5-Bis-O-(tert-butyldimethylsilyl)-β-D-ribofuranosyl]-7H-pyrrolo[2,3-d]pyrimidine and 7-[3,5-Bis-O-(tert-butyldimethylsilyl)-β-D-ribofuranosyl]-7H-pyrrolo[2,3-d]pyrimidine To a stirred solution of tubercidin (5.0 g, 18.7 mmol) in a mixture of pyridine (7.5 mL) and DMF (18.5 mL) was added silver nitrate (6.36 g, 38.8 mmol). This mixture was stirred at room temperature for 2 h. It was cooled in an ice bath and THF (37.4 mL) and tert-butyldimethylsilyl chloride (5.6 g, 37 mmol) was added and the mixture was stirred at room temperature for 2 h. The mixture was then filtered through a pad of celite and washed with THF. The filtrate and washings were diluted with ether containing a small amount of chloroform. The organic layer was washed successively with sodium bicarbonate and water (3×50 mL), dried over anhydrous sodium sulfate and concentrated. The pyridine was removed by coevaporation with toluene and the residue was purified by flash chromatography on silica gel using 5-7% MeOH in $CH_2Cl_2$ as the eluent; yield 3.0 g.

Step B: 7-[2.5-Bis-O-(tert-butyldimethylsilyl)-β-D-ribofuranosyl)]-4-[di-(4-methoxyphenyl)phenylmethyl]amino-7H-pyrrolo[2,3-d]pyrimidine and 7-[3,5-bis-O-(tert-butyldimethylsilyl)-β-D-ribofuranosyl]-4-[di-(4-methoxyphenyl)phenylmethyl]amino-7H-pyrrolo[2,3-d]pyrimidine To a solution of mixture of the compounds from Step A (3.0 g, 6.0 mmol) in anhydrous pyridine (30 mL) was added 4,4'-dimethoxytrityl chloride (2.8 g, 8.2 mmol) and the reaction mixture was stirred at room temperature overnight. The mixture was then triturated with aqueous pyridine and extracted with ether. The organic layer was washed with water, dried over anhydrous sodium sulfate and concentrated to a yellow foam (5.6 g). The residue was purified by flash chromatography over silica gel using 20-25% EtOAc in hexanes as the eluent. The appropriate fractions were collected and concentrated to furnish 2',5'-bis-O-(tert-butyldimethylsilyl)- and 3',5'-bis-O-(tert-butyldimethylsilyl) protected nucleosides as colorless foams (2.2 g and 1.0 g, respectively).

Step C: 7-[2,5-Bis-O-(tert-butyldimethylsilyl)-3-O-tosyl-β-D-ribofuranosyl)]-4-[di-(4-methoxyphenyl)phenylmethyl]amino-7H-pyrrolo[2,3 d]pyrimidine To an ice-cooled solution of 2',5'-bis-O-(tert-butyldimethylsilyl)-protected nucleoside from Step B (2.0 g, 2.5 mmol) in pyridine (22 mL) was added p-toluenesulfonyl chloride (1.9 g, 9.8 mmol). The reaction mixture was stirred at room temperature for four days. It was then triturated with aqueous pyridine (50%, 10 mL) and extracted with ether (3×50 mL) containing a small amount of $CH_2Cl_2$ (10 mL). The organic layer was washed with sodium bicarbonate and water (3×30 mL). The organic layer was dried over anhydrous $Na_2SO_4$ and concentrated. Pyridine was removed by co-evaporation with toluene (3×25 mL). The residual oil was filtered through a pad of silica gel using hexane:ethyl acetate (70:30) as eluent; yield 1.4 g.

Step D: 4-[di-(4-methoxyphenyl)phenylmethyl]amino-7-[3-O-tosyl-β-D-ribofuranosyl-7H-pyrrolo[2,3-d]pyrimidine A solution of the compound from Step C (1.0 g, 1.1 mmol) and THF (10 mL) was stirred with tetrabutylammonium fluoride (IM solution in THF, 2.5 mL) for 0.5 h. The mixture was cooled and diluted with ether (50 mL). The solution was washed with water (3×50 mL), dried over anhydrous $Na_2SO_4$, and concentrated to an oil. The residue was purified by passing through a pad of silica gel using hexane:ethyl acetate (1:1) as eluent; yield 780 mg.

Step E: 4-Amino-7-(3-deoxy-2-C-methyl-β-D-ribofuranosyl)-7H-pyrrolo[2,3-d]-pyrimidine and 4-amino-7-(3-deoxy-2-C-methyl-β-D-arabinofuranosyl)-7H-pyrrolo-[2,3-d]pyrimidine A solution of $CH_3MgI$ (3.0 M solution in ether, 3.0 mL) in anhydrous toluene (3.75 mL) was cooled in an ice bath. To this was added a solution of the compound from Step D (500 mg, 0.8 mmol) in anhydrous toluene (3.7 mL). The resulting mixture was stirred at room temperature for 3.5 h. It was cooled and treated with aqueous $NH_4Cl$ solution and extracted with ether (50 mL containing 10 mL of $CH_2Cl_2$). The organic layer was separated and washed with brine (2×30 mL) and water (2×25 mL), dried over anhydrous $Na_2SO_4$ and concentrated to an oil which was purified by flash chromatography on silica gel using 4% MeOH in $CH_2Cl_2$ to fish the 2-C-α-methyl compound (149 mg) and the 2-C-β-methyl compound (34 mg). These derivatives were separately treated with 80% acetic acid and the reaction mixture stirred at room temperature for 2.5 h. The acetic acid was removed by repeated co-evaporation with ethanol and toluene. The residue was partitioned between chloroform and water. The aqueous layer was washed with chloroform and concentrated. The evaporated residue was purified on silica gel using 5-10% MeOH in $CH_2Cl_2$ as the eluent to furnish the desired compounds as white solids.

4-Amino-7-(3-deoxy-2-C-methyl-β-D-ribofuranosyl)-7H-pyrrolo[2,3-d]pyrimidine (9.0 mg):

$^1$H NMR (DMSO-$d_6$): δ 0.74 (s, 3H, $CH_3$), 1.77 (dd, 1H, H-3'), 2.08 (t, 1H, H-3''), 3.59 (m, 1H, H-5'), 3.73 (m, 1H, H-5''), 4.15 (m, 1H, H4'), 5.02 (t, 1H, OH-5'), 5.33 (s, 1H, OH-2'), 6.00 (s, 1H, H-1'), 6.54 (d, 1H, H-7), 6.95 (br s, 2H, $NH_2$), 7.47 (d, 1H, H-8), 8.00 (s, 1H, H-2); ES-MS: 263.1 [M−H].

4-Amino-7-(3-deoxy-2-C-methyl-β-D-arabinofuranosyl)-7H-pyrrolo[2,3-d]pyrimidine (15 mg):

$^1$H NMR (DMSO-$_6$): δ 1.23 (s, 3H, $CH_3$), 2.08 (ddd, 2H, H-3' and 3''), 3.57 (m, 2H, H-5' and 5''), 4.06 (m, 1H, H-4), 5.10 (s, 1H, OH-2'), 5.24 (t, 1H, OH-5'), 6.01 (s, 1H, H-1'), 6.49 (d, 1H, H-7), 6.89 (br s, 2H, $NH_2$), 7.35 (d, 1H, H-8), 8.01 (s, 1H, H-2). ES-MS: 265.2[M+H].

EXAMPLE 28

4-Amino-7-(2,4-C-dimethyl-β-D-ribofuranosyl)-7H-pyrrolo[2,3-d]pyrimidine

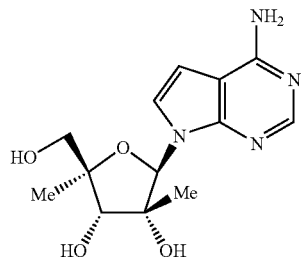

Step A: 5-Deoxy-1,2-O-isopropylidene-D-xylofuranose 1,2-O-Isopropylidene-D-xylofuranose (38.4 g, 0.2 mol), 4-dimethylaminopyridine (5 g), triethylamine (55.7 mL, 0.4 mol) were dissolved in dichloromethane (300 mL). p-Toluenesulfonyl chloride (38.13 g, 0.2 mol) was added and the reaction mixture was stirred at room temperature for 2 h. The reaction mixture was then poured into saturated aqueous sodium bicarbonate (500 mL) and the two layers were separated. The organic layer was washed with aqueous citric acid solution (20%, 200 mL), dried ($Na_2SO_4$) and evaporated to give a solid (70.0 g). The solid was dissolved in dry THF (300 mL) and $LiAlH_4$ (16.0 g, 0.42 mol) was added in portions over 30 min. The mixture was stirred at room temperature for 15. Ethyl acetate (100 mL) was added dropwise over 30 min and the mixture was filtered through a silica gel bed. The filtrate was concentrated and the resulting oil was chromatographed on silica gel (EtOAc/hexane 1/4) to afford the product as a solid (32.5 g).

Step B: 3,5-Bis-O-(2,4-dichlorophenylmethyl)-1-O-methyl-4-methyl-α-D-ribofuranose Chromium oxide (50 g, 0.5 mol), acetic anhydride (50 mL, 0.53 mol) and pyridine (100 ml, 1.24 mol) were added to dichloromethane (1 L) in an ice-water bath and the mixture was stirred for 15 min. 5-Deoxy-1,2-O-isopropylidene-D-xylofuranose (32 g, 0.18 mol) in dichloromethane (200 mL) was added, and the mixture was stirred at the same temperature for 30 min. The reaction solution was diluted with ethyl acetate (1 L) and filtered through a silica gel bed. The filtrate was concentrated to give a yellow oil. The oil was dissolved in 1,4-dioxane (1 L) and formaldehyde (37%, 200 mL). The solution was cooled to 0° C. and solid KOH (50 g) was added. The mixture was stirred at room temperature overnight and was then extracted with ethyl acetate (6×200 mL). After concentration, the residue was chromatographed on silica gel (EtOAc) to afford the product as an oil (1.5 g). The oil was dissolved in 1-methyl-2-pyrrolidinone (20 mL) and 2,4-dichlorophenylmethyl chloride (4 g, 20.5 mmol) and NaH (60%, 0.8 g) were added. The mixture was stirred overnight and diluted with toluene (100 mL). The mixture was then washed with saturated aqueous sodium bicarbonate (3×50 mL), dried ($Na_2SO_4$) and evaporated. The residue was dissolved in methanol (50 mL) and HCl in dioxane (4 M, 2 mL) was added. The solution was stirred overnight and evaporated. The residue was chromatographed on silica gel (EtOAc/hexane: 1/4) to afford the desired product as an oil (2.01 g).

Step C: 3,5-Bis-O-(2,4-dichlorophenylmethyl)-2,4-di-C-methyl-1-O-methyl-α-D-ribofuranose The product (2.0 g, 4.0 mmol) from Step B and Dess-Martin periodinane (2.0 g) in dichloromethane (30 mL) were stirred overnight at room temperature and then concentrated under reduced pressure. The residue was triturated with ether ether (50 mL) and filtered. The filtrate was washed with a solution of $Na_2S_2O_3.5H_2O$ (2.5 g) in saturated aqueous sodium bicarbonate solution (50 mL), dried ($MgSO_4$), filtered and evaporated. The residue was dissolved in anhydrous $Et_2O$ (20 mL) and was added dropwise to a solution of MeMgBr in $Et_2O$ (3 M, 10 mL) at −78° C. The reaction mixture was allowed to warm to −30° C. and stirred at −30° C. to −15° C. for 5 h, then poured into saturated aqueous ammonium chloride (50 mL). The two layers were separated and the organic layer was dried ($MgSO_4$), filtered and concentrated. The residue was chromatographed on silica gel (EtOAc/hexane: 1/9) to afford the title compound as a syrup (1.40 g).

Step D: 4-Chloro-7-[3,5-bis-O-(2,4-dichlorophenylmethyl)-2,4-di-C-methyl-β-D-ribofuranosyl]-7H-pyrrolo[2.3-d]pyrimidine To the compound from Step C (0.70 g, 1.3 mmol) was added HBr (5.7 M in acetic acid, 2 mL). The resulting solution was stirred at room temperature for 1 h, evaporated in vacuo and co-evaporated with anhydrous toluene (3×10 mL). 4-Chloro-1H-pyrrolo[2,3-d]pyrimidine (0.5 g, 3.3 mmol) and powdered KOH (85%, 150 mg, 2.3 mmol) were stirred in 1-methyl-2-pyrrolidinone (5 mL) for 30 min and the mixture was co-evaporated with toluene (10 mL). The resulting solution was poured into the above bromo sugar residue and the mixture was stirred overnight. The mixture was diluted with toluene (50 mL), washed with water (3×50 mL) and concentrated under reduced pressure. The residue was chromatographed on silica gel eluting with EtOAc/Hexane (15/85) to afford a solid (270 mg).

Step E: 4-Amino-7-(2,4-C-dimethyl-β-D-ribofuranosyl)-7H-pyrrolo[2.3-d]pyrimidine The compound from Step D (270 mg) was dissolved in dioxane (2 mL) and liquid ammonia (20 g) was added in a stainless steel autoclave. The mixture was heated at 100° C.

for 15, then cooled and evaporated. The residue was chromatographed on silica gel (EtOAc) to afford a solid (200 mg). The solid (150 mg) and Pd/C (10% 150 mg) in methanol (20 mL) were shaken under $H_2$ (30 psi) for 3 h, filtered and evaporated. The residue was chromatographed on silica gel (MeOH/$CH_2Cl_2$: 1/9) to afford the desired product as a solid (35 mg).

$^1$H NMR (DMSO-$d_6$): δ 0.65 (s, 3H), 1.18 (s, 3H), 3.43 (m, 2H), 4.06 (d, 1H, J 6.3 Hz), 4.87 (s, 1H), 5.26 (br, 1H), 5.08 (d, 1H, J 6.3 Hz), 5.25 (t, 1H, J 3.0 Hz), 6.17 (s, 1H), 6.54 (d, 1H, J 3.5 Hz), 6.97 (s, br, 2H), 7.54 (d, 1H, J 3.4 Hz), 8.02 (s, 1H). $^{13}$C NMR (DMSO-$d_6$): δ 18.19, 21.32, 65.38, 73.00, 79.33, 84.80, 90.66, 99.09, 102.41, 121.90, 149.58, 151.48, 157.38. LC-MS: Found: 295.1 (M+$^+$); calculated for $C_{13}H_{18}N_4O_4$+H$^+$: 295.1.

EXAMPLE 29

4-Amino-7-(3-deoxy-3-fluoro-2-C-methyl-β-D-ribofuranosyl)-7H-pyrrolo[2,3-d]pyrimidine

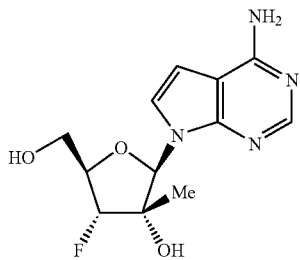

Step A: 3-Deoxy-3-fluoro-1-O-methyl-5-O-toluoyl-α-D-ribofuranose 1,2-O-Isopropylidene-D-xylofuranose (9.0 g, 50 mmol) and p-toluoyl chloride (7.0 mL, 50 mmol) in pyridine (50 mL) were stirred for 30 min. Water (10 mL) was added and the mixture was concentrated under reduced pressure. The residue was dissolved in toluene (500 mL) and the solution was washed with water (200 mL) and saturated aqueous sodium bicarbonate (200 mL). The two layers were separated and the organic layer was evaporated. The residue was dissolved in methanol (100 mL) and HCl in dioxane (4 M, 10 mL) was added. The mixture was stirred at room temperature overnight and was then evaporated under reduced pressure. The resulting oil was chromatographed on silica gel (EtOAc/hexane: 1/1) to afford an oil (10.1 g). The oil was dissolved in dichloromethane (100 mL) and diethylaminosulfur trifluoride (DAST) (5.7 mL) was added. The mixture was stirred overnight and was then poured into saturated aqueous sodium bicarbonate solution (100 mL). The mixture was extracted with toluene (2×50 mL) and the combined organic layers were concentrated. The residue was chromatographed on silica gel (EtOAc/hexane: 15/85) to afford the title compound as an oil (1.50 g).

Step B: 3-Deoxy-3-fluoro-2-C-methyl-1-O-methyl-5-O-toluoyl-α-D-ribofuranose

The product from Step A (1.0 g, 3.5 mmol) and Dess-Martin periodinane (2.5 g) in dichloromethane (20 mL) were stirred overnight at room temperature and was then concentrated under reduced pressure. The residue was triturated with diethyl ether (50 mL) and filtered. The filtrate was washed with a solution of $Na_2S_2O_3.5H_2O$ (12.5 g) in saturated aqueous sodium bicarbonate (100 mL), dried ($MgSO_4$), filtered and evaporated. The residue was dissolved in anhydrous THF (50 mL). TiCl$_4$ (3 mL) and methyl magnesium bromide in ethyl ether (3 M, 10 mL) were added at −78° C. and the mixture was stirred at −50 to −30° C. for 2 h. The mixture was poured into saturated aqueous sodium bicarbonate solution (100 mL) and filtered through Celite. The filtrate was extracted with toluene (100 mL) and evaporated. The residue was chromatographed on silica gel (EtOAc/hexane: 15/85) to afford the title compound as an oil (150 mg).

Step C: 4-Amino-7-(3-deoxy-3-fluoro-2-C-methyl-β-D-ribofuranosyl)-7H-pyrrolo[2,3-d]pyrimidine The product from Step B (150 mg, 0.5 mmol) was dissolved in HBr (30%) in acetic acid (2 mL). After one hour, the mixture was evaporated under reduced pressure and co-evaporated with toluene (10 mL). 4-Chloro-1H-pyrrolo[2,3-d]pyrimidine (0.5 g, 3.3 mmol) and powdered KOH (85%, 150 mg, 2.3 mmol) were stirred in DMF (3 mL) for 30 min and the mixture was co-evaporated with toluene (2 mL). The resulting solution was poured into the above bromo sugar and the mixture was stirred overnight. The mixture was diluted with toluene (50 mL), washed with water (3×50 mL) and concentrated under reduced pressure. The residue was chromatographed on silica gel (EtOAc/hexane: 15/85) to afford an oil (60 mg). The oil was dissolved in dioxane (2 mL) and liquid ammonia (20 g) was added in a stainless steel autoclave. The mixture was heated at 85° C. for 18 h, then cooled and evaporated. The residue was chromatographed on silica gel (methanol/dichloromethane: 1/9) to afford the title compound as a solid (29 mg).

$^1$H NMR (DMSO-$d_6$): δ 0.81 (s, 3H), 3.75 (m, 2H), 4.16 (m, 1H), 5.09 (dd, 1H, J 53.2, 7.8 Hz), 5.26 (br, 1H), 5.77 (s, 1H), 6.15 (d, 1H, J 2.9 Hz), 6.59 (d, 1H, J 3.4 Hz), 7.02 (s br, 2H), 7.39 (d, 1H, J 3.4 Hz), 8.06 (s, 1H). $^{13}$C NMR (DMSO-$d_6$): 19.40, 59.56, 77.24, 79.29, 90.15, 91.92, 99.88, 102.39, 121.17, 149.80, 151.77, 157.47. $^{19}$F NMR (DMSO-$d_6$): δ 14.66 (m). ES-MS: Found: 283.1 (M+H$^+$); calculated for $C_{12}H_{15}FN_4O_3$+H$^+$: 283.1.

EXAMPLE 30

4-Amino-7-(2-C,2-O-dimethyl-β-D-ribofuranosyl)-7H-pyrrolo[2,3-d]pyrimidine

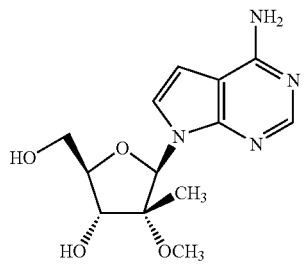

Step A: 4-chloro-7-[3,5-bis-O-(2,4-dichlorophenylmethyl)-2-C,2-O-dimethyl-β-D-ribofuranosyl]-7H-pyrrolo[2,3-d]pyrimidine To a pre-cooled (0° C.) solution of the compound from Example 2, Step D (618 mg, 1.0 mmol) in THF (8 mL) was added methyl iodide (709 mg, 5.0 mmol) and NaH (60% in mineral oil) (44 mg, 1.1 mmol). The resulting mixture was stirred overnight at room temperature and then poured into a stirred mixture of saturated aqueous ammonium chloride (50 mL) and dichloromethane (50 mL). The organic layer was washed with water (50 mL), dried (MgSO$_4$) and evaporated in vacuo. The resulting crude product was purified on silica gel using ethyl acetate/hexane as the eluent. Fractions containing the product were pooled and evaporated in vacuo to give the desired product (735 mg) as a colorless foam.

Step B: 4-amino-7-[3.5-bis-O-(2,4-dichlorophenylmethyl)-2-C,2-O-dimethyl-β-D-ribofuranosyl]-7H-pyrrolo[2,3-d]pyrimidine To the compound from Step A (735 mg, 1.16 mmol) was added methanolic ammonia (saturated at 0° C.) (20 mL). The mixture was heated in a stainless steel autoclave at 80° C. overnight, then cooled and the content evaporated in vacuo. The crude mixture was purified on silica gel using ethyl acetate/hexane as the eluent. Fractions containing the product were pooled and evaporated in vacuo to give the desired product (504 mg) as colorless foam.

Step C: 4-amino-7-(2-C,2-O-dimethyl-β-D-ribofuranosyl)-7H-pyrrolo[2,3-d]pyrimidine A mixture of the product from Step C (64 mg, 0.1 mmol), MeOH (5 mL), Et$_3$N (0.2 mL) and 10% Pd/C (61 mg) was hydrogenated on a Parr hydrogenator at 50 psi at room temperature overnight. The mixture was filtered throught celite, evaporated in vacuo and filtered through a pad of silica gel using 2% methanol in dichloromethane as eluent. The desired product was collected and evaporated in vacuo. The compound was redissolved in methanol (10 mL) and 10% Pd/C (61 mg) was added. The mixture was hydrogenated on a Parr hydrogenator at 55 psi at room temperature for two weeks. The mixture was filtered through celite, evaporated in vacuo and purified on silica gel using 10% methanol in dichloromethane as eluent. Fractions containing the product were pooled and evaporated in vacuo to give the desired product (110 mg) as a colorless foam.

$^1$H NMR (DMSO-d$_6$): δ 0.68 (s, 3H,), 3.40 (s, 3H), 3.52-3.99 (overlapping m, 4H), 4.92 (d, 1H), 5.07 (t, 1H), 6.26 (s, 1H), 6.55 (d, 1H), 7.00s br, 2H), 7.46 (d, 1H), 8.05 (s, 1H). LC-MS: Found: 293.1 (M–H$^+$); calc. for C$_{12}$H$_{16}$N4O$_4$-H$^+$: 293.12.

EXAMPLE 31

4-Methylamino-7-(2-C-methyl-β-D-ribofuranosyl)-7H-pyrrolo[2,3-d]pyrimidine

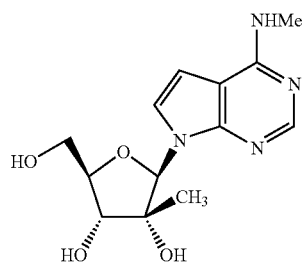

The compound from Step E of Example 2 (200 mg, 0.67 mmol) was added to methylamine (5 mL condensed in a small stainless steel autoclave) and warmed at 85° C. for 48 h, then cooled and evaporated in vacuo. The crude mixture was purified on a silica gel with ethanol as the eluent to give the title compound which separated as an amorphous solid after treatment with MeCN. The amorphous solid was dissolved in water and lyophilized to give a colorless powder (144 mg).

$^1$H NMR (DMSO-d$_6$): δ 0.63 (s, 3H, CH$_3$), 3.32 (s, 3H, N CH$_3$), 3.58-3.67 (m, 1H, H-5'), 3.79-3.39 (m, 3H, H-5", H-4', H-3'), 5.03 (s, 1H, 2'-OH), 5.04-5.11 (1H, 3'-OH, 1H, 5'-OH), 6.14 (s, 1H, H-1'), 6.58 (d, 1H, J$_{5,6}$=3.6 Hz, H-5), 7.46 (d, 1H, H-6), 7.70 (br s, 1H, NH), 8.14 (s, 1H, H-2). LC-MS: Found: 295.1 (M–H$^+$); calc. for C$_{13}$H$_{18}$N$_4$O$_4$+H$^+$: 294.3.

EXAMPLE 32

4-Dimethylamino-7-(2-C-methyl-β-D-ribofuranosyl)-7H-pyrrolo[2,3-d]pyrimidine

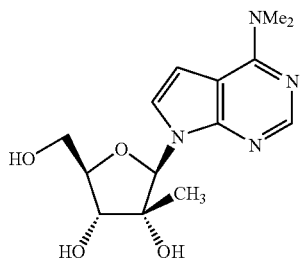

The compound from Step E of Example 2 (200 mg, 0.67 mmol) was added to dimethylamine (5 mL condensed in a small stainless steel autoclave) and warmed at 85° C. for 48 h, then cooled and evaporated in vacuo. The crude mixture was purified on a silica gel with ethanol as the eluent to give the title compound which separated as an amorphous solid after treatment with MeCN. The amorphous solid was dissolved in water and lyophilized to give a colorless powder (164 mg).

$^1$H NMR (DMSO-d$_6$): δ 0.64 (s, 3H, CH$_3$), 3.29 (s, 3H, N CH$_3$), 3.32 (s, 3H, N CH$_3$), 3.60-3.66 (m, 1H, H-5'), 3.77-3.97 (m, 3H, H-5", H-4', H-3'), 5.04 (s, 1H, 2'-OH), 5.06-5.11 (1H, 3'-OH, 1H, 5'-OH), 6.21 (s, 1H, H-1'), 6.69 (d, 1H, J$_{5,6}$=3.6 Hz, H-5), 7.55 (d, 1H, H-6), 8.13 (s, 1H, H-2). LC-MS: Found: 309.3 (M–H$^+$); calc. for C$_{14}$H$_{20}$N$_4$O$_4$+H$^+$: 308.33.

EXAMPLE 33

4-Cyclopropylamino-7-(2-C-methyl-β-D-ribofuranosyl -7H-pyrrolo[2,3-d]pyrimidine

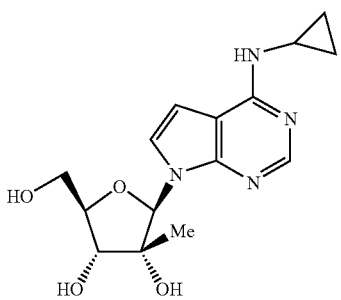

The compound from Step E of Example 2 (200 mg, 0.67 mmol) was added to cyclopropylamine (5 mL condensed in a small stainless steel autoclave) and warmed at 85° C. for 48 h, then cooled and evaporated in vacuo. The crude mixture was purified on a silica gel with ethanol as the eluent to give the title compound which separated as an amorphous solid after treatment with MeCN. The amorphous solid was dissolved in water and lyophilized to give a colorless powder (148 mg).

$^1$H NMR (DMSO-$d_6$): δ 0.51-0.58 (m, 2H), 0.64 (s, 3H, CH$_3$), 0.74-0.076 (m, 2H), 3.62-3.67 (m, 1H, H-5'), 3.79-3.82 (m, 3H, H-5"), 3.92-3.96 (m, H-4', H-3'), 5.03 (s, 1H, 2'-OH), 5.05-5.10 (1H, 3'-OH, 1H, 5'-OH), 6.15 (s, 1H, H-1'), 7.48 (d, 1H, $J_{5,6}$=3.6 Hz, H-5), 7.59 (d, 1H, H-6), 8.13 (s, 1H, H-2). LC-MS: Found: 321.1 (M–H$^+$); calc. for $C_{15}H_{20}N_4O_4$+H$^+$: 320.3.

EXAMPLE 34

4-Amino-7-(3-C-methyl-β-D-xylofuranosyl)-7H-pyrrolo[2,3-d]pyrimidine

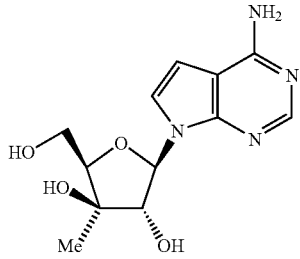

Step A: 7-[2,5-Bis-O-(tert-butyldimethylsilyl)-β-D-ribofuranosyl)]-4-[(4-methoxyphenyl)diphenylmethyl]amino-7H-pyrrolo[2,3-d]pyrimidine and 7-[3,5-bis-O-(tert-butyldimethylsilyl)-β-D-ribofuranosyl]-4-[(4-methoxyphenyl)diphenylmethyl]amino-7H-pyrrolo[2,3-d]pyrimidine To a solution of mixture of the compounds from Step A of Examples 26 and 27 (0.32 g, 0.65 mmol) in anhydrous pyridine (6 mL) was added monomethoxytrityl chloride (0.30 g, 0.98 mmol) and the reaction mixture was stirred at room temperature overnight. The mixture was then concentrated and the residue was partitioned between CH$_2$Cl$_2$ (70 mL) and water (20 mL). The organic layer was washed with water and brine, dried (Na$_2$SO$_4$) and concentrated. The residue was purified on silica gel column using 5-13% EtOAc in hexanes as the eluent. The appropriate fractions were collected and concentrated to furnish 2',5'-bis-O-(tert-butyldimethylsilyl)- and 3',5'-bis-O-(tert-butyldimethylsilyl) protected nucleosides as colorless foams (343 mg and 84 mg, respectively).

Step B: 7-[2,5-Bis-O-(tert-butyldimethylsilyl)-β-D-erythro-pentofuranos-3-ulosyl]-4-[(4-methoxyphenyl)diphenylmethyl]amino-7H-pyrrolo[2,3-d]pyrimidine To a well-stirred suspension of chromium trioxide (91 mg, 0.91 mmol) in CH$_2$Cl$_2$ (4 mL) at 0° C. were added pyridine (147 μL, 1.82 mmol) and then acetic anhydride (86 μL, 0.91 mmol). The mixture was stirred at room temperature for 0.5 h. Then the 2',5'-bis-O-(tert-butyldimethylsilyl) protected nucleoside from step A (343 mg 0.45 mmol) in CH$_2$Cl$_2$ (2.5 mL) was added and the mixture stirred at room temperature 2 h. The mixture was then poured into ice-cold EtOAc (10 mL) and filtered through a short silica gel column using EtOAc as the eluent. The filtrate was evaporated and the residue purified on a silica gel column with hexanes and hexanes/EtOAc (7/1) as the eluent to give the title compound (180 mg).

Step C: 7-[2,5-Bis-O-(tert-butyldimethylsilyl)-3-C-methyl-β-D-ribofuranosyl)-4-[(4-methoxyphenyl)diphenylmethyl]amino-7H-pyrrolo[2,3-d]pyrimidine and 7-[2,5-Bis-O-(tert-butyldimethylsilyl)-3-C-methyl-β-D-xylofuranosyl)-4-[(4-methoxyphenyl)diphenylmethyl]amino-7H-pyrrolo[2,3-d]pyrimidine To a mixture of MeMgBr (3.0 M solution in ether; 0.17 mL, 0.5 mmol) in anhydrous hexanes (1.5 mL) at room temperature was added dropwise a solution of the compound from Step B (78 mg, 0.1 mmol) in anhydrous hexanes (0.5 mL). After 2 h stirring at room temperature, the reaction mixture was poured into ice-cold water (10 mL) and diluted with EtOAc (20 mL), then filtered through Celite which was then thoroughly washed with EtOAc. The layers were separated and the organic layer was washed with brine, dried (Na$_2$SO$_4$) and concentrated. The residue was purified on a silica gel column using 8 to 25% EtOAc in hexanes as eluent to give the 3-C-methyl xylo-(60 mg) and the 3-C-methyl ribo-isomer (20 mg).

Step D: 4-Amino-7-(3-C-methyl-β-D-xylofuranosyl)-7H-pyrrolo[2,3-d]pyrimidine

To an ice-cold solution of 3-C-methyl-xylo isomer from Step C (60 mg, 0.08 mmol) in THF (2 mL) was added TBAF (1 M in THF; 0.32 mL, 0.32 mmol). The reaction mixture was stirred at room temperature for 5 h, then diluted with CH$_2$Cl$_2$ (50 mL), washed with water (3×15 mL), dried, and evaporated. The residue was dissolved in dioxane (0.3 mL) and 80% acetic acid (3 mL) was added. The reaction mixture was stirred at room temperature for 24 h and then evaporated. The residue was co-evaporated with dioxane, taken up in water (50 mL) and washed with CH$_2$Cl$_2$ (2×10 mL). The aqueous layer was concentrated and then freeze-dried. The residue was purified on silica gel column with CH$_2$Cl$_2$/MeOH (20/1 and 10/1) as the eluent to give the title compound as a white fluffy compound after freeze drying (10 mg).

$^1$H NMR (CD$_3$CN): δ 1.28 (s, 3H, CH$_3$), 3.56 (br s, 1H, OH), 3.78 (m, 3H, H-4', H-5', H-5"), 4.10 (br s, 1H, OH), 4.44 (d, 1H, J$_{2',1'}$=3.9 Hz, H-2'), 5.58 (d, 1H, H-1'), 5.85 (br s, 2H, NH$_2$), 6.15 (br s, 1H, OH), 6.48 (d, 1H, J$_{5,6}$=3.7 Hz, H-5), 7.23 (d, 1H, H-6), 8.11 (s, 1H, H-2). ES-MS: 281 [MH]$^+$.

EXAMPLE 35

4-Amino-7-(3-C-methyl-β-D-ribofuranosyl)-7H-pyrrolo[2,3-d]pyrimidine

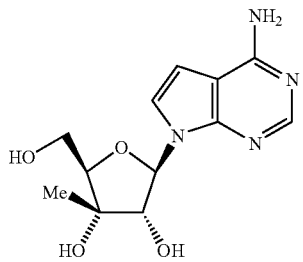

The ribo-isomer (20 mg) from Step C of Example 32 was deprotected using the procedure described in Step D of Example 32 to yield the title compound (4 mg).

¹H NMR (CD₃CN): δ 1.43 (s, 3H, CH₃), 3.28 (br s, 1H, OH), 3.58 (m, 2H, H-5', H-5"), 3.99 (m, 1H, H-4'), 4.10 (br s, 1H, OH), 4.62 (d, 1H, $J_{2',1'}$=8.1 Hz, H-2'), 5.69 (d, 1H, H-1'), 5.88 (br s, 3H, OH, NH₂), 6.45 (br s, 1H, OH), 6.51 (d, 1H, $J_{5,6}$=3.7 Hz, H-5), 7.19 (d, 1H, H-6), 8.12 (s, 1H, H-2). ES-MS: 281 [MH]⁺.

EXAMPLE 36

2,4-Diamino-7-(2-C-methyl-β-D-ribofuranosyl)-7H-pyrrolo[2,3-d]pyrimidine

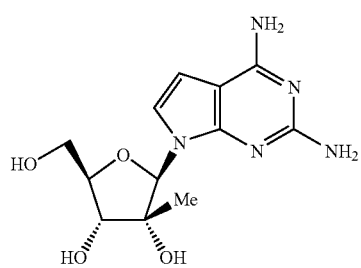

A mixture of the product from Step B of Example 4 (24 mg) in aqueous ammonia (30%, 10 mL) was heated in a stainless steel autoclave at 100° C. overnight, then cooled and evaporated. The residue was purified on a silica gel column with CH₂Cl₂/MeOH (10/1 and 5/1) as the eluent to afford the title compound (15 mg).

¹H NMR (DMSO-d₆): δ 0.68 (s, 3H, CH₃), 3.48-3.58 (m 1H, H-5'), 3.68-3.73 (m, 2H, H-5", H-4'), 3.84 (m, 1H, H-3'), 4.72 (s, 1H, 2'-OH), 4.97-5.03 (m, 2H, 3'-OH, 5'-OH), 5.45 (br s, 2H, NH₂), 6.00 (s, 1H, H-1'), 6.28 (d, 1H, J=3.7 Hz, H-5), 6.44 (br s, 2H, NH₂) 6.92 (d, 1H J=3.7 Hz, H-6). ES MS: 294.1 (M–H⁺).

EXAMPLE 37

4-Amino-2-fluoro-7-(2-C-methyl-β-D-ribofuranosyl)-7H-pyrrolo[2,3-d]pyrimidine

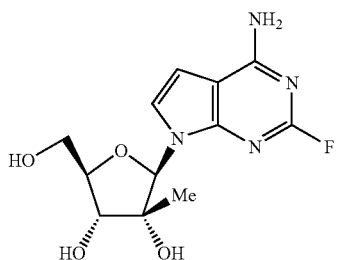

To a solution of HF/pyridine (70%, 2 mL) diluted with pyridine (1 mL) at −30° C. is added the compound of Example 36 (60 mg, 0.2 mmol) in 0.5 mL pyridine followed by tert-butyl nitrite (36 μL, 0.3 mmol). Stirring is continued for 5 min at −25° C. Then the solution is poured into ice-water (5 mL), neutralized with 2 N aqueous NaOH, and evaporated to dryness. The residue is purified on a silica gel column with CH₂Cl₂/MeOH (20/1 and 10/1) as the eluent to afford the title compound.

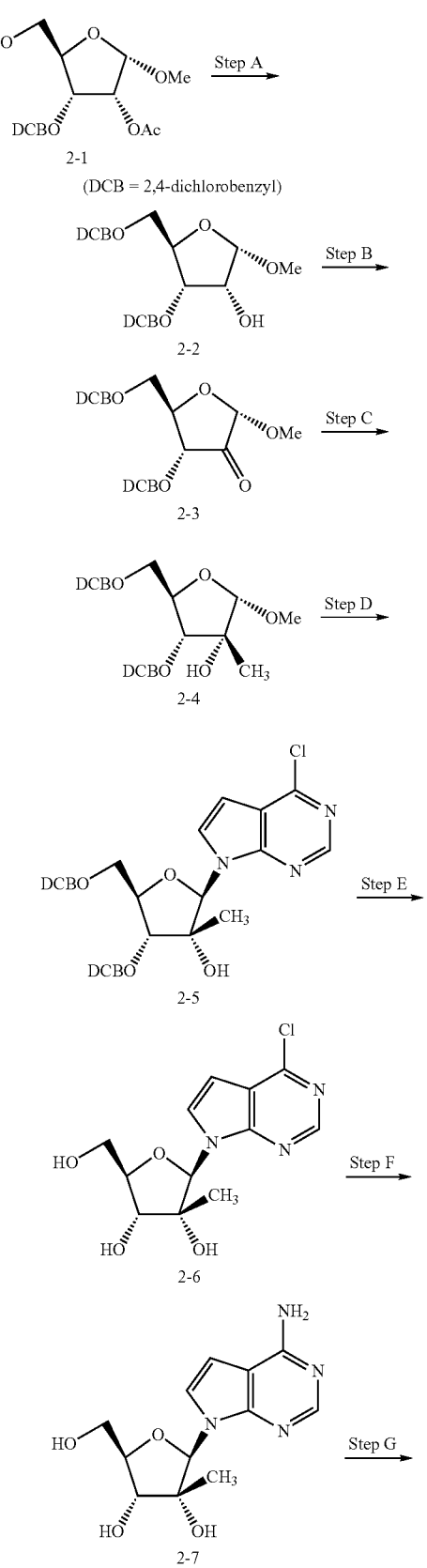

Scheme 2

(DCB = 2,4-dichlorobenzyl)

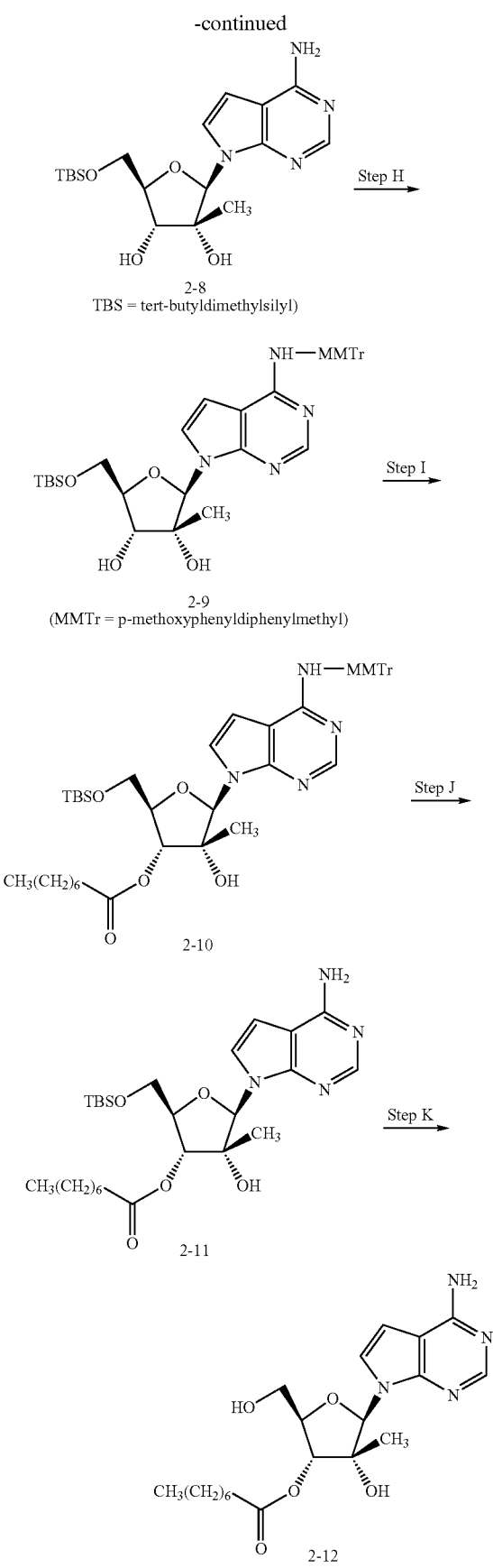

EXAMPLE 38

4-Amino-7-[2-C-methyl-3-O-(1-oxo-octyl -β-D-ribofuranosyl]-7H-pyrrolo[2,3-d]pyrimidine (2-12)

Step A: 3,5-Bis-O-(2,4-dichlorobenzyl)-1-O-methyl-α-D-ribofuranose (1-2)

A mixture of 2-O-acetyl-3,5-bis-O-(2,4-dichlorobenzyl)-1-O-methyl-α-D-ribofuranose (2-1) [for preparation, see: Helv. Chim. Acta 78: 486 (1995)](52.4 g, 0.10 mol) in methanolic $K_2CO_3$ (500 mL, saturated at room temperature) was stirred at room temperature for 45 min. and then concentrated under reduced pressure. The oily residue was suspended in $CH_2Cl_2$ (500 mL), washed with water (300 mL+5×200 mL) and brine (200 mL), dried ($Na_2SO_4$), filtered, and concentrated to give the title compound (49.0 g) as colorless oil, which was used without further purification in Step B below.

$^1$H NMR (DMSO-$d_6$): δ 3.28 (s, 3H, OCH$_3$), 3.53 (d, 2H, $J_{5,4}$=4.5 Hz, H-5a, H-5b), 3.72 (dd, 1H, $J_{3,4}$=3.6 Hz, $J_{3,2}$=6.6 Hz, H-3), 3.99 (ddd, 1H, $J_{2,1}$=4.5 Hz, $J_{2,OH-2}$=9.6 Hz, H-2), 4.07 (m, 1H, H-4), 4.50 (s, 2H, CH$_2$Ph), 4.52, 4.60 (2d, 2H, $J_{gem}$=13.6 Hz, CH$_2$Ph), 4.54 (d, 1H, OH-2), 4.75 (d, 1H, H-1), 7.32-7.45, 7.52-7.57 (2m, 10H, 2Ph). $^{13}$C NMR (DMSO-$d_6$) δ 55.40, 69.05, 69.74, 71.29, 72.02, 78.41, 81.45, 103.44, 127.83, 127.95, 129.05, 129.28, 131.27, 131.30, 133.22, 133.26, 133.55, 133.67, 135.45, 135.92.

Step B: 3,5-Bis-O-(2,4-dichlorobenzyl)-1-O-methyl-α-D-erythro-pentofuranos-2-ulose (2-3)

To an ice-cold suspension of Dess-Martin periodinane (50.0 g, 118 mmol) in anhydrous $CH_2Cl_2$ (350 mL) under argon (Ar) was added a solution of the compound from Step A (36.2 g, 75 mmol) in anhydrous $CH_2Cl_2$ (200 mL) dropwise over 0.5 h. The reaction mixture was stirred at 0° C. for 0.5 h and then at room temperature for 3 days. The mixture was diluted with anhydrous $Et_2O$ (600 mL) and poured into an ice-cold mixture of $Na_2S_2O_3.5H_2O$ (180 g) in saturated aqueous $NaHCO_3$ (1400 mL). The layers were separated, and the organic layer was washed with saturated aqueous $NaHCO_3$ (600 mL), water (800 mL) and brine (600 mL), dried ($MgSO_4$), filtered and evaporated to give the title compound (34.2 g) as a colorless oil, which was used without further purification in Step C below.

$^1$H NMR (CDCl$_3$): δ 3.50 (s, 3H, OCH$_3$), 3.79 (dd, 1H, $J_{5a,5b}$=11.3 Hz, $J_{5a,4}$=3.5 Hz, H-5a), 3.94 (dd, 1H, $J_{5b,4}$=2.3 Hz, H-5b), 4.20 (dd, 1H, $J_{3,1}$=1.3 Hz, $J_{3,4}$=8.4 Hz, H-3), 4.37 (ddd, 1H, H-4), 4.58, 4.69 (2d, 2H, $J_{gem}$=13.0 Hz, CH$_2$Ph), 4.87 (d, 1H, H-1), 4.78, 5.03 (2d, 2H, $J_{gem}$=12.5 Hz, CH$_2$Ph), 7.19-7.26, 7.31-7.42 (2m, 10H, 2Ph). $^{13}$C NMR (DMSO-$d_6$): δ 55.72, 69.41, 69.81, 69.98, 77.49, 78.00, 98.54, 127.99, 128.06, 129.33, 129.38, 131.36, 131.72, 133.61, 133.63, 133.85, 133.97, 134.72, 135.32, 208.21.

Step C: 3,5-Bis-O-(2,4-dichlorobenzyl)-2-C-methyl-1-O-methyl-α-D-ribofuranose (2-4)

To a solution of MeMgBr in anhydrous $Et_2O$ (0.48 M, 300 mL) at −55° C. was added dropwise a solution of the compound from Step B (17.40 g, 36.2 mmol) in anhydrous $Et_2O$ (125 mL). The reaction mixture was allowed to warm to −30° C. and stirred for 7 h at −30° C. to −15° C., then poured into ice-cold water (500 mL) and the mixture vigorously stirred at room temperature for 0.5 h. The mixture was filtered through a Celite pad (10×5 cm) which was thoroughly washed with $Et_2O$. The organic layer was dried (MgSO$_4$), filtered and concentrated. The residue was dissolved in hexanes (~30 mL), applied onto a silica gel column (10×7 cm, prepacked in hexanes) and eluted with hexanes and hexanes/EtOAc (9/1) to give the title compound (16.7 g) as a colorless syrup.

$^1$H NMR (CDCl$_3$): δ 1.36 (d, 3H, J$_{Me,OH}$=0.9 Hz, 2C-Me), 3.33 (q, 1H, OH), 3.41 (d, 1H, J$_{3,4}$=3.3 Hz), 3.46 (s, 3H, OCH$_3$), 3.66 (d, 2H, J$_{5,4}$=3.7 Hz, H-5a, H-5b), 4.18 (apparent q, 1H, H-4), 4.52 (s, 1H, H-1), 4.60 (s, 2H, CH$_2$Ph), 4.63, 4.81 (2d, 2H, J$_{gem}$=13.2 Hz, CH$_2$Ph), 7.19-7.26, 7.34-7.43 (2m, 10H, 2Ph). $^{13}$C NMR (CDCl$_3$): δ 24.88, 55.45, 69.95, 70.24, 70.88, 77.06, 82.18, 83.01, 107.63, 127.32, 129.36, 130.01, 130.32, 133.68, 133.78, 134.13, 134.18, 134.45, 134.58.

Step D: 4-Chloro-7-[3,5-bis-O-(2,4-dichlorobenzyl)-2-C-methyl-β-D-ribofuranosyl]-7H-pyrrolo[2,3-d]pyrimidine (2-5)

To a solution of the compound from Step C (9.42 g, 19 mmol) in anhydrous dichloromethane (285 mL) at 0° C. was added HBr (5.7 M in acetic acid, 20 mL, 114 mmol) dropwise. The resulting solution was stirred at 0° C. for 1 h and then at room temperature for 3h, evaporated in vacuo and co-evaporated with anhydrous toluene (3×40 mL). The oily residue was dissolved in anhydrous acetonitrile (50 mL) and added to a solution of sodium salt of 4-chloro-1H-pyrrolo[2,3-d]pyrimidine [for preparation, see *J. Chem. Soc.*, 131 (1960)] in acetonitrile [generated in situ from 4-chloro-1H-pyrrolo[2,3-d]pyrimidine (8.76 g, 57 mmol) in anhydrous acetonitrile (1000 mL), and NaH (60% in mineral oil, 2.28 g, 57 mmol), after 4 h of vigorous stirring at room temperature]. The combined mixture was stirred at room temperature for 24 h, and then evaporated to dryness. The residue was suspended in water (250 mL) and extracted with EtOAc (2×500 mL). The combined extracts were washed with brine (300 mL), dried over Na$_2$SO$_4$, filtered and evaporated. The crude product was purified on a silica gel column (10 cm×10 cm) using ethyl acetate/hexane (1:3 and 1:2) as the eluent. Fractions containing the product were combined and evaporated in vacuo to give the desired product (5.05 g) as a colorless foam.

$^1$H NMR (CDCl$_3$): δ 0.93 (s, 3H, CH$_3$), 3.09 (s, 1H, OH), 3.78 (dd, 1H, J$_{5',5''}$=10.9 Hz, J$_{5',4}$=2.5 Hz, H-5'), 3.99 (dd, 1H, J$_{5'',4}$=2.2 Hz, H-5''), 4.23-4.34 (m, 2H, H-3', H-4'), 4.63, 4.70 (2d, 2H, J$_{gem}$=12.7 Hz, CH$_2$Ph), 4.71, 4.80 (2d, 2H, J$_{gem}$=12.1 Hz, CH$_2$Ph), 6.54 (d, 1H, J$_{5,6}$=3.8 Hz, H-5), 7.23-7.44 (m, 10H, 2Ph). $^{13}$C NMR (CDCl$_3$): δ 21.31, 69.10, 70.41, 70.77, 79.56, 80.41, 81.05, 91.11, 100.57, 118.21, 127.04, 127.46, 127.57, 129.73, 129.77, 130.57, 130.99, 133.51, 133.99, 134.33, 134.38, 134.74, 135.21, 151.07, 151.15 152.47.

Step E: 4-Chloro-7-(2-C-methyl-β-D-ribofuranosyl)-7H-pyrrolo[2,3-d]pyrimidine (2-6)

To a solution of the compound from Step D (5.42 g, 8.8 mmol) in dichloromethane (175 mL) at −78° C. was added boron trichloride (1M in dichloromethane, 88 mL, 88 mmol) dropwise. The mixture was stirred at −78° C. for 2.5 h, then at −30° C. to −20° C. for 3 h. The reaction was quenched by addition of methanol/dichloromethane (1:1) (90 mL) and the resulting mixture stirred at −15° C. for 30 min., then neutralized with aqueous ammonia at 0° C. and stirred at room temperature for 15 min. The solid was filtered and washed with CH$_2$Cl$_2$/MeOH (1/1, 250 mL). The combined filtrate was evaporated, and the residue was purified by flash chromatography over silica gel using CH$_2$Cl$_2$ and CH$_2$Cl$_2$:MeOH (99:1, 98:2, 95:5 and 90: 10) gradient as the eluent to furnish desired compound (1.73 g) as a colorless foam, which turned into an amorphous solid after treatment with MeCN.

$^1$H NMR (DMSO-d$_6$): δ 0.64 (s, 3H, CH$_3$), 3.61-3.71 (m, 1H, H-5'), 3.79-3.88 (m, 1H, H-5''), 3.89-4.01 (m, 2H, H-3', H-4'), 5.15-5.23 (m, 3H, 2'-OH, 3'-OH, 5'-OH), 6.24 (s, 1H, H-1'), 6.72 (d, 1H, J$_{5,6}$=3.8 Hz, H-5), 8.13 (d, 1H, H-6), 8.65 (s, 1H, H-2). $^{13}$C NMR (DMSO-d$_6$): δ 20.20, 59.95, 72.29, 79.37, 83.16, 91.53, 100.17, 117.63, 128.86, 151.13, 151.19, 151.45.

Step F: 4-Amino-7-(2-C-methyl-β-D-ribofuranosyl)-7H-pyrrolo[2,3-d]pyrimidine (2-7)

To the compound from Step E (1.54 g, 5.1 mmol) was added methanolic ammonia (saturated at 0° C.; 150 mL). The mixture was heated in a stainless steel autoclave at 85° C. for 14 h, then cooled and evaporated in vacuo. The crude mixture was purified on a silica gel column with CH$_2$Cl$_2$/MeOH (9/1) as eluent to give the title compound as a colorless foam (0.8 g), which separated as an amorphous solid after treatment with MeCN. The amorphous solid was recrystallized from methanol/acetonitrile; m.p. 222° C.

$^1$H NM (DMSO-d$_6$): δ 0.62 (s, 3H, CH$_3$), 3.57-3.67 (m, 1H, H-5'), 3.75-3.97 (m, 3H, H-5'', H-4', H-3'), 5.00 (s, 1H, 2'-OH), 5.04 (d, 1H, J$_{3'OH,3}$=6.8 Hz, 3'-OH), 5.06 (t, 1H, J$_{5'OH,5',5''}$=5.1 Hz, 5'-OH), 6.11 (s, 1H, H-1'), 6.54 (d, 1H, J$_{5,6}$=3.6 Hz, H-5), 6.97 (br s, 2H, NH$_2$), 7.44 (d, 1H, H-6), 8.02 (s, 1H, H-2). $^{13}$C NMR (DMSO-d$_6$): δ 20.26, 60.42, 72.72, 79.30, 82.75, 91.20, 100.13, 103.08, 121.96, 150.37, 152.33, 158.15. LC-MS: Found: 279.10 (M–H$^+$); calc. for C$_{12}$H$_{16}$N$_4$O$_4$+H$^+$: 279.11.

Step G: 4-Amino-7-[5-O-(tert-butyldimethylsilyl)-2-C-methyl-β-D-ribofuranosyl]-7H-pyrrolo[2,3-d]pyrimidine (2-8)

To a solution of the compound from Step F (457 mg, 1.63 mmol) in anhydrous pyridine (3.5 mL) was added tert-butyldimethylsilyl chloride (370 mg, 2.45 mmol). The reaction mixture was stirred at room temperature for 24 h. The reaction mixture was then diluted with ethyl acetate (40 mL) which was washed with saturated aqueous sodium bicarbonate solution (20 mL). The organic layer was separated, dried over anhydrous sodium sulfate, filtered, and evaporated to an oil that was subjected to chromatography on silica gel eluting with 10% MeOH in CH$_2$C$_2$. The appropriate fractions were collected, evaporated, and dried under high vacuum to furnish the title compound as a colorless foam (516 mg).

$^1$H NMR (DMSO-d$_6$): δ 7.95 (s, 1H), 7.35 (d, 1H, J=3.4 Hz), 6.89 (bs, 2H, NH$_2$), 6.44 (d, 1H, J=3.4 Hz), 6.02 (s, 1H), 5.01-4.98 (m, 2H), 3.92-3.70 (m, 3H), 3.40-3.25 (m, 1H), 0.82 (s, 9H), 0.54 (s, 3H), 0.00 (s, 6H).

Step H: 4-(p-Methoxyphenyldiphenylmethylamino)-7-[5-O-(tert-butyldimethylsilyl)-2-C-methyl-β-D-ribofuranosyl]-7H-pyrrolo[2,3-d]pyrimidine (2-9)

To a solution of the compound from Step G (394 mg, 1.0 mmol) in anhydrous pyridine (5 mL) was added p-methoxyphenylchlorodiphenylmethane (946 mg, 3.06 mmol) and 4-dimethylaminopyridine (DMAP) (123 mg, 1.0 mmol). The reaction mixture was stirred at room temperature for 20 h. It was then diluted with ethyl acetate (30 mL) and washed with saturated aqueous sodium bicarbonate solution (3×15 mL) followed by water (2×15mL). The organic layer was dried over anhydrous Na$_2$SO$_4$ and concentrated to an oil. The crude product was purified using column chromatography on silica gel eluting with 5% MeOH in CH$_2$Cl$_2$. The appropriate fractions were collected and evaporated to give the title compound (540 mg).

$^1$H NMR (DMSO-d$_6$): δ 7.85 (s, 1H), 7.65 (s, 1H), 7.41 (d, 1H, J=3.8 Hz), 7.25-7.03 (m, 12H), 6.78 (d, 1H, J=3.6

Hz), 6.69 (d, 2H, J=9 Hz), 5.97 (s, 1H), 5.00-4.94 (m, 2H), 3.85-3.62 (m, 4H), 3.59 (s, 3H), 0.83 (s, 9H), 0.55 (s, 3H), 0.003 (s, 6H).

Step I: 4-(p-Methoxyphenyldiphenylmethylamino)-7-[5-O-(tert-butyldimethylsilyl)-3-O-(1-oxo-octyl)-2-C-methyl-β-D-ribofuranosyl]-7H-pyrrolo[2,3-d]pyrimidine (2-10)

To a solution of the compound from Step H (400 mg, 0.6 mmol) and anhydrous DMAP (73 mg, 0.6 mmol) in anhydrous $CH_2Cl_2$ (7 mL) was added slowly triethylamine (250 μL, 1.8 mmol). To the stirred solution was added octanoyl chloride (200 μL, 1.2 mmol) over 15 min. The reaction mixture was stirred for an additional 1.5 h. It was then diluted with methylene chloride (30 mL) and washed with saturated aqueous sodium bicarbonate solution (3×10 mL) and water (10 mL). The organic layer was dried over anhydrous sodium sulfate, filtered, and evaporated. The residue was subjected to column chromatography on silica gel eluting with 5% MeOH in $CH_2Cl_2$ to afford the title compound as a light yellow foam (340 mg).

$^1$H NMR (DMSO-$d_6$): δ 8.02 (s, 1H), 7.75 (s, 1H), 7.58 (d, 1H, J=3.6 Hz), 7.34-7.05 (m, 12H), 7.02 (d, 1H, J=3.6 Hz), 6.79 (d, 2H, J=9.0 Hz), 6.01 (s, 1H), 5.61 (s, 1H), 5.34 (d, 1H, J=9.0 Hz), 4.19-4.14 (m, 1H), 4.00-3.94 (m, 1H), 3.67-3.62 (m, 4H), 3.48-3.40 (m, 1H), 2.40-2.32 (m, 2H), 1.60-1.40 (m, 2H), 1.23 (bs, 8H), 0.91 (s, 9H), 0.84-0.80 (m, 3H), 0.67 (s, 3H), 0.07 (s, 6H).

Step J: 4-Amino-7-[5-O-(tert-butyldimethylsilyl)-3-O-(1-oxo-octyl)-2-C-methyl-β-D-ribofuranosyl]-7H-pyrrolo[2,3-d]pyrimidine (2-11)

A solution of the compound from Step I (250 mg, 0.31 mmol) in 6:3:1 MeOH:acetic acid:$H_2O$ (10 mL) was stirred at 50° C. for 12 h. The reaction mixture was then concentrated to dryness. The residue was diluted with ethyl acetate (30 mL) and washed with saturated aqueous sodium bicarbonate solution (3×15 mL) and water (2×10 mL). The organic layer was dried over anhydrous sodium sulfate, filtered, and evaporated. The crude product (200 mg) was used without further purification in Step K below. Further purification of a small amount was accomplished by silica gel column chromatography using 5% MeOH in $CH_2Cl_2$ as the eluent to give the title compound as a white foam.

$^1$H NMR (CDCl$_3$): δ 8.29 (s, 1H), 7.57 (d, 1H, J=3.8 Hz), 6.37 (d, 1H, J=3.8 HZ), 6.28 (s, 1H), 5.33-5.28 (m, 3H), 4.29-4.23 (m, 1H), 4.08-4.01 (m, 1H), 3.86-3.79 (m, 1H), 2.45-2.37 (m, 2H), 1.69-1.62 (m, 2H), 1.29-1.23 (m, 8H), 0.97-0.84 (m, 12H), 0.11 (s, 6H).

Step K: 4-Amino-7-[2-C-methyl-3-O-(1-oxo-octyl)-β-D-ribofuranosyl]-7H-pyrrolo[2,3-d]pyrimidine (2-12)

To a solution of the compound from Step J (230 mg, 0.44 mmol) in anhydrous THF (5 mL), was added triethylamine (300 μL, 2.14 mmol) and triethylamine trihydrofluoride (750 μL, 4.5 mmol). The solution was stirred overnight at room temperature. The reaction mixture was then diluted with ethyl acetate (30 mL) and washed with saturated aqueous sodium bicarbonate (3×10 mL) and water (10 mL). After drying the organic layer over anhydrous sodium sulfate and filtration, the solvent was evaporated. The resulting oil was purified on a silica gel column eluting with 1:1 acetone/$CH_2Cl_2$ followed by 10% MeOH in $CH_2Cl_2$. The appropriate fractions were concentrated and lyophilized to afford the title compound as a colorless powder (90 mg).

$^1$H NMR (CDCl$_3$): δ 8.30 (s, 1H), 7.31 (d, 1H, J=3.8 Hz), 6.39 (d, 1H, J=3.8 Hz), 6.16 (s, 1H), 5.44 (d, 1H, J=7.8 Hz), 5.23 (bs, 2H), 4.31-4.24 (m, 1H), 4.14-4.06 (m, 1H), 3.84- 3.76 (m, 1H), 2.48-2.40 (m, 2H), 1.80-1.50 (m, 3H), 1.34-1.23 (m, 7H), 0.95 (s, 3H), 0.88-0.55 (m, 3H).

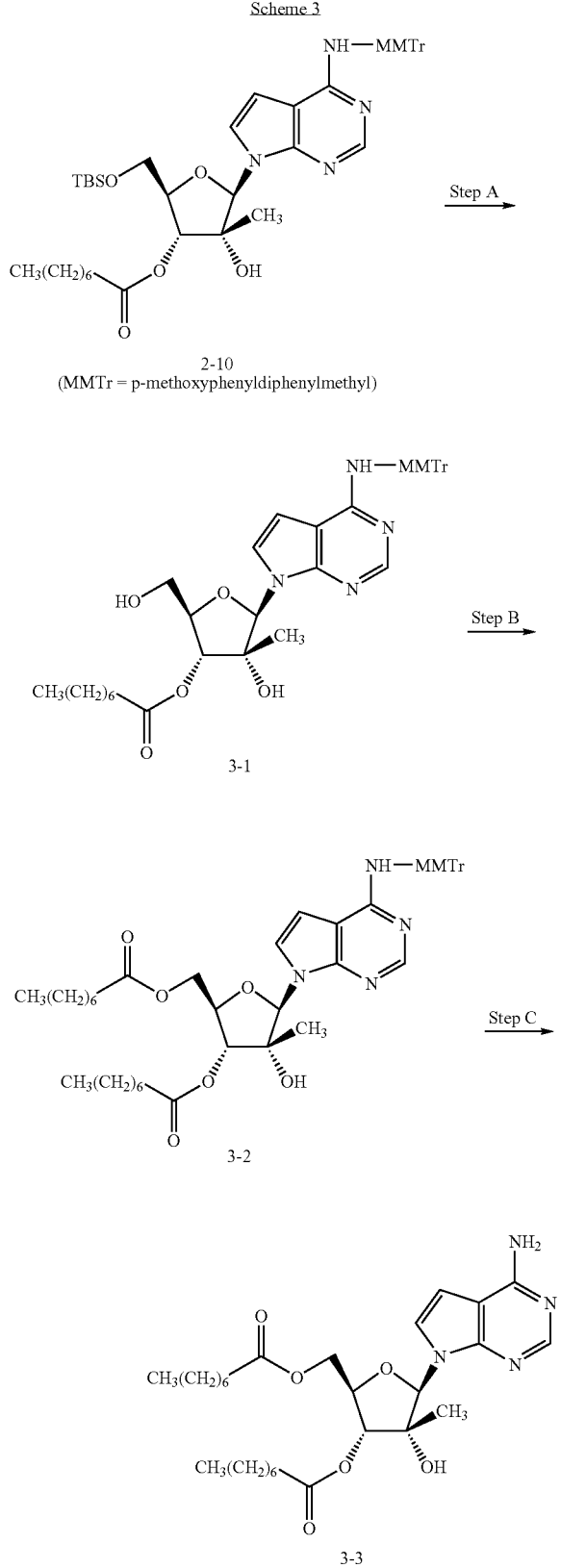

Scheme 3

EXAMPLE 39

4-Amino-7-[2-C-methyl-3,5-di-O-(1-oxo-octyl)-β-D-ribofuranosyl]-7H-pyrrolo[2,3-d]pyrimidine (3-3)

Step A: 4-(p-Methoxyphenyldiphenylmethylamino)-7-[3-O-(1-oxo-octyl)-2-C-methyl-β-D-ribofuranosyl]-7H-pyrrolo[2,3-d]pyrimidine (3-1)

A solution of the compound from Step I of Example 1 (1-10) (300 mg, 0.37 mmol), anhydrous triethylamine (300 μL, 2.14 mmol) and triethylamine trihydrofluoride (750 μL, 4.5 mmol) in anhydrous THF (5 mL) was stirred at room temperature overnight. The reaction mixture was diluted with ethyl acetate (50 mL) and washed with saturated aqueous sodium bicarbonate solution (3×20 mL) followed by water (2×15 mL). The organic layer was separated, dried over sodium sulfate, filtered, and evaporated. The crude product was purified on a silica gel column using 10-15% acetone in $CH_2Cl_2$ as the eluent. The appropriate fractions were combined and evaporated to afford the title compound as a colorless foam (240 mg).

$^1$H NMR (DMSO-$d_6$): δ 8.03 (s, 1H), 7.79 (s, 1H), 7.56 (d, 1H, J=3.8 Hz), 7.38-7.17 (m, 12H), 7.04 (d, 1H, J=3.8 Hz), 6.83 (d, 2H, J=9.0 Hz), 6.13 (s, 1H), 5.56 (s, 1H), 5.31 (d, 1H, J=9 Hz), 5.21-5.16 (m, 1H), 4.20-4.08 (m, 1H), 3.38-3.70 (m, 4H), 3.65-3.40 (m, 2H), 2.43-2.36 (m, 2H), 1.63-1.45 (m, 2H), 1.27 (bs, 8H), 0.91-0.84 (m, 3H), 0.74 (s, 3H).

Step B: 4-(p-Methoxyphenyldiphenylmethylamino)-7-[3,5-di-O-(1-oxo-octyl)-2-C-methyl-β-D-ribofuranosyl]-7H-pyrrolo[2,3-d]pyrimidine (3-2)

A solution of the compound from Step B (18 mg, 0.026 mmol) and DMAP (3.5 mg, 0.028 mmol) in anhydrous $CH_2Cl_2$ (300 μL) was cooled in an ice bath for 10 minutes under an argon atmosphere. To this solution was added triethylamine (7.5 μL, 0.053 mmol) followed by octanoyl chloride (6.6 μL, 0.038 mmol). The reaction mixture was stirred at this temperature for 2 h, diluted with $CH_2Cl_2$ (20 mL) and washed with saturated aqueous sodium bicarbonate solution (2×10 mL) followed by water (10 mL). The crude product obtained after evaporation was purified by column chromatography on silica gel eluting with 10% acetone in $CH_2Cl_2$. The title compound was obtained as a colorless foam (13.5 mg).

Step C: 4-Amino-7-[2-C-methyl-3,5-di-O-(1-oxo-octyl)-(β-D-ribofuranosyl]-7H-pyrrolo[2,3-d]pyrimidine (3-3)

A solution of the compound from Step B (13 mg, 0.016 mmol) in 6:3:1 MeOH: acetic acid: $H_2O$ (500 μL) was stirred at 50° C. for 15 h. The reaction mixture was then concentrated to dryness. The residue was diluted with ethyl acetate (15 mL) and washed with saturated aqueous sodium bicarbonate solution (3×5 mL) and water (2×5 mL). The organic layer was dried over anhydrous sodium sulfate, filtered, and evaporated. The crude product was purified by silica gel column chromatography eluting with 10% acetone in dichloromethane to afford the title compound as a white foam (6.0 mg).

$^1$H NMR (CDCl$_3$): δ 8.29 (s, 1H), 7.25 (d, 1H, J=3.4 Hz), 6.40 (d, 1H, J=4.0 Hz), 6.23 (s, 1H), 5.22-5.39 (m, 3H), 4.60-4.39 (m, 4H), 2.47-2.35 (m, 4H), 1.82-1.60 (m, 4H), 1.27 (bs, 16H), 0.87 (s, 3H), 0.873-0.80 (m, 6H).

Scheme 4

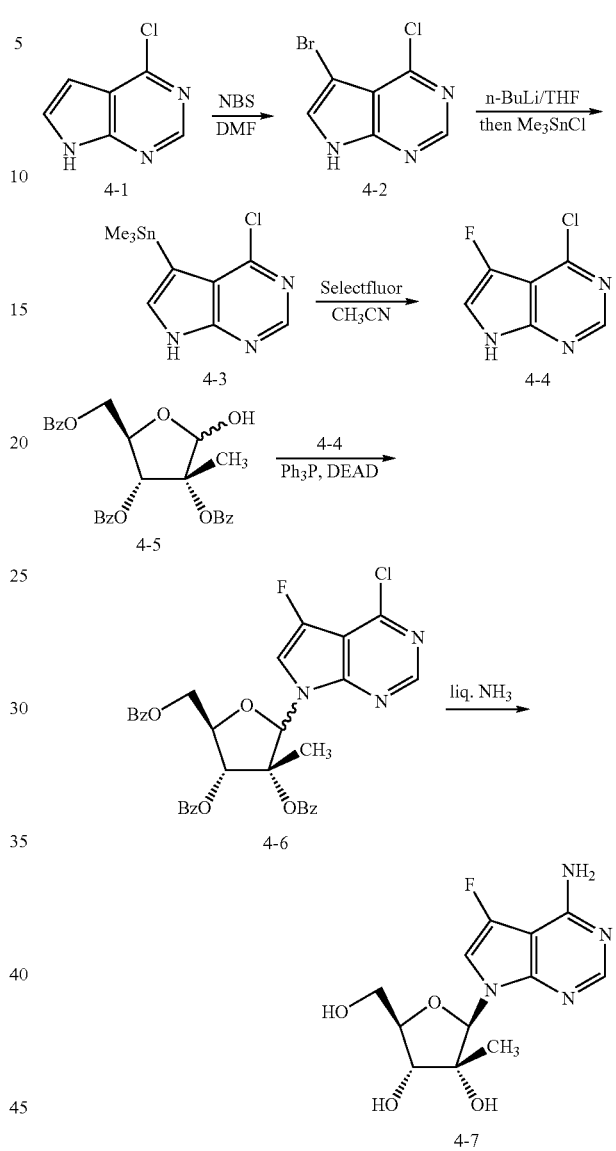

EXAMPLE 40

4-Amino-5-fluoro-7-(2-C-methyl-β-D-ribofuranosyl)-7H-pyrrolo[2,3-d]pyrimidine (4-7)

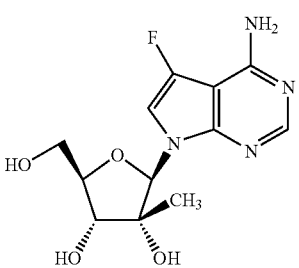

Step A: 5-Bromo-4-chloro-7H-pyrrolo[2,3-d]pyrimidine (4-2)

To a solution of 4-chloro-7H-pyrrolo[2,3-d]pyrimidine (4-1) (1.53 g, 10.0 mmol) in DMF (20 mL) was added N-bromosuccinimide (1.78 g, 10.0 mmol) in DMF (10 mL) dropwise at 0° C. The reaction mixture was stirred at 0° C. for 30 min and then at room temperature for 1 h. Methanol (25 mL) was added, and the reaction mixture was stirred for an additional 1 h. The solvent was evaporated and the residue was crystallized from methanol to give the title compound as white solid.

Step B: 5-(Trimethylstannyl)-4-chloro-7H-pyrrolo[2,3-d]pyrimidine (4-3)

To a solution of the compound from Step A (0.92 g, 4 mmol) in THF (25 mL) was added n-BuLi (2.5 M solution in hexane, 3.48 mL) dropwise at −78° C. After the addition, the reaction mixture was stirred at −78° C. for an additional 30 min. To this solution was added trimethyltin chloride (0.88 g, 4.4 mmol) in THF (8 mL) dropwise for a period of 10 min. The reaction mixture was brought to room temperature slowly and stirred at room temperature overnight. Saturated aqueous ammonium chloride (60 mL) was added and extracted with ethyl acetate (3×70 mL). The combined organic extracts were washed with brine, dried over $Na_2SO_4$, and evaporated to dryness. The residue was purified over silica gel to give the title compound as a colorless solid.

Step C: 5-Fluoro-4-chloro-7H-pyrrolo[2,3-d]pyrimidine (4-4)

To a solution of the compound from Step B (1.97 g, 6.20 mmol) in $CH_3CN$ (60 mL) was added [1-(chloromethyl)-4-fluoro-1,4-diazoniabicyclo[2.2.2]octane bis(tetrafluoroborate)] (SELECTFLUOR® fluorinating reagent) (2.40 g, 6.5 mmol) in one portion and the reaction mixture was stirred at room temperature for 7 h. The white precipitate was filtered off, and the filtrate was evaporated to dryness. The residue was purified over silica gel using ethyl acetate/hexane (3:7) as the eluent. Fractions containing the product were pooled and eveporated in vacuo to give the title compound as a colorless solid.

$^1$H-NMR (MeOH-d$_4$): δ 8.53 (s, 1H), 7.37 (d, J=2.8 Hz); $^{19}$F-NMR (DMSO-d$_6$): δ-171.5.

Step D: 4-Amino-5-fluoro-7-(2-C-methyl-β-D-ribofuranosyl)-7H-pyrrolo[2,3-d]pyrimidine (4-7)

To a solution of the compound from Step C (0.075 g, 0.44 mmol), 2,3,5-tri-O-benzoyl-2-C-methyl-D-ribofuranose [Harry-O'kuru, Rogers E.; Smith, Jennifer M.; Wolfe, Michael S, "A Short, Flexible Route toward 2'-C-Branched Ribonucleosides," *J. Org. Chem.*, 62: 1754-1759 (1997)] (4-5) (0.25 g, 0.53 mmol) and triphenylphosphine (0.23 g, 0.88 mmol) in THF (15 mL) was added diethyl azodicarboxylate (DEAD) (0.14 mL, 0.88 mmol). The reaction mixture was stirred at room temperature overnight. The solution was directly adsorbed onto silica gel and purified over silica gel using ethyl acetate/hexane 1:9 as the eluent Appropriate fractions were dissolved in dioxane (3 mL) and liquid ammonia (4 mL) and the mixture was heated in a steel bomb at 85° C. for 24 h. The solvent was evaporated and the residue was purified over silica gel using methanol/dichloromethane (1:9) as the eluent. Fractions containing the desired compound were pooled and evaporated in vacuo to give the title compound.

$^1$H-NMR (MeOH-d$_4$): δ 8.07 (s, 1H), 7.41 (d, J=2.2 Hz, 1H), 6.25 (d, J=1.8 Hz), 4.09-3.95 (m, 3H), 3.82 (dd, J=2.7, 12.5 Hz, 1H); $^{19}$F-NMR (MeOH-d$_4$): δ-170.4; mass spectrum: 321 (M+Na)$^+$.

EXAMPLE 41

6-Amino-2-fluoro-9-(2-C-methyl-β-D-ribofuranosyl)purine

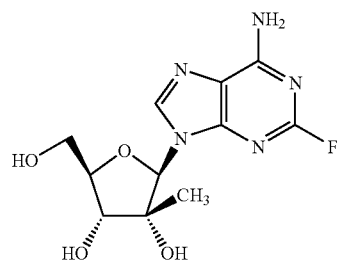

Step A: 2-Amino-6-chloro-9-(2,3,5-tri-O-benzoyl-2-C-methyl-β-D-ribofuranosyl)purine To a pre-cooled solution of 1,2,3,5-tetra-O-benzoyl-2-C-methyl-D-ribofuranose [Harry-O'kuru, Rogers E.; Smith, Jennifer M.; Wolfe, Michael S, "A Short, Flexible Route toward 2'-C-Branched Ribonucleosides," *J. Org. Chem.*, 62:1754-1759 (1997)] (1.74 g, 3.00 mmol) in acetonitrile (15 mL) was added 2-amino-6-chloropurine (0.56 g, 3.30 mmol), then diazabicyclo[5.4.0]undec-7-ene (DBU) (1.37 g, 9.00 mmol), and then dropwise trimethylsilylmethyl trifluoromethanesulfonate (TMS trifate) (2.67 g, 12.00 mmol). The resulting mixture was heated to 65° C. for 4 h, then cooled and partitioned between saturated aqueous sodium bicarbonate (200 mL) and dichloromethane (200 mL). The organic phase was dried over magnesium sulfate, filtered and evaporated in vacuo. The resulting crude product was used directly in step B.

Step, B: 2-Amino-6-chloro-9-(2-C-methyl-β-D-ribofuranosyl)purine

To the crude compound from Step A (2.54 g) in THF (18 mL) was added aqueous 2N LiOH (6 mL). The resulting mixture was stirred at room temperature for 3 h, the THF evaporated in vacuo and the resulting aqueous phase neutralized by addition of aqueous 2N hydrochloric acid. The mixture was adsorbed onto silica gel by evaporation in vacuo and purified on silica gel using methanol/dichloromethane (1:4) as the eluent. Fractions containing the product were combined and evaporated in vacuo to give the desired product as a colorless powder.

Step C: 2,6-Diamino-9-(2-C-methyl-β-D-ribofuranosyl)purine

To the compound from Step B (100 mg) was added ammonium hydroxide (5 mL) and the resulting mixture was stirred at 80° C. in a Parr bomb overnight. The mixture was cooled and evaporated in vacuo and adsorbed onto silica and purified on silica gel using methanol/dichloromethane (1:4) as the eluent. Fractions containing the product were combined and evaporated in vacuo to give the desired product as a colorless powder.

Step D: 6-Amino-2-fluoro-9-(2-C-methyl-β-D-ribofuranosyl)purine

To a mixture of HF/pyridine (70%) (1 mL) in pyridine (1 mL) at −30° C. was added the compound from Step C (29.6 mg, 0.10 mmol) in pyridine (0.5 mL), followed by addition of tert-butyl nitrite (0.018 mL, 0.15 mmol). The mixture was stirred for 5 minutes and then poured into ice water (5 mL), neutralized with 2N NaOH and evaporated in vacuo. The crude product was purified on silica gel using methanol/dichloromethane (1:9 through 1:4) as the eluent. Fractions containing the desired product were pooled and evaporated in vacuo to give the desired compound as a colorless oil.

$^1$H-NMR (acetonitrile-d$_3$): δ 8.23 (s, 1H), 5.93 (s, 1H), (t, J=8.4 Hz, 1H), 4.00 (m, 2H), 3.81 (m, 1H), 3.70 (s, 1H), 3.60 (m, 1H), 0.90 (s, 3H). $^{19}$F-NMR (MeOH-d$_4$): −80; Mass spectrum: 298.3 (M−H)$^+$ and 597.1 (2M−H)$^+$.

Biological Assays

The assays employed to measure activity against vaccinia virus are described below:

a. Determination of In Vitro Antiviral Activity of Compounds Against Vaccinia Virus (Cytopathic Effect Inhibition Assay):

Assay conditions are described in the article by Sidwell and Huffman, "Use of disposable microtissue culture plates for antiviral and interferon induction studies," *Appl. Microbiol.* 22: 797-801 (1971).

Vaccinia virus, Lederle strain from the ATCC, was used with Vero cells and media (9% fetal bovine serum, 0.1% NaHCO$_3$, no antibiotics) as stated in the article. Antiviral test medium was MEM with 2% FBS and 0.18% NaHCO$_3$.

Four and seven point titrations were used to assay compound inhibition. Final compound concentrations for 4-point titrations were 100, 10, 1, and 0.1 µM. Seven-point titrations were performed by preparing one-half log serial dilutions from maximum compound concentrations of either 100 µM or 320 µM. Virus was added to the assay plate approximately 5 min after the test compound. Assay plates were incubated with humidified air and 5% CO$_2$ at 37° C. Cytotoxicity was monitored in the control cells microscopically for morphologic changes. Regression analysis of the virus CPE data and the toxicity control data gave the ED50 (50% effective dose) and CC50 (50% cytotoxic concentration). The selectivity index (SI) was calculated by the formula: SI=CC50÷ED50.

(S)-1-[3-hydroxy-2-(phosphonylmethoxy)-propyl]cytosine (cidofovir) was used as a positive control for anti-vaccinia virus testing.

Representative compounds tested in the anti-vaccinia virus assay exhibited EC$_{50}$'s less than 100 micromolar.

b. Determination of In Vitro Antiviral Activity of Compounds Against Vaccinia Virus (Neutral Red Uptake Assay)

After performing the CPE inhibition assay above, an additional cytopathic detection method was used. McManus described the detection method in "Microtiter Assay for Interferon: Microspectrophotometric Quantitation of Cytopathic Effect," *Appl. Environ. Microbiol.*, 31: 35-38 (1976). A Model EL309 microplate reader (Bio-Tek Instruments Inc.) was used at 540 nm to directly read the assay plate. ED50 and CD50 were calculated as above.

The nucleoside derivatives of the present invention were also evaluated for cellular toxicity and antiviral specificity in the counterscreens described below.

Counterscreens:

The ability of the nucleoside derivatives of the present invention to inhibit human DNA polymerases was measured in the following assays.

a. Inhibition of Human DNA Polymerases Alpha and Beta:

Reaction Conditions:
50 µL reaction volume

Reaction Buffer Components:
20 mM Tris-HCl, pH 7.5
200 µg/mL bovine serum albumin
100 mM KCl
2 mM β-mercaptoethanol
10 mM MgCl$_2$
1.6 µM dATP, dGTP, dCTP, dTTP
α-$^{33}$P-dATP Enzyme and template:
0.05 mg/mL gapped fish sperm DNA template
0.01 U/µL DNA polymerase α or β

Preparation of Gapped Fish Sperm DNA Template:
Add 5 µL 1M MgCl$_2$ to 500 µL activated fish sperm DNA (USB 70076);
Warm to 37° C. and add 30 µL of 65 U/µL of exonuclease m (GibcoBRL 18013-011);
Incubate 5 min at 37° C.;
Terminate reaction by heating to 65° C. for 10 min;
Load 50-100 µL aliquots onto Bio-spin 6 chromatography columns (Bio-Rad 732-6002) equilibrated with 20 mM Tris-HCl, pH 7.5;
Elute by centrifugation at 1,000×g for 4 min;
Pool eluate and measure absorbance at 260 nm to determine concentration.

The DNA template was diluted into an appropriate volume of 20 mM Tris-HCl, pH 7.5 and the enzyme was diluted into an appropriate volume of 20 mM Tris-HCl, containing 2 mM β-mercaptoethanol, and 100 mM KCl. Template and enzyme were pipetted into microcentrifuge tubes or a 96 well plate. Blank reactions excluding enzyme and control reactions excluding test compound were also prepared using enzyme dilution buffer and test compound solvent, respectively. The reaction was initiated with reaction buffer with components as listed above. The reaction was incubated for 1 h at 37° C. The reaction was quenched by the addition of 20 µL 0.5M EDTA. 50 µL of the quenched reaction was spotted onto Whatman DE81 filter disks and air dried. The filter disks were repeatedly washed with 150 mL 0.3M ammonium formate, pH 8 until 1 mL of wash is <100 cpm. The disks were washed twice with 150 mL absolute ethanol and once with 150 mL anhydrous ether, dried and counted in 5 mL scintillation fluid.

The percentage of inhibition was calculated according to the following equation: % inhibition=[1−(cpm in test reaction−cpm in blank)/(cpm in control reaction−cpm in blank)]×100.

b. Inhibition of Human DNA Polymerase Gamma:

The potential for inhibition of human DNA polymerase gamma was measured in reactions that included 0.5 ng/µL enzyme; 10 µM dATP, dGTP, dCTP, and TTP; 2 µCi/reaction [α-$^{33}$P]-dATP, and 0.4 µg/µL activated fish sperm DNA (purchased from US Biochemical) in a buffer containing 20 mM Tris pH8, 2 mM β-mercaptoethanol, 50 mM KCl, 10 mM MgCl$_2$, and 0.1 µg/µL BSA. Reactions were allowed to proceed for 1 h at 37° C. and were quenched by addition of 0.5 M EDTA to a final concentration of 142 mM. Product formation was quantified by anion exchange filter binding and scintillation counting. Compounds were tested at up to 50 µM.

The percentage of inhibition was calculated according to the following equation: % inhibition=[1−(cpm in test reaction−cpm in blank)/(cpm in control reaction−cpm in blank)]×100.

The ability of the purine nucleoside derivatives of the present invention to inhibit HIV infectivity and HIV spread was measured in the following assays.

c. HIV Infectivity Assay

Assays were performed with a variant of HeLa Magi cells expressing both CXCR4 and CCR5 selected for low background β-galactosidase (β-gal) expression. Cells were infected for 48 h, and β-gal production from the integrated HIV-1 LTR promoter was quantified with a chemiluminescent substrate (Galactolight Plus, Tropix, Bedford, Mass.). Inhibitors were titrated (in duplicate) in twofold serial dilutions starting at 100 μM; percent inhibition at each concentration was calculated in relation to the control infection.

d. Inhibition of HIV Spread

The ability of the compounds of the present invention to inhibit the spread of the human immunodeficiency virus (HIV) was measured by the method described in U.S. Pat. No. 5,413,999 (May 9, 1995), and J. P. Vacca, et al., *Proc. Natl. Acad. Sci.*, 91: 4096-4100 (1994), which are incorporated by reference herein in their entirety.

The nucleoside derivatives of the present invention were also screened for cytotoxicity against cultured hepatoma (HuH-7) cells containing a subgenomic HCV Replicon in an MTS cell-based assay as described in the assay below. The HuH-7 cell line is described in H. Nakabayashi, et al., *Cancer Res.*, 42: 3858 (1982).

e. Cytotoxicity Assay:

Cells were plated at 15-20,000 cells/well in 100 μL of appropriate media and incubated 18 h at 37° C., 5% $CO_2$. 100 μL of compound diluted in complete media was added to the cells for a final of 1% DMSO concentration. The plates were incubated at 37° C. and 5% $CO_2$ for 24 h. After the incubation period, 40 μL of CellTiter 96 Aqueous One Solution Cell Proliferation Assay reagent (MTS) (Promega) was added to each well, and the plates were incubated at 37° C. and 5% $CO_2$ for 1 h. The plates were agitated to mix well and absorbance at 490 nm was read using a plate reader. Metabolically active cells reduce MTS to formazan. Formazan absorbs at 490 nm. The absorbance at 490 nm in the presence of compound was compared to absorbance in cells without any compound added.

Reference: Cory, A. H. et al., "Use of an aqueous soluble tetrazolium/formazan assay for cell growth assays in culture," *Cancer Commun.* 3: 207 (1991).

Example of a Pharmaceutical Formulation

As a specific embodiment of an oral composition of a compound of the present invention, 50 mg of the compound of Example 2 is formulated with sufficient finely divided lactose to provide a total amount of 580 to 590 mg to fill a size O hard gelatin capsule.

While the invention has been described and illustrated in reference to specific embodiments thereof, those skilled in the art will appreciate that various changes, modifications, and substitutions can be made therein without departing from the spirit and scope of the invention. For example, effective dosages other than the preferred doses as set forth hereinabove may be applicable as a consequence of variations in the responsiveness of the human being treated for severity of the HCV infection. Likewise, the pharmacologic response observed may vary according to and depending upon the particular active compound selected or whether there are present pharmaceutical carriers, as well as the type of formulation and mode of administration employed, and such expected variations or differences in the results are contemplated in accordance with the objects and practices of the present invention. It is intended therefore that the invention be limited only by the scope of the claims which follow and that such claims be interpreted as broadly as is reasonable.

What is claimed is:

1. A method of inhibiting orthopoxvirus replication comprising administering to a mammal in need of such treatment a therapeutically effective amount of a compound of structural formula I:

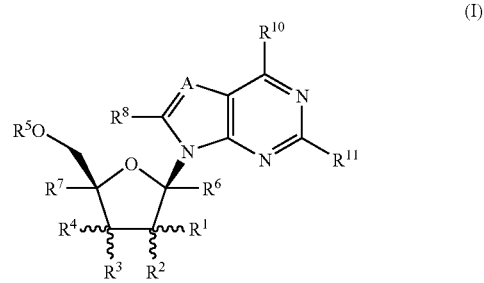

or a pharmaceutically acceptable salt thereof; wherein

A is N or C-$R^9$;

$R^1$ is $C_{2-4}$ alkenyl, $C_{2-4}$ alkynyl, or $C_{1-4}$ alkyl, wherein alkyl is unsubstituted or substituted with hydroxy, amino, $C_{1-4}$ alkoxy, $C_{1-4}$ alkylthio, or one to three fluorine atoms;

$R^2$ is amino, fluorine, hydroxy, $C_{1-10}$ alkylcarbonyloxy, mercapto, or $C_{1-4}$ alkoxy;

$R^3$ and $R^4$ are each independently selected from the group consisting of hydrogen, cyano, azido, halogen, hydroxy, $C_{1-16}$ alkylcarbonyloxy, $C_{2-18}$ alkenylcarbonyloxy, $C_{1-10}$ alkyloxycarbonyloxy, $C_{3-6}$ cycloalkylcarbonyloxy, $C_{3-6}$ cycloalkyloxycarbonyloxy, mercapto, amino, $C_{1-4}$ alkoxy, $C_{2-4}$ alkenyl, $C_{2-4}$ alkynyl, and $C_{1-4}$ alkyl, wherein alkyl is unsubstituted or substituted with hydroxy, amino, $C_{1-4}$ alkoxy, $C_{1-4}$ alkylthio, or one to three fluorine atoms;

$R^5$ is hydrogen, $C_{1-6}$ alkylcarbonyl, $C_{2-18}$ alkenylcarbonyl, $C_{1-10}$ alkyloxycarbonyl, $C_{3-6}$ cycloalkylcarbonyl, $C_{3-6}$ cycloalkyloxycarbonyl, $P_3O_9H_4$, $P_2O_6H_3$, or P(O)$R^{13}R^{14}$;

$R^6$ and $R^7$ are each independently hydrogen, methyl, hydroxymethyl, or fluoromethyl;

$R^8$ is hydrogen, $C_{1-4}$ alkyl, $C_{2-4}$ alkynyl, halogen, cyano, carboxy, $C_{1-4}$ alkyloxycarbonyl, azido, amino, $C_{1-4}$ alkylamino, di($C_{1-4}$ alkyl)amino, hydroxy, $C_{1-6}$ alkoxy, $C_{1-6}$ alkylthio, $C_{1-6}$ alkylsulfonyl, or ($C_{1-4}$ alkyl)$_{0-2}$ aminomethyl;

$R^9$ is hydrogen, cyano, nitro, $NHCONH_2$, $CONR^{12}R^{12}$, $CSNR^{12}R^{12}$, $COOR^{12}$, C(=NH)$NH_2$, hydroxy, $C_{1-3}$ alkoxy, amino, $C_{1-4}$ alkylamino, di($C_{1-4}$ alkyl)amino, halogen, or $C_{1-3}$ alkyl, wherein alkyl is unsubstituted or substituted with one to three groups independently selected from halogen, amino, hydroxy, carboxy, and $C_{1-3}$ alkoxy;

$R^{10}$ and $R^{11}$ are each independently hydrogen, hydroxy, mercapto, halogen, $C_{1-4}$ alkoxy, $C_{1-4}$ alkylthio, amino, $C_{1-4}$ alkylamino, di($C_{1-4}$ alkyl)amino, $C_{3-6}$ cycloalkylamino, di($C_{3-6}$ cycloalkyl)amino, phenyl-$C_{1-2}$ alkylamino, $C_{1-4}$ acylamino, $C_{1-8}$ alkylcarbonyloxy, or $OCH(C_{1-4}\ alkyl)O(C{=}O)C_{1-4}$ alkyl;

each $R^{12}$ is independently hydrogen or $C_{1-6}$ alkyl; and $R^{13}$ and $R^{14}$ are each independently hydroxy, $OCH_2CH_2SC({=}O)C_{1-4}$ alkyl, $OCH_2O(C{=}O)OC_{1-4}$ alkyl, $NHCHMeCO_2Me$, $OCH(C_{1-4}\ alkyl)O(C{=}O)C_{1-4}$ alkyl,

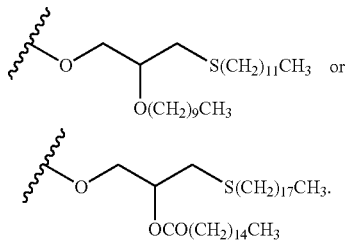

or

2. A method of treating orthopoxvirus infection in a mammal in need thereof comprising administering a therapeutically effective amount of a compound of claim 1.

3. The method of claim 1 wherein the compound is of structural formula II:

(II)

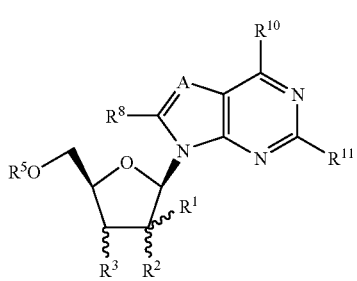

or a pharmaceutically acceptable salt thereof; wherein

A is N or C—$R^9$;

$R^1$ is $C_{1-3}$ alkyl, wherein alkyl is unsubstituted or substituted with hydroxy, amino, $C_{1-3}$ alkoxy, $C_{1-3}$ alkylthio, or one to three fluorine atoms;

$R^2$ is hydroxy, $C_{1-16}$ alkylcarbonyloxy, fluoro, or $C_{1-3}$ alkoxy;

$R^3$ is hydrogen, halogen, hydroxy, $C_{1-16}$ alkylcarbonyloxy, amino, or $C_{1-3}$ alkoxy;

$R^5$ is hydrogen, $C_{1-16}$ alkylcarbonyl, $P_3O_9H_4$, $P_2O_6H_3$, or $PO_3H_2$;

$R^8$ is hydrogen, amino, or $C_{1-4}$ alkylamino;

$R^9$ is hydrogen, cyano, methyl, halogen, or $CONH_2$; and $R^{10}$ and $R^{11}$ are each independently hydrogen, halogen, hydroxy, amino, $C_{1-4}$ alkylamino, di($C_{1-4}$ alkyl)amino, or $C_{3-6}$ cycloalkylamino.

4. The method of claim 3 wherein $R^1$ is methyl, fluoromethyl, hydroxymethyl, difluoromethyl, trifluoromethyl, or aminomethyl;

$R^2$ is hydroxy, $C_{1-16}$ alkylcarbonyloxy, fluoro, or methoxy;

$R^3$ is hydrogen, fluoro, hydroxy, $C_{1-16}$ alkylcarbonyloxy, amino, or methoxy;

$R^5$ is hydrogen, $C_{1-16}$ alkylcarbonyl, or $P_3O_9H_4$;

$R^8$ is hydrogen or amino;

$R^9$ is hydrogen, cyano, methyl, halogen, or $CONH_2$; and $R^{10}$ and $R^{11}$ are each independently hydrogen, halogen, hydroxy, amino, $C_{1-4}$ alkylamino, di($C_{1-4}$ alkyl)amino, or $C_{3-6}$ cycloalkylamino.

5. The method of claim 4 wherein the compound is selected from the group consisting of:

4-amino-7-(2-C-methyl-β-D-ribofuranosyl)-7H-pyrrolo[2,3-d]pyrimidine, 4-methylamino-7-(2-C-methyl-β-D-ribofuranosyl)-7H-pyrrolo[2,3-d]pyrimidine, 4-dimethylamino-7-(2-C-methyl-β-D-ribofuranosyl)-7H-pyrrolo[2,3-d]pyrimidine, 4-cyclopropylamino-7-(2-C-methyl-β-D-ribofuranosyl)-7H-pyrrolo[2,3-d]pyrimidine, 4-amino-7-(2-C-hydroxymethyl-β-D-ribofuranosyl)-7H-pyrrolo[2,3-d]pyrimidine, 4-amino-7-(2-C-fluoromethyl-β-D-ribofuranosyl)-7H-pyrrolo[2,3-d]pyrimidine, 4-amino-5-methyl-7-(2-C-methyl-β-D-ribofuranosyl)-7H-pyrrolo[2,3-d]pyrimidine, 4-amino-7-(2-C-methyl-β-D-ribofuranosyl)-7H-pyrrolo[2,3-d]pyrimidine-5-carboxamide, 4-amino-7-(2-C-methyl-β-D-ribofuranosyl)-7H-pyrrolo[2,3-d]pyrimidine-5-carbonitrile, 4-amino-5-bromo-7-(2-C-methyl-β-D-ribofuranosyl)-7H-pyrrolo[2,3-d]pyrimidine, 4-amino-5-chloro-7-(2-C-methyl-β-D-ribofuranosyl)-7H-pyrrolo[2,3-d]pyrimidine, 4-amino-5-fluoro-7-(2-C-methyl-β-D-ribofuranosyl)-7H-pyrrolo[2,3-d]pyrimidine, 2,4-diamino-7-(2-C-methyl-β-D-ribofuranosyl)-7H-pyrrolo[2,3-d]pyrimidine, 2-amino-7-(2-C-methyl-β-D-ribofuranosyl)-7H-pyrrolo[2,3-d]pyrimidine, 2-amino-4-cyclopropylamino-7-(2-C-methyl-β-D-ribofuranosyl)-7H-pyrrolo[2,3-d]pyrimidine, 2-amino-7-(2-C-methyl-β-D-ribofuranosyl)-7H-pyrrolo[2,3-d]pyrimidin-4(3H)-one, 7-(2-C-methyl-β-D-ribofuranosyl)-7H-pyrrolo[2,3-d]pyrimidin-4(3H)-one, 4-amino-2-fluoro-7-(2-C-methyl-β-D-ribofuranosyl)-7H-pyrrolo[2,3-d]pyrimidine, 9-(2-C-methyl-β-D-ribofuranosyl)-2-amino-6-hydroxy-purine, 9-(2-C-methyl-β-D-ribofuranosyl)-2-amino-6-cyclopropylaminopurine, 9-(2-C-methyl-β-D-ribofuranosyl)-2,6-diaminopurine, 9-(2-C-methyl-β-D-ribofuranosyl)-2-amino-6-methylaminopurine, 6-amino-2-fluoro-9-(2-C-methyl-β-D-ribofuranosyl)purine, 2'-C-methyl-adenosine, 4-amino-7-[2-C-methyl-3-O-(1-oxo-octyl)-β-D-ribofuranosyl]-7H-pyrrolo[2,3-d]pyrimidine, and 4-amino-7-[2-C-methyl-3,5-di-O-(1-oxo-octyl)-β-D-ribofuranosyl]-7H-pyrrolo[2,3-d]pyrimidine;

and the corresponding 5'-triphosphates;

or a pharmaceutically acceptable salt thereof.

6. The method of claim 5 wherein the compound is selected from the group consisting of:

4-amino-7-(2-C-methyl-β-D-ribofuranosyl)-7H-pyrrolo[2,3-d]pyrimidine, 4-amino-7-(2-C-fluoromethyl-β-D-ribofuranosyl)-7H-pyrrolo[2,3-d]pyrimidine, 4-amino-5-methyl-7-(2-C-methyl-β-D-ribofuranosyl)-7H-pyrrolo[2,3-d]pyrimidine, 4-amino-5-bromo-7-(2-C-methyl-β-D-ribofuranosyl)-7H-pyrrolo[2,3-d]pyrimidine, 4-amino-5-chloro-7-(2-C-methyl-β-D-ribofuranosyl)-7H-pyrrolo[2,3-d]pyrimidine,
4-amino-5-fluoro-7-(2-C-methyl-β-D-ribofuranosyl)-7H-pyrrolo[2,3-d]pyrimidine,
4-amino-2-fluoro-7-(2-C-methyl-β-D-ribofuranosyl)-7H-pyrrolo[2,3-d]pyrimidine,
6-amino-2-fluoro-9-(2-C-methyl-β-D-ribofuranosyl)purine,
2'-C-methyl-adenosine,
4-amino-7-[2-C-methyl-3-O-(1-oxo-octyl)-β-D-ribofuranosyl]-7H-pyrrolo[2,3-d]pyrimidine, and
4-amino-7-[2-C-methyl-3,5-di-O-(1-oxo-octyl)-β-D-ribofuranosyl]-7H-pyrrolo[2,3-d]pyrimidine;
and the corresponding 5'-triphosphates;
or a pharmaceutically acceptable salt thereof.

7. The method of claim 6 wherein the compound is
4-amino-7-(2-C-methyl-β-D-ribofuranosyl)-7H-pyrrolo[2,3-d]pyrimidine;
or a pharmaceutically acceptable salt thereof.

8. The method of claim 6 wherein the compound is
4-amino-7-[2-C-methyl-3-O-(1-oxo-octyl)-β-D-ribofuranosyl]-7H-pyrrolo[2,3-d]pyrimidine;
or a pharmaceutically acceptable salt thereof.

9. The method of claim 6 wherein the compound is
4-amino-7-(2-C-fluoromethyl-β-D-ribofuranosyl)-7H-pyrrolo[2,3-d]pyrimidine;
or a pharmaceutically acceptable salt thereof.

10. The method of claim 6 wherein the compound is
4-amino-7-[2-C-methyl-3,5-di-O-(1-oxo-octyl)-β-D-ribofuranosyl]-7H-pyrrolo[2,3-d]pyrimidine;
or a pharmaceutically acceptable salt thereof.

11. The method of claim 6 wherein the compound is
4-amino-5-fluoro-7-(2-C-methyl-β-D-ribofuranosyl)-7H-pyrrolo[2,3-d]pyrimidine;
or a pharmaceutically acceptable salt thereof.

12. The method of claim 2 wherein the compound is of structural formula II:

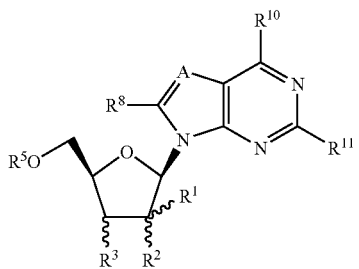

(II)

or a pharmaceutically acceptable salt thereof; wherein
A is N or C—$R^9$;
$R^1$ is $C_{1-3}$ alkyl, wherein alkyl is unsubstituted or substituted with hydroxy, amino, $C_{1-3}$ alkoxy, $C_{1-3}$ alkylthio, or one to three fluorine atoms;
$R^2$ is hydroxy, $C_{1-16}$ alkylcarbonyloxy, fluoro, or $C_{1-3}$ alkoxy;
$R^3$ is hydrogen, halogen, hydroxy, $C_{1-16}$ alkylcarbonyloxy, amino, or $C_{1-3}$ alkoxy;
$R^5$ is hydrogen, $C_{1-16}$ alkylcarbonyl, $P_3O_9H_4$, $P_2O_6H_3$, or $PO_3H_2$;
$R^8$ is hydrogen, amino, or $C_{1-4}$ alkylamino;
$R^9$ is hydrogen, cyano, methyl, halogen, or $CONH_2$; and
$R^{10}$ and $R^{11}$ are each independently hydrogen, halogen, hydroxy, amino, $C_{1-4}$ alkylamino, di($C_{1-4}$ alkyl)amino, or $C_{3-6}$ cycloalkylamino.

13. The method of claim 12 wherein
$R^1$ is methyl, fluoromethyl, hydroxymethyl, difluoromethyl, trifluoromethyl, or aminomethyl;
$R^2$ is hydroxy, $C_{1-6}$ alkylcarbonyloxy, fluoro, or methoxy;
$R^3$ is hydrogen, fluoro, hydroxy, $C_{1-16}$ alkylcarbonyloxy, amino, or methoxy;
$R^5$ is hydrogen, $C_{1-16}$ alkylcarbonyl, or $P_3O_9H_4$;
$R^8$ is hydrogen or amino;
$R^9$ is hydrogen, cyano, methyl, halogen, or $CONH_2$; and
$R^{10}$ and $R^{11}$ are each independently hydrogen, halogen, hydroxy, amino, $C_{1-4}$ alkylamino, di($C_{1-4}$ alkyl)amino, or $C_{3-6}$ cycloalkylamino.

14. The method of claim 13 wherein the compound is selected from the group consisting of:
4-amino-7-(2-C-methyl-β-D-ribofuranosyl)-7H-pyrrolo[2,3-d]pyrimidine,
4-methylamino-7-(2-C-methyl-β-D-ribofuranosyl)-7H-pyrrolo[2,3-d]pyrimidine,
4-dimethylamino-7-(2-C-methyl-β-D-ribofuranosyl)-7H-pyrrolo[2,3-d]pyrimidine,
4-cyclopropylamino-7-(2-C-methyl-β-D-ribofuranosyl)-7H-pyrrolo[2,3-d]pyrimidine,
4-amino-7-(2-C-hydroxymethyl-β-D-ribofuranosyl)-7H-pyrrolo[2,3-d]pyrimidine,
4-amino-7-(2-C-fluoromethyl-β-D-ribofuranosyl)-7H-pyrrolo[2,3-d]pyrimidine,
4-amino-5-methyl-7-(2-C-methyl-β-D-ribofuranosyl)-7H-pyrrolo[2,3-d]pyrimidine,
4-amino-7-(2-C-methyl-β-D-ribofuranosyl)-7H-pyrrolo[2,3-d]pyrimidine-5-carboxamide,
4-amino-7-(2-C-methyl-β-D-ribofuranosyl)-7H-pyrrolo[2,3-d]pyrimidine-5-carbonitrile,
4-amino-5-bromo-7-(2-C-methyl-β-D-ribofuranosyl)-7H-pyrrolo[2,3-d]pyrimidine,
4-amino-5-chloro-7-(2-C-methyl-β-D-ribofuranosyl)-7H-pyrrolo[2,3-d]pyrimidine,
4-amino-5-fluoro-7-(2-C-methyl-β-D-ribofuranosyl)-7H-pyrrolo[2,3-d]pyrimidine,
2,4-diamino-7-(2-C-methyl-β-D-ribofuranosyl)-7H-pyrrolo[2,3-d]pyrimidine,
2-amino-7-(2-C-methyl-β-D-ribofuranosyl)-7H-pyrrolo[2,3-d]pyrimidine,
2-amino-4-cyclopropylamino-7-(2-C-methyl-β-D-ribofuranosyl)-7H-pyrrolo[2,3-d]pyrimidine,
2-amino-7-(2-C-methyl-β-D-ribofuranosyl)-7H-pyrrolo[2,3-d]pyrimidin-4(3H)-one,
7-(2-C-methyl-β-D-ribofuranosyl)-7H-pyrrolo[2,3-d]pyrimidin-4(3H)-one,
4-amino-2-fluoro-7-(2-C-methyl-β-D-ribofuranosyl)-7H-pyrrolo[2,3-d]pyrimidine,
9-(2-C-methyl-β-D-ribofuranosyl)-2-amino-6-hydroxypurine,
9-(2-C-methyl-β-D-ribofuranosyl)-2-amino-6-cyclopropylaminopurine,
9-(2-C-methyl-β-D-ribofuranosyl)-2,6-diaminopurine,
9-(2-C-methyl-β-D-ribofuranosyl)-2-amino-6-methylaminopurine,
6-amino-2-fluoro-9-(2-C-methyl-β-D-ribofuranosyl)purine,
2'-C-methyl-adenosine,
4amino-7-[2-C-methyl-3-O-(1-oxo-octyl)-β-D-ribofuranosyl]-7H-pyrrolo[2,3-d]pyrimidine, and
4-amino-7-[2-C-methyl-3,5-di-O-(1-oxo-octyl)-β-D-ribofuranosyl]-7H-pyrrolo[2,3-d]pyrimidine;
and the corresponding 5'-triphosphates;
or a pharmaceutically acceptable salt thereof.

15. The method of claim 14 wherein the compound is selected from the group consisting of:

4-amino-7-(2-C-methyl-β-D-ribofuranosyl)-7H-pyrrolo[2,3-d]pyrimidine, 4-amino-7-(2-C-fluoromethyl-β-D-ribofuranosyl)-7H-pyrrolo[2,3-d]pyrimidine, 4-amino-5-methyl-7-(2-C-methyl-β-D-ribofuranosyl)-7H-pyrrolo[2,3-d]pyrimidine, 4-amino-5-bromo-7-(2-C-methyl-β-D-ribofuranosyl)-7H-pyrrolo[2,3-d]pyrimidine, 4-amino-5-chloro-7-(2-C-methyl-β-D-ribofuranosyl)-7H-pyrrolo[2,3-d]pyrimidine, 4-amino-5-fluoro-7-(2-C-methyl-β-D-ribofuranosyl)-7H-pyrrolo[2,3-d]pyrimidine, 4-amino-2-fluoro-7-(2-C-methyl-β-D-ribofuranosyl)-7H-pyrrolo[2,3-d]pyrimidine, 6-amino-2-fluoro-9-(2-C-methyl-β-D-ribofuranosyl)purine, 2'-C-methyl-adenosine, 4-amino-7-[2-C-methyl-3-O-(1-oxo-octyl)-β-D-ribofuranosyl]-7H-pyrrolo[2,3-d]pyrimidine, and 4-amino-7-[2-C-methyl-3,5-di-O-(1-oxo-octyl)-β-D-ribofuranosyl]-7H-pyrrolo[2,3-d]pyrimidine;

and the corresponding 5'-triphosphates;
or a pharmaceutically acceptable salt thereof.

16. The method of claim 15 wherein the compound is 4-amino-7-(2-C-methyl-β-D-ribofuranosyl)-7H-pyrrolo[2,3-d]pyrimidine;
or a pharmaceutically acceptable salt thereof.

17. The method of claim 15 wherein the compound is 4-amino-7-[2-C-methyl-3-O-(1-oxo-octyl)-β-D-ribofuranosyl]-7H-pyrrolo[2,3-d]pyrimidine;
or a pharmaceutically acceptable salt thereof.

18. The method of claim 15 wherein the compound is 4-amino-7-(2-C-fluoromethyl-β-D-ribofuranosyl)-7H-pyrrolo[2,3-d]pyrimidine;
or a pharmaceutically acceptable salt thereof.

19. The method of claim 15 wherein the compound is 4-amino-7-[2-C-methyl-3,5-di-O-(1-oxo-octyl)-β-D-ribofuranosyl]-7H-pyrrolo[2,3-d]pyrimidine;
or a pharmaceutically acceptable salt thereof.

20. The method of claim 15 wherein the compound is 4-amino-5-fluoro-7-(2-C-methyl-β-D-ribofuranosyl)-7H-pyrrolo[2,3-d]pyrimidine;
or a pharmaceutically acceptable salt thereof.

21. The method of claim 1 wherein said orthopoxvirus replication is vaccinia virus or variola virus replication.

22. The method of claim 2 wherein said orthopoxvirus infection is vaccinia virus or variola virus infection.

23. The method of claim 22 in combination with a therapeutically effective amount of another agent active against orthopoxvirus.

24. The method of claim 23 wherein said agent active against orthopoxvirus is cidofovir, ribavirin, levovirin, or viramidine.

25. The method of claim 8 wherein the orthopoxvirus replication is vaccinia virus or variola virus replication.

26. The method of claim 17 wherein the orthopoxvirus replication is vaccinia virus or variola virus replication.

27. A compound which is 6-amino-2-fluoro-9-(2-C-methyl-β-D-ribofuranosyl)purine or a pharmaceutically acceptable salt thereof.

* * * * *